US008021835B2

(12) United States Patent
Rice et al.

(10) Patent No.: US 8,021,835 B2
(45) Date of Patent: Sep. 20, 2011

(54) HCV CORECEPTOR AND METHODS OF USE THEREOF

(75) Inventors: Charles Rice, New York, NY (US); Matthew J. Evans, New York, NY (US); Thomas Von Hahn, Hamburg (DE)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 12/299,439

(22) PCT Filed: May 4, 2007

(86) PCT No.: PCT/US2007/010958
§ 371 (c)(1),
(2), (4) Date: Dec. 30, 2008

(87) PCT Pub. No.: WO2007/130646
PCT Pub. Date: Nov. 15, 2007

(65) Prior Publication Data
US 2009/0098123 A1    Apr. 16, 2009

Related U.S. Application Data

(60) Provisional application No. 60/797,378, filed on May 4, 2006.

(51) Int. Cl.
*C12Q 1/70* (2006.01)
*A61K 39/29* (2006.01)
(52) U.S. Cl. .......................... 435/5; 424/228.1; 530/350
(58) Field of Classification Search .................. None
See application file for complete search history.

(56) References Cited

U.S. PATENT DOCUMENTS

| 6,627,439 | B2 * | 9/2003 | Hoevel et al. ............... 435/326 |
| 2002/0142981 | A1 | 10/2002 | Horne et al. | |
| 2002/0150574 | A1 | 10/2002 | Hoevel et al. | |

FOREIGN PATENT DOCUMENTS

| WO | 2007/130646 A2 | 11/2007 |
| WO | 2010040001 A1 | 4/2010 |

OTHER PUBLICATIONS von Hahn et al., "Hepatitis C Virus Entry," Journal of Biological Chemsitry, vol. 283 No. 7, pp. 3689-3693 (Feb. 2008).*
Bowie et al., "Deciphering the message in protein sequences: tolerance to amino acid substitutions ," Science, vol. 247 No. 4948, pp. 1306-1310 (Mar. 1990).*
Evans et al.; "Claudin-1 is a Hepatitis C Virus Co-receptor Required for a Late Steph in Entry"; Article; Feb. 2007; pp. 1-5, supplementary information pp. 1-17; Nature Publishing Group.
Furuse et al.; "Claudin-based Tight Junctions are Crucial for the Mammalian Epidermal Barrier: A Lesson from Claudin-1-deficient Mice"; The Journal of Cell Biology; Mar. 18, 2002; pp. 1099-1111; vol. 156, No. 6; The Rockefeller University Press.
Hsu et al.; "Hepatitis C Virus Glycoproteins Mediate pH-Dependent Cell Entry of Pseudotyped Retrovial Particles"; Article; Jun. 10, 2003; pp. 7271-7276; vol. 100, No. 12; PNAS.
Supplementary European Search Report for Corresponding European Application No. 07809043.8 dated Sep. 24, 2009.
Von Hahn et al., "Identification of Claudin-1 as an Essential Cellular Cell Entry Factor for Hepatitis C Virus", Hepatology, Oct. 4, 2006, pp. 197A, vol. 44, No. 4.
Eren et al., "Preclinical Evaluation of Two Neutralizing Human Monoclonal Antibodies Against Hepatitis C Virus (HCV): A Potential Treatment to Prevent HCV Reinfection in Liver Transplant Patients", Journal of Virology, Mar. 1, 2006, pp. 2654-2664, vol. 80, No. 6, The American Society for Microbiology, US.
Bartosch et al., "In Vitro Assay for Neutralizing Antibody to Hepatitis C Virus: Evidence for Broadly Conserved Neutralization Epitopes", Proceedings of the National Academy of Sciences of USA, Nov. 25, 2003, pp. 14199-14204, vol. 100, No. 24, National Academy of Science, Washington, DC, US.
Keck et al., "Human Monoclonal Antibody to Hepatitis C Virus E1 Glycoprotein that Blocks Virus Attachment and Viral Infectivity", Journal of Virology, Jul. 2004, pp. 7257-7263, vol. 78, No. 13.
Steinmann et al., "Inhibition of Hepatitis C Virus-Like Particle Binding to Target Cells by Antiviral Antibodies in Acute and Chronic Hepatitis C", Journal of Virology, Sep. 2004, pp. 9030-9040, vol. 78, No. 17.
Zheng et al., "Involvement of Claudin-7 in HIV Infection of CD4 (−) Cells", Retrovirology, Dec. 20, 2005, pp. 79, vol. 2, No. 1, Biomed Central Ltd., London, GB.
Cocquerel et al., "Hepatitis C Virus Entry: Potential Receptors and Their Biological Functions", Journal of General Virology, Feb. 14, 2006, pp. 1075-1084, vol. 87.
Turksen et al., "Permeability Barrier Dysfunction in Transgenic Mice Overexpressing Claudin 6", Development, Apr. 2002, pp. 1775-1784, vol. 129.
Furuse et al., "Claudin-1 and -2: Novel Integral Membrane Proteins Localizing at Tight Junctions with no Sequence Similarity to Occludin", J Cell Biol, Jun. 29, 1998, pp. 1539-1550, vol. 141, No. 7.
International Preliminary Report on Patentability (Chapter I) for PCT/US2007/010958 dated Nov. 13, 2008.
International Search Report and Written Opinion for PCT/US2007/010958 dated Jul. 28, 2008.
Zhang et al., "CD81 Is Required for Hepatitis C Virus Glycoprotein-Mediated Viral Infection", Journal of Virology, Feb. 2004, pp. 1448-1455, vol. 78, No. 3.
McKeating et al., "Diverse Hepatitis C Virus Glycoproteins Mediate Viral Infection in a CD81-Dependent Manner", Journal of Virology, Aug. 2004, pp. 8496-8505, vol. 78, No. 16.
Haid et al., "Mouse-Specific Residues of Claudin-1 Limit Hepatitis C Virus Genotype 2a Infection in a Human Hepatocyte Cell Line", Journal of Virology, Jan. 2010, pp. 964-975, vol. 84, No. 2.

* cited by examiner

*Primary Examiner* — Stacy B Chen
(74) *Attorney, Agent, or Firm* — Thompson Coburn LLP

(57) ABSTRACT

The invention relates to the discovery that the Claudin-1 protein functions as a co-receptor for entry of HCV into cells. Methods of inhibiting, preventing or mitigating HCV infections by inhibiting HCV interactions with Claudin-1 are provided. Methods of identifying agents or compounds that interfere with HCV interactions with Claudin-1 are also provided. Finally, useful kits, cell culture compositions, agents, and compounds related to the inhibition of HCV interactions with Claudin-1 are also disclosed.

11 Claims, 29 Drawing Sheets

Figure 27

| | pH treatment | |
|---|---|---|
| | pH7 | pH5 |
| VSV-G | | |
| HCV E1/E2 | | |

Viral glycoprotein

SEQUENCE LISTING

```
<160> NUMBER OF SEQ ID NOS: 31

<210> SEQ ID NO 1
<211> LENGTH: 211
<212> TYPE: PRT
<213> ORGANISM: Homo sapiens

<400> SEQUENCE: 1

Met Ala Asn Ala Gly Leu Gln Leu Leu Gly Phe Ile Leu Ala Phe Leu
1               5                   10                  15

Gly Trp Ile Gly Ala Ile Val Ser Thr Ala Leu Pro Gln Trp Arg Ile
            20                  25                  30

Tyr Ser Tyr Ala Gly Asp Asn Ile Val Thr Ala Gln Ala Met Tyr Glu
        35                  40                  45

Gly Leu Trp Met Ser Cys Val Ser Gln Ser Thr Gly Gln Ile Gln Cys
    50                  55                  60

Lys Val Phe Asp Ser Leu Leu Asn Leu Ser Ser Thr Leu Gln Ala Thr
```

```
             65                  70                  75                  80
Arg Ala Leu Met Val Val Gly Ile Leu Leu Gly Val Ile Ala Ile Phe
                    85                  90                  95

Val Ala Thr Val Gly Met Lys Cys Met Lys Cys Leu Glu Asp Asp Glu
                100                 105                 110

Val Gln Lys Met Arg Met Ala Val Ile Gly Gly Ala Ile Phe Leu Leu
            115                 120                 125

Ala Gly Leu Ala Ile Leu Val Ala Thr Ala Trp Tyr Gly Asn Arg Ile
        130                 135                 140

Val Gln Glu Phe Tyr Asp Pro Met Thr Pro Val Asn Ala Arg Tyr Glu
145                 150                 155                 160

Phe Gly Gln Ala Leu Phe Thr Gly Trp Ala Ala Ser Leu Cys Leu
                165                 170                 175

Leu Gly Gly Ala Leu Leu Cys Cys Ser Cys Pro Arg Lys Thr Thr Ser
                180                 185                 190

Tyr Pro Thr Pro Arg Pro Tyr Pro Lys Pro Ala Pro Ser Ser Gly Lys
                195                 200                 205

Asp Tyr Val
    210

<210> SEQ ID NO 2
<211> LENGTH: 211
<212> TYPE: PRT
<213> ORGANISM: Mus musculus

<400> SEQUENCE: 2

Met Ala Asn Ala Gly Leu Gln Leu Leu Gly Phe Ile Leu Ala Ser Leu
1               5                   10                  15

Gly Trp Ile Gly Ser Ile Val Ser Thr Ala Leu Pro Gln Trp Lys Ile
                20                  25                  30

Tyr Ser Tyr Ala Gly Asp Asn Ile Val Thr Ala Gln Ala Ile Tyr Glu
            35                  40                  45

Gly Leu Trp Met Ser Cys Val Ser Gln Ser Thr Gly Gln Ile Gln Cys
        50                  55                  60

Lys Val Phe Asp Ser Leu Leu Asn Leu Asn Ser Thr Leu Gln Ala Thr
65                  70                  75                  80

Arg Ala Leu Met Val Ile Gly Ile Leu Leu Gly Leu Ile Ala Ile Phe
                    85                  90                  95

Val Ser Thr Ile Gly Met Lys Cys Met Arg Cys Leu Glu Asp Asp Glu
                100                 105                 110

Val Gln Lys Met Trp Met Ala Val Ile Gly Gly Ile Ile Phe Leu Ile
            115                 120                 125

Ser Gly Leu Ala Thr Leu Val Ala Thr Ala Trp Tyr Gly Asn Arg Ile
        130                 135                 140

Val Gln Glu Phe Tyr Asp Pro Leu Thr Pro Ile Asn Ala Arg Tyr Glu
145                 150                 155                 160

Phe Gly Gln Ala Leu Phe Thr Gly Trp Ala Ala Ala Ser Leu Cys Leu
                165                 170                 175

Leu Gly Gly Val Leu Leu Ser Cys Ser Cys Pro Arg Lys Thr Thr Ser
                180                 185                 190

Tyr Pro Thr Pro Arg Pro Tyr Pro Lys Pro Thr Pro Ser Ser Gly Lys
                195                 200                 205

Asp Tyr Val
    210
```

```
<210> SEQ ID NO 3
<211> LENGTH: 211
<212> TYPE: PRT
<213> ORGANISM: Homo sapiens

<400> SEQUENCE: 3

Met Ala Asn Ser Gly Leu Gln Leu Leu Gly Phe Ser Met Ala Leu Leu
1               5                   10                  15

Gly Trp Val Gly Leu Val Ala Cys Thr Ala Ile Pro Gln Trp Gln Met
            20                  25                  30

Ser Ser Tyr Ala Gly Asp Asn Ile Ile Thr Ala Gln Ala Met Tyr Lys
        35                  40                  45

Gly Leu Trp Met Asp Cys Val Thr Gln Ser Thr Gly Met Met Ser Cys
    50                  55                  60

Lys Met Tyr Asp Ser Val Leu Ala Leu Ser Ala Ala Leu Gln Ala Thr
65                  70                  75                  80

Arg Ala Leu Met Val Val Ser Leu Val Leu Gly Phe Leu Ala Met Phe
                85                  90                  95

Val Ala Thr Met Gly Met Lys Cys Thr Arg Cys Gly Gly Asp Asp Lys
            100                 105                 110

Val Lys Lys Ala Arg Ile Ala Met Gly Gly Ile Phe Ile Val
            115                 120                 125

Ala Gly Leu Ala Thr Leu Val Ala Cys Ser Trp Tyr Gly His Gln Ile
        130                 135                 140

Val Thr Asp Phe Tyr Asn Pro Leu Ile Pro Thr Asn Ile Lys Tyr Glu
145                 150                 155                 160

Phe Gly Pro Ala Ile Phe Ile Gly Trp Ala Gly Ser Ala Leu Val Ile
                165                 170                 175

Leu Gly Gly Ala Leu Leu Ser Cys Ser Cys Pro Gly Asn Glu Ser Lys
            180                 185                 190

Ala Gly Tyr Arg Ala Pro Arg Ser Tyr Pro Lys Ser Asn Ser Ser Lys
        195                 200                 205

Glu Tyr Val
    210

<210> SEQ ID NO 4
<211> LENGTH: 37
<212> TYPE: DNA
<213> ORGANISM: Artificial
<220> FEATURE:
<223> OTHER INFORMATION: Primer sequence

<400> SEQUENCE: 4
gggatccggg atggccaagt tgaccagtgc cgttccg                                37

<210> SEQ ID NO 5
<211> LENGTH: 42
<212> TYPE: DNA
<213> ORGANISM: Artificial
<220> FEATURE:
<223> OTHER INFORMATION: Primer Sequence

<400> SEQUENCE: 5
cccctcgagt ctagatcagt cctgctcctc ggccacgaag tg                         42

<210> SEQ ID NO 6
<211> LENGTH: 43
<212> TYPE: DNA
<213> ORGANISM: Artificial
<220> FEATURE:
<223> OTHER INFORMATION: Primer Sequence
```

```
<400> SEQUENCE: 6 gggggatcc gtcatggcca acgcggggct gcagctgttg ggc          43

<210> SEQ ID NO 7
<211> LENGTH: 40
<212> TYPE: DNA
<213> ORGANISM: Artificial
<220> FEATURE:
<223> OTHER INFORMATION: Primer sequence

<400> SEQUENCE: 7
ggggctcgag tcacacgtag tctttcccgc tggaaggtgc             40

<210> SEQ ID NO 8
<211> LENGTH: 43
<212> TYPE: DNA
<213> ORGANISM: Artificial
<220> FEATURE:
<223> OTHER INFORMATION: Primer sequence

<400> SEQUENCE: 8 gggggggatcc gccatgtcca tgggcctgga gatcacgggc acc        43

<210> SEQ ID NO 9
<211> LENGTH: 40
<212> TYPE: DNA
<213> ORGANISM: Artificial
<220> FEATURE:
<223> OTHER INFORMATION: Primer sequence

<400> SEQUENCE: 9
gggggtcgac ttagacgtag tccttgcggt cgtagcctgt             40

<210> SEQ ID NO 10
<211> LENGTH: 40
<212> TYPE: DNA
<213> ORGANISM: Artificial
<220> FEATURE:
<223> OTHER INFORMATION: Primer sequence

<400> SEQUENCE: 10 gggggggatcc atggccaatt cgggcctgca gttgctgggc            40

<210> SEQ ID NO 11
<211> LENGTH: 40
<212> TYPE: DNA
<213> ORGANISM: Artificial
<220> FEATURE:
<223> OTHER INFORMATION: Primer sequence

<400> SEQUENCE: 11 ggggtcgac tcacacatac tccttggaag agttggactt              40

<210> SEQ ID NO 12
<211> LENGTH: 43
<212> TYPE: DNA
<213> ORGANISM: Artificial
<220> FEATURE:
<223> OTHER INFORMATION: Primer sequence

<400> SEQUENCE: 12 gggggggatcc gtcatggcca acgcggggct gcagctgctg ggt        43

<210> SEQ ID NO 13
<211> LENGTH: 43
```

```
<212> TYPE: DNA
<213> ORGANISM: Artificial
<220> FEATURE:
<223> OTHER INFORMATION: Primer sequence

<400> SEQUENCE: 13
ggggctcgag tcacacatag tctttcccac tagaaggtgt tgg              43

<210> SEQ ID NO 14
<211> LENGTH: 40
<212> TYPE: DNA
<213> ORGANISM: Artificial
<220> FEATURE:
<223> OTHER INFORMATION: Primer sequence

<400> SEQUENCE: 14 gggggggatcc ggaatggtga gcaagggcga ggagctgttc                 40

<210> SEQ ID NO 15
<211> LENGTH: 40
<212> TYPE: DNA
<213> ORGANISM: Artificial
<220> FEATURE:
<223> OTHER INFORMATION: Primer sequence

<400> SEQUENCE: 15
ggggagatct cttgtacagc tcgtccatgc cgagagtgat                  40

<210> SEQ ID NO 16
<211> LENGTH: 48
<212> TYPE: DNA
<213> ORGANISM: Artificial
<220> FEATURE:
<223> OTHER INFORMATION: Primer sequence

<400> SEQUENCE: 16
cttgtcgtca tcgtccttat agtcgaccaa tgtgctgctc agattcag         48

<210> SEQ ID NO 17
<211> LENGTH: 51
<212> TYPE: DNA
<213> ORGANISM: Artificial
<220> FEATURE:
<223> OTHER INFORMATION: Primer sequence

<400> SEQUENCE: 17
gactataagg acgatgacga caagcttcaa gcaacgcgtg ccttgatggt g     51

<210> SEQ ID NO 18
<211> LENGTH: 76
<212> TYPE: DNA
<213> ORGANISM: Artificial
<220> FEATURE:
<223> OTHER INFORMATION: Primer sequence

<400> SEQUENCE: 18 ggggggtcgac tacaaagacc atgacggtga ttataaagat catgatatcg actataagga   60
cgatgacgac aagctt                                            76

<210> SEQ ID NO 19
<211> LENGTH: 27
<212> TYPE: DNA
<213> ORGANISM: Artificial
<220> FEATURE:
<223> OTHER INFORMATION: Primer sequence

<400> SEQUENCE: 19
```

```
caccatgggt ttcccctttt ctatctt                                    27

<210> SEQ ID NO 20
<211> LENGTH: 39
<212> TYPE: DNA
<213> ORGANISM: Artificial
<220> FEATURE:
<223> OTHER INFORMATION: Primer sequence

<400> SEQUENCE: 20
ctactatgct tcggcctggc ccaacaagat gagcatcca                        39

<210> SEQ ID NO 21
<211> LENGTH: 19
<212> TYPE: RNA
<213> ORGANISM: Artificial
<220> FEATURE:
<223> OTHER INFORMATION: siRNA 306 targeting cldn1

<400> SEQUENCE: 21
aguggaggau uuacuccua                                             19

<210> SEQ ID NO 22
<211> LENGTH: 19
<212> TYPE: RNA
<213> ORGANISM: Artificial
<220> FEATURE:
<223> OTHER INFORMATION: siRNA 525 targeting cldn1

<400> SEQUENCE: 22
ugaaguguau gaagugcuu                                             19

<210> SEQ ID NO 23
<211> LENGTH: 19
<212> TYPE: RNA
<213> ORGANISM: Artificial
<220> FEATURE:
<223> OTHER INFORMATION: siRNA 635 targeting cldn1

<400> SEQUENCE: 23
ugguauggca auagaaucg                                             19

<210> SEQ ID NO 24
<211> LENGTH: 19
<212> TYPE: RNA
<213> ORGANISM: Artificial
<220> FEATURE:
<223> OTHER INFORMATION: siRNA 804 targeting cldn1

<400> SEQUENCE: 24
caccaaggcc cuauccaaa                                             19

<210> SEQ ID NO 25
<211> LENGTH: 19
<212> TYPE: RNA
<213> ORGANISM: Artificial
<220> FEATURE:
<223> OTHER INFORMATION: siRNA 921 targeting cldn1

<400> SEQUENCE: 25
uaacauuagg accuuagaa                                             19

<210> SEQ ID NO 26
<211> LENGTH: 19
<212> TYPE: RNA
<213> ORGANISM: Artificial
```

```
<220> FEATURE:
<223> OTHER INFORMATION: siRNA 1259 targeting cldn1

<400> SEQUENCE: 26
uuccauauug augaagaug                                                19

<210> SEQ ID NO 27
<211> LENGTH: 19
<212> TYPE: RNA
<213> ORGANISM: Artificial
<220> FEATURE:
<223> OTHER INFORMATION: RNA sequence without close homology to any
      expressed human sequence

<400> SEQUENCE: 27
uagcagcuaa acacaucaa                                                19

<210> SEQ ID NO 28
<211> LENGTH: 19
<212> TYPE: RNA
<213> ORGANISM: Artificial
<220> FEATURE:
<223> OTHER INFORMATION: siRNA targeting CD81

<400> SEQUENCE: 28
ugauguucgu uggcuuccu                                                19

<210> SEQ ID NO 29
<211> LENGTH: 20
<212> TYPE: DNA
<213> ORGANISM: Artificial
<220> FEATURE:
<223> OTHER INFORMATION: Primer sequence

<400> SEQUENCE: 29
cttcacgcag aaagcgtcta                                               20

<210> SEQ ID NO 30
<211> LENGTH: 20
<212> TYPE: DNA
<213> ORGANISM: Artificial
<220> FEATURE:
<223> OTHER INFORMATION: Primer sequence

<400> SEQUENCE: 30
caagcaccct atcaggcagt                                               20

<210> SEQ ID NO 31
<211> LENGTH: 20
<212> TYPE: DNA
<213> ORGANISM: Artificial
<220> FEATURE:
<223> OTHER INFORMATION: Probe sequence
<220> FEATURE:
<221> NAME/KEY: misc_feature
<222> LOCATION: (1)..(1)
<223> OTHER INFORMATION: FAM labeled
<220> FEATURE:
<221> NAME/KEY: misc_feature
<222> LOCATION: (20)..(20)
<223> OTHER INFORMATION: MGBNFQ labeled

<400> SEQUENCE: 31
tatgagtgtc gtgcagcctc                                               20
```

HCV CORECEPTOR AND METHODS OF USE THEREOF

CROSS-REFERENCE TO RELATED APPLICATIONS

This application is a National Stage of International Application No. PCT/US2007/010958, filed May 4, 2007, which claims the benefit of U.S. Provisional Patent Application No. 60/797,378, filed May 4, 2006, both of which are herein incorporated by reference in their entireties.

STATEMENT REGARDING FEDERALLY SPONSORED RESEARCH OR DEVELOPMENT

This work was supported in part by National Institutes of Health grant AI072613-01 to C. M. Rice. The government has certain rights to this invention.

BACKGROUND OF THE INVENTION

About 2% of the world population (123 million individuals) are chronically infected with the hepatitis C virus (HCV). Chronic infection puts these individuals at risk for the development of hepatitis, cirrhosis, liver failure and hepatocellular carcinoma making chronic hepatitis C the leading cause for liver transplantation worldwide. In the United States a seroprevalence rate of 1.8% has been reported and HCV is associated with more than half of an increasing number of newly diagnosed hepatocellular carcinomas.

Current therapy combining pegylated interferon-alpha with ribavirin achieves cure rates of just above 50% (Fried et al., 2002, N Engl J Med 347:975-82; Manns et al., 2001, Lancet 358:958-965). Several difficult to treat patient groups show decreased response rates or cannot tolerate therapy at all. These include patients that have failed to respond to standard therapy, African Americans, patients with HIV-coinfection or end-stage liver disease and patients after liver transplantation. Currently, HCV infection of the graft after liver transplantation is universal, usually leading to rapid fibrosis progression and subsequent graft failure. This accounts for the poor outcome of liver transplantation for HCV-induced cirrhosis compared to other indications (Forman et al., 2002, Gastroenterology 122:889-96). Targeting HCV cell entry in this setting holds promise as a therapy capable of blocking viral entry even for a short period of time might prevent graft re-infection and thus turn liver transplantation from a palliative into a curative procedure. Hopefully, a more complete understanding of early HCV life cycle events will identify promising targets for this purpose.

Recent technical developments have opened up exciting new possibilities for molecular studies of hepatitis C virus (HCV). In the past decade, molecular clones that are functional for chimpanzee infection, efficient cell culture systems for studying RNA replication (replicons), and retroviral pseudotypes harboring functional HCV glycoproteins (HCVpp) have been developed. More recently, derivatives of a genotype 2a isolate, JFH-1, have yielded relatively high titers of cell culture infectious particles (HCVcc). Importantly, HCVcc is infectious in chimpanzees and a murine-human xenograft model and viral production in animals (chHCVcc or muHCVcc) retaining infectivity in cultured cells has been shown. This creates a complete and valuable set of reagents to study HCV neutralization and entry.

The tetraspanin CD81 and scavenger receptor BI/II (SR-BI/II) are cell surface molecules that bind the HCV E2 glycoprotein and participate in HCV entry. However, expression of these two molecules, in conjunction with numerous other candidate entry factors, is insufficient to render cells fully permissive for HCV entry. Thus, there necessarily remains an additional, as yet unidentified HCV coreceptor.

HCV is a member of the family Flaviviridae, which also includes Pestiviruses and Flaviviruses. The HCV virion consists of an enveloped nucleocapsid containing the viral genome, a single, positive stranded RNA of approximately 9,600 nucleotides. Viral entry into the host cell is thought to require a tightly regulated interaction between the viral envelope proteins, E1 and E2, and host proteins at the cell surface. Moreover, it has been shown that host cell infection requires endosomal acidification suggesting that fusion of the viral envelope with cellular membranes is a pH triggered event. After cell entry the nucleocapsid is released into the cytosol and the viral RNA is translated through action of an internal ribosome entry site (IRES) present in the 5' untranslated region (5'UTR). The HCV genome encodes a single long open reading frame giving rise to a viral polyprotein of over 3000 amino acids that then undergoes co- and post-translational proteolytic processing to generate the mature viral proteins: C-E1-E2-p7-NS2-NS3-NS4A-NS4B-NS5A-NS5B (FIG. 1). The viral structural proteins, including core, the capsid protein E1, and E2, are encoded by the first third of the polyprotein. p7 (a putative ion channel) and nonstructural (NS) proteins, encoded by the C-terminal two-thirds of the polyprotein, are components of the HCV RNA replication complex. The replication of the viral genome through a negative strand RNA intermediate occurs.

Recently, pseudotyped retroviral particles were developed to study HCV entry. To generate HCVpp, 293T cells are transfected with expression vectors encoding (1) unmodified HCV E1E2, (2) the gag-pol proteins of either MLV or HIV and (3) a packaging competent (but gag-pol and env deficient) retroviral genome containing either a GFP or lacZ reporter gene. This results in the release of infectious HIV or MLV nucleocapsids surrounded by an envelope containing HCV glycoproteins (Bartosch, B., J. Dubuisson, and F. L. Cosset. 2003. Infectious hepatitis C virus pseudo-particles containing functional E1-E2 envelope protein complexes. J Exp Med 197:633-642). Alternatively, a two vector system using an envelope deficient HIV genome with a luciferase reporter and an HCV-E1E2 expressing vector can be employed (Hsu, M., J. Zhang, M. Flint, C. Logvinoff, C. Cheng-Mayer, C. M. Rice, and J. A. McKeating. 2003. Hepatitis C virus glycoproteins mediate pH-dependent cell entry of pseudotyped retroviral particles. Proc. Natl. Acad. Sci. USA 100:7271-76). These HCVpp systems take advantage of the ability of retroviruses to incorporate heterologous glycoproteins into their envelope. HCVpp can infect a number of liver derived human cell lines and their reporter genes allow convenient quantification of target cell infection, making HCVpp the first robust assay for the study of HCV glycoprotein mediated cell entry.

More has been elucidated in the life cycle of HCV via the development of HCVcc (FIG. 2). This was made possible through the discovery of a genotype 2a HCV isolate from a Japanese patient with acute fulminant hepatitis (JFH)-1, that is capable of efficient subgenomic RNA replication in multiple cell types without the need for adaptive mutations (Date, T. et al. 2004. J Biol Chem. 279:22371-6; Kato, T. et al. 2003 Gastroenterology 125:1808-17; Kato, T. et al. 2005 J. Virol 79:592-6). Surprisingly, when full length JFH-1 genome RNA was transfected into Huh-7 cells, viral particles, termed HCVcc, were released that were capable of infecting naïve cells. Efficient in vitro systems based on the JFH genome recapitulating the entire HCV life cycle have been developed. Virus produced from full length JFH-1 RNA exhibits characteristics predicted for an HCV virion: the infectivity of these particles is blocked by antibodies against E2 or CD81 and by purified soluble CD81; moreover, virion density is similar to that found in sera of infected individuals. Although JFH-1 initially yielded low titers, higher viral titers were obtained by using Huh-7.5 cells and derived sublines (Lindenbach, B.D. et al. 2005 Science 309:623-6; Zhong J.P., et al. 2005 Proc Natl Acad Sci USA 102:9294-9), which are highly permissive for HCV replication (Blight et al. 2002. J. Virol. 76:13001-14) due to a defect in the RIG-I intrinsic immune response pathway (Sumpter et al. 2005. J Virol 79:2689-99). Virion production was further enhanced through the use of a chimeric genotype 2a full length genome, expressing the core through NS2 region of the HCJ6 HCV isolate cloned into the JFH-1 genome (J6/JFH) (FIG. 1B), which, unexpectedly, produced higher initial titers post transfection than the full length JFH-1 genome (Lindenbach, B.D., et al. 2005 Science 309:623-6. Very recently, cell culture grown HCVcc has been used to infect both chimpanzees and uPA-SCID mice transplanted with human hepatocytes (Lidenbach, B.D., et al. 2006 Proc. Natl. Acad. Sci. USA 103 In press). In both cases rising viral loads and an infection sustained for several weeks ensued, validating the usefulness of the HCVcc system. More importantly, virus recovered from HCVcc inoculated animals (ex vivo HCVcc; chHCVcc and muHCVcc for virus recovered from chimps and mice, respectively) was infectious in cell culture establishing the first robust ex vivo culture system. Virus recovered from infected animals displayed both altered biophysical properties and increased specific infectivity (ratio of infectious units to RNA copies) indicating that ex vivo HCVcc is of great use in elucidating the role of host factors in modulating HCV infection.

Using HCVpp, much has been learned about the mechanism of HCV cell entry. Evaluations of entry using the HCVcc system yield comparable results with regard to cell entry properties such as CD81 dependence, restriction to human hepatoma cell lines and neutralization by anti-E2 antibodies. Even with HCVcc available, HCVpp still offer certain advantages, most notably (1) the ability to investigate HCV glycoprotein dependent entry in cells non-permissive to HCV replication and (2) the availability of stringent controls in the form of pseudoparticles bearing glycoproteins from viruses other than HCV, such as VSV or MLV, and pseudoparticles devoid of glycoproteins (no envelope). Nonetheless, future studies are needed to elucidate possible mechanistic differences between the cell entry properties of HCVpp, HCVcc and ex vivo HCVcc.

HCVpp infectivity requires both E1 and E2 with their intact transmembrane domains (Bartosch, B. J., et al. 2003 J Exp Med 197:633-642; Hsu, M., et al. 2003 Proc. Natl. Acad. Sci. USA 100:7271-76). The structure of the infectious unit in vivo may be more complex through the above mentioned association between the virus and host serum factors including different lipoprotein species (VLDL, LDL, HDL) and immunoglobulins (Kono, Y., J et al. 2003 Med Virol 70:42-8; Monazahian, M., et al. 2000 Journal of Medical Virology 57:223-9; Thomssen, R., et al. 1992 Med. Microbiol. Immunol. 181:293-300; Thomssen, R., et al. 1993 Med. Microbiol. Immunol. 182:329-334). Such associations may explain the heterogeneous buoyant density observed for both plasma-derived HCV (1.03-1.2 g/ml) (Bradley, D., J. et al. 1991 Med. Virol. 34:206-208; Hijikata, M., J. et al. 1993 Virol. 67:1953-1958; Thomssen, R., et al. 1993 Med. Microbiol. Immunol. 182:329-334) and HCVcc (1.04-1.18 g/ml) (Lindenbach, B.D., et al. 2005 Science 309:623-6; Wakita, T., et al. 2005 Nat Med 11:791-6; Zhong, 3., et al. 2005 Proc Nati Acad Sci USA 102:9294-9). The highest infectivity seems to be associated with fractions of low to medium density (1.11 g/ml and below) (Bradley, D., J. et al. 1991 Med. Virol. 34:206-208; Hijikata, M., J. et al. 1993 Virol. 67:1953-1958: Lindenbach, B.D.,et al. 2005 Science 309:623-6) indicating that an interaction with plasma lipids may enhance virion infectivity.

Low pH induces conformational changes in E2 and the dissociation of E1E2 complexes indicating the involvement of a pH-triggered step in the entry process (Flint. M., et al. 1999 J. Virol 73:6782-6790; Op De Beeck, A., et al. 2004 J Virol 78:2994-3002). In keeping with this, HCVpp entry has been shown to be sensitive to endosomal acidification inhibitors such as ammonium chloride, bafilomycin and concanamycin, as is HCVcc entry, as shown herein. This pH dependence indicates that virus interaction with putative cell surface receptors is followed by endocytotic uptake of the particle rather than fusion at the plasma membrane and that endosomal low pH is required, in some embodiments, to initiate virus-cell membrane fusion. An endosomal route of entry has also been described for the related flaviviruses (Gollins, S.W., et al. 1985 J. Gen. Virol. 66:1969-1982; Gollins, S.W.,et al 1986 J. Gen. Virol. 67:157-166) as well as more evolutionarily distant alphaviruses (Helenius. A., et al. 1980 J Cell Biol 84:404-20).

Currently, the minimal host cell factor requirement for HCV cell entry (i.e., the sequence of events beginning with attachment to the host cell and ending with cytoplasmic delivery of the nucleocapsid) is not known. Numerous molecules have been proposed to function as HCV (co-)receptors (i.e., cell surface molecules required for entry that bind virus). However, none of these have had a precise function in the entry process conclusively defined, nor has the temporal sequence of interactions required for entry been determined. Beyond (co-)receptors, additional molecules that perform other functions in the entry process (e.g., endosomal proteases) may be required. Finally, there may also be molecules that are not essential but rather facilitate HCV entry (facilitating factors).

There appears to be a requirement for CD81 for HCV cell entry. CD81, a member of the tetraspanin superfamily with four transmembrane domains and short cytosolic N- and C-terminal tails, was initially identified as a candidate HCV receptor based on its ability to bind sE2[124]. The HCV-CD81 interaction is thought to take place between the CD81 large-extracellular loop (LEL) between transmembrane domains 3 and 4 (Drummer et al., 2005, Biochem Biophys Res Commun 328:251-7, Drummer et al., 2002, J Virol 76:11143-7; Higginbottom et al., 2000, J Virol 74:3642-9) and a conformational epitope on E2[52]. Several pieces of evidence strongly support CD81's role as an essential (co-)receptor for HCV: (1) The human hepatoma cell line HepG2 does not express CD81 and cannot be infected with HCVpp or HCVcc, but becomes infectable with both upon transduction with CD81 (Bartosch et al., 2003, J Biol Chem 278:41624-30; Lindenbach et al., 2005, Science 309:623-6; Zhang et al., 2004, J Virol 78:1448-55). This CD81 requirement in HepG2 cells is conserved across HCVpp bearing E1 and E2 from all known genotypes (Lavillette et al., 2005, Hepatology 41:265-74; McKeating et al., 2004, J Virol 78:8496-505). (2) Knockdown of CD81 expression using siRNA abrogates susceptibility to HCVpp166. (3) Antibodies against CD81, as well as soluble forms of the large extracellular loop of CD81, block HCVpp and HCVcc infection in a dose-dependent manner (Bartosch, B., et al. 2003 J Exp Med 197:633-642; Hsu, M., et al. 2003 Proc. Natl. Acad. Sci. USA 100:7271-76; Lindenbach, B.D., et al. 2005 Science 309:623-6; Wakita, T.. et al. 2005 Nat Med 11:791-6; Zhong, J., et al. 2005 Proc Natl Acad Sci USA 102:9294-9). However, other factors besides CD81 must be required for entry since CD81 expression alone is insufficient to allow HCVpp entry (Bartosch. B., et al. 2003 J Exp Med 197:633-642; Hsu, M., et al. 2003 Proc. Natl. Acad. Sci. USA 100:7271-76; Zhang, J., et al. 2004 J Virol 78:1448-55) and the expression of CD81 in all human cell types except erythrocytes and platelets (Levy, S., et al. 1998 Annu. Rev. Immunol. 16:89-109) does not explain HCV's apparent liver tropism. The precise role of CD81 in the entry process is unclear; some evidence suggests it may function as a co-receptor, interacting with the virus only after binding of the virus to another receptor molecule has occurred (Cormier. E.G., et al. 2004 Proc Natl Acad Sci USA 101:7270-4).

Like CD81, scavenger receptor class B member I (SR-BI) was first proposed as an HCV entry factor because of its ability to bind sE2$^{136}$. SR-BI is expressed at high levels in the liver and steroidogenic tissues with lower levels detectable in placenta, small intestine, monocytes/macrophages and other tissues. It mediates selective uptake of cholesterol esters from HDL into the cellular membrane (Acton, S., et al. 1996 Science 271:518-20: Rodrigueza, W.V., et al. 1999 J. Biol Chem 274:20344-50) and possibly also endocytosis of entire HDL particles (Silver, D.L., et al. 2001 J Biol Chem 276:25287-93). The role of SR-BI in HCV cell entry is less clear than that of CD81. No SR-BI negative cell line that becomes permissive to HCV infection when transfected with SR-BI has been reported. Antibodies and siRNA directed against SR-BI inhibit HCVpp infection (Bartosch et al., 2003, J Biol Chem 278:41624-30; Lavillette et al., 2005, Hepatology 41:265-74), but both effects are less striking than those obtained for CD81 and vary considerably between HCV genotypes (Lavillette et al., 2005, Hepatology 41:265-74) (and unpublished data). Recently, HCVpp infectivity was found to be enhanced significantly in the presence of HDL (Bartosch et al., 2005, J Virol 79:8217-29; Meunier et al., 2005, Proc Natl Acad Sci USA 102:4560-5; Voisset et al., 2005, J Biol Chem 280:7793-9). The enhancement depends on functional SR-BI on the target cell since both SR-BI siRNA and BLT-4, a drug that inhibits flux of cholesteryl esters from SR-BI bound HDL into the target cell membrane (Nieland, T.J., et al. 2002 Proc Natl Acad Sci USA 99:15422-7), completely abrogate the enhancing effect of HDL. These treatments have no (BLT-4) or variable (siRNA) effects on infectivity in the absence of HDL (Bartosch, B., et al. 2005 J Virol 79:8217-29; Voisset, C., et al. 2005 J Biol Chem 280:7793-9). Finally, it was found that oxidized LDL, an LDL-derived product of atherosclerotic processes and a known SR-BI ligand, dramatically inhibits HCVpp and HCVcc infectivity (Hahn, T., et al. 2006 Hepatology In Press). Based on these findings, it would appear that, in addition to CD81, SR-BI also has an important role in HCV entry. However, co-expression of CD81 and SR-BI is not sufficient to confer susceptibility to HCVpp (Bartosch, B., A., et al. J Biol Chem 278:41624-30; Hsu, M., J. et al. 2003. Proc. Natl. Acad. Sci. USA 100:7271-76), suggesting that additional factors are required.

The C-type lectins dendritic cell- and liver-specific intercellular adhesion molecule 3-grabbing nonintegrin (DC-SIGN and L-SIGN) binds E2 (Gardner et al., 2003, Proc Natl Acad Sci USA 100:4498-4503; Lozach et al., 2003, J Biol Chem 278:20358-66; Pohlmann et al., 2003, J Virol 77:4070-4080), HCVpp (Cormier et al., 2004, Proc Natl Acad Sci USA 101: 14067-72; Lozach et al., 2004, J Biol Chem 279:32035-45) and several other viruses (Alvarez et al., 2002, J Virol 76:6841; Geijtenbeek et al., 2000, Cell 100:587-97; Halary et al., 2002, Immunity 17:653-64; Tassaneetrithep et al., 2003, J Exp Med 197:823-9). The interaction between HCVpp and a cell expressing DC- or L-SIGN does not result in infection; however, bound HCVpp can be transmitted to permissive cells in co-culture (Cormier et al., 2004, Proc Natl Acad Sci USA 101:14067-7; Lozach et al., 2004, J Biol Chem 279: 32035-45), as is the case for HIV (Geijtenbeek et al., 2000, Cell 100:587-97). As L-SIGN and DC-SIGN are expressed on liver sinusoidal endothelial cells and DCs, respectively, a model where they capture and transmit HCV particles to susceptible hepatocytes is feasible but unproven. The association of HCV with lipoproteins (Monazahian et al., 2000, Med Microbiol Immunol (Berl) 188:177-84; Thomssen et al., 1992, Med. Microbiol. Immunol. 181:293-30) has led to the hypothesis that the low density lipoprotein receptor (LDL-R) may be involved in HCV entry. At least in the presence of plasma, LDL-R appears to mediate cell attachment and possibly cellular uptake of plasma derived HCV RNA (Agnello et al., 1999, Proc. Natl. Acad. Sci. USA 96:12766-12771; Monazahian et al., 1999, Journal of Medical Virology 57:223-9; Wunschmann et al., 2000, J Virol 74:10055-62). Whether this interaction results in productive infection, however, is uncertain, as HCVpp do not seem to require LDL-R for cell entry (Bartosch et al., 2003, J Exp Med 197:633-642; Hsu et al., 2003, Proc. Natl. Acad. Sci. USA 100:7271-76). Moreover, heparan sulfates (HS) (Barth, H., et al. 2003 J Biol Chem 278:41003-12) and asialoglycoprotein receptor (ASGP-R) (Saunier, B., et al. 2003 J Virol 77:546-59) have been suggested as HCV entry factors, but their roles have not been rigorously validated in an infection assay.

When HCVpp became available it was quickly noted that only a select group of cell lines, all of which were derived from human liver, could be infected (Bartosch et al., 2003, J Exp Med 197:633-642; Hsu et al., 2003, Proc. Natl. Acad. Sci. USA 100:7271-76; Zhang et al., 2004, J Virol 78:1448-55). What precisely defines this narrow tropism is as yet unclear. So far, no set of molecules sufficient to permit HCVpp entry into a target cell has been defined. Indeed, several cell lines express CD81, SR-BI and LDL-R at levels comparable to permissive cells and still cannot be infected (Hsu, M., et al. 2003 Proc. Natl. Acad. Sci. USA 100:7271-76). Thus one or more additional factor(s) essential for HCV entry are still missing.

In 1998, Furuse and colleagues identified CLDN1 and Claudin 2 (CLDN2) as integral membrane proteins present in the tight junctions of mouse hepatocytes that were able to reconstitute de novo tight junction (TJ) strands when expressed in mouse fibroblasts (Furuse, M., et al. 1998 J Biol 141:1539-50; Furuse, M., 1998 J Cell Biol 143:391-401). Subsequently, several homologous gene products were identified bringing the claudin gene family up to 24 members (Van Itallie, C. M., and J. M. Anderson. 2005. Claudins and Epithelial Paracellular Transport. Annu. Rev Physiol. for review). Claudins are small (20-27 kD) molecules with a short cytoplasmic N- and C-terminal tails. Four membrane-spanning helices are separated by a larger (~53aa) first and a smaller (~24aa) second extracellular loop (EL1 and EL2, respectively) and a very short intracellular loop (FIG. 3).

Claudins are thought to be the major structural component of the TJ in epithelia where claudin family members and other TJ associated membrane proteins such as occludin, the junction-adhesion-molecule (JAM) and the coxsackie-adenovirus-receptor (CAR) associate laterally to form the TJ strand (Furuse, M. et al. 1999 J Cell Biol 147:891-903; Gonzalez-Mariscal, L. et al. 2003 Prog Biophys Mol Biol 81:1-44). TJ strands in the membrane of neighboring cells then interact across the intercellular space to form the actual TJ. The extracellular loops of the claudins are thought to be central to these intercellular contacts that narrow and largely obliterate the intercellular space, thus forming the barrier between the apical and the basolateral side of the epithelium (Furuse, M., et al. 1999 J Cell Biol 147:891-903). Despite their name, TJs do not completely seal off the paracellular pathway but allow selective flux of solutes based on size and charge. Paracellular pathway selectivity seems to be determined largely by the extracellular domains of the claudins present in a given tight junction (Colegio, O.R., et al. 2003 Am J Physiol Cell Physiol 284:C1346-54; Furuse, M., et al. 2001. J Cell Biol 153:263-72). Thus, the modular claudin composition of the tight junction may determine both the transepithelial electrical resistance and the paracellular pathway selectivity for certain solutes in epithelial tissues. Finally, through their intracellular C-terminus, claudins interact with PDZ-domain containing adaptor proteins, such as the TJ associated proteins zonula occludens (ZO)-1, -2 and -384.

CLDN1 is expressed in a number of epithelia, with the highest levels detected in the liver followed by kidney, skin and other tissues (Furuse, M., et al. 1998 J Cell Biol 141: 1539-50; Su, A.I., et al. 2002 Natl Acad Sci USA 99:4465-70). Claudin-1 knockout mice die in the neonatal period due to water loss through the skin (Furuse, M., et al. 2002 J Cell Biol 156:1099-111). However, loss of CLDN1 is tolerated in humans; individuals homozygous for a two nucleotide deletion in the Claudin-1 gene resulting in frame shift and a premature stop codon have been found in two inbred families of Moroccan descent (Hadj-Rabia, S., et al. 2004 Gastroenterology 127:1386-90). Affected patients exhibit scaling skin (ichthyosis) and liver disease due to neonatal sclerosing cholangitis. Moreover, several other members of the claudin family have been implicated in genetic and infectious diseases: Claudin-14 mutations cause recessive non-syndromic deafness (Wilcox, E.R., et al. 2001 Cell 104:165-72) and this phenotype was replicated in Claudin-14 knockout mice (Ben-Yosef, T., et all. 2003 Hum Mol Genet 12:2049-61). Defects in Claudin-16 (Paracellin) result in renal magnesium loss in humans (Simon, D.B., et al. 1999 Science 285:103-6). The C-terminus of the *Clostridium perfringens* enterotoxin (CPE), a major cause of food poisoning, binds specifically to Claudin-3 and -4 causing disruption of intestinal TJs while the N-terminus forms pores in the plasma membrane leading to further disruption of epithelial integrity(Fujita, K., et al. 2000 FEBS Lett 476:258-61; Hanna, P.C. et al. 1992 Infect Immun 60:2110-4; Sonoda, N., et al. 1999 J Cell Biol 147: 195-204). As mentioned above and described in section C, we have evidence indicating that CLDN1 is a required entry factor for HCV. Interestingly, several other TJ molecules have been implicated in viral infection; CAR functions as a receptor for coxsackie- and adenoviruses (Bergelson, J.M., et al. 1997 Science 275:1320-3); JAM is an essential receptor for reoviruses (Barton, E.S., et al. 2001 Cell 104:441-51); and CLDN7 has been implicated in HIV entry into CD4 negative cells (Zheng, J., et al. 2005 Retrovirology 2:79). A recent elegant study expanded on this theme of TJ components in viral entry by showing that group B coxsackie virus initially engages a receptor, DAF, on the luminal surface of intestinal cells. DAF binding triggers signaling events that result in the migration of the virus-DAF complex to the TJ where an interaction with a co-receptor, CAR, occurs that then results in caveolin dependent uptake of the viral particle (Coyne, C.B., et al. 2006 Cell 124:119-31).

SUMMARY OF INVENTION

Our invention defines a new cellular factor required for HCV entry and probes its roles in the entry process. Using a powerful expression screen, CLDN1 (Claudin-1) was identified as a new factor required for HCV entry. We have determined the CLDN1 determinants necessary for entry, devised methods for screening for additional cellular molecules involved in the entry process, and provided assays to identify molecules that block HCV entry steps from virion binding to membrane fusion. This invention employs wide spectrum of reagents including soluble HCV glycoproteins, HIV-HCV pseudoparticles (i.e., HIV particles bearing HCV envelope proteins), cell culture infectious HCV, in vivo passaged cell culture infectious virus and target cell types, including primary human hepatocytes, are available for these studies. Identification of cellular molecules involved in HCV entry and understanding their function enables rational targeting of early steps in HCV infection and will ultimately contribute to the development of transgenic mice that support productive HCV infection as preclinical models for evaluation of new HCV therapies.

Using a recycling retrovirus expression cloning approach, Claudin-1 (CLDN1) was identified as an HCV entry factor. CLDN1 transduction of 293T cells expressing CD81 and SR-BI/II, renders these normally non-permissive cells fully permissive for HCVpp entry and HCVcc infection. CLDN1, a tight junction (TJ) constituent, is highly expressed in human liver and its expression correlates with HCV entry permissiveness in a variety of tissue culture cells. CLDN1 contains two extracellular loops, four membrane-spanning segments, short cytoplasmic N- and C-termini, and a small intracellular loop. In contrast to CLDN1, expression of the homologous family members CLDN3 and CLDN7 does not promote HCV entry.

This invention first provides methods of inhibiting, mitigating or preventing infection of a subject with Hepatitis C Virus (HCV) that comprise contacting a cell in said subject with an agent which inhibits HCV interaction with a Claudin-1 protein. The contacted cell can be a hepatocyte. The subject can be a mouse, a rat, a monkey, or a human. In certain embodiments of the method, the agent binds to extracellular loop 1 of the Claudin-1 protein. The agent is selected from the group consisting of an antibody, an aptamer, or a recombinant protein. When the agent is an antibody, the antibody can be a monoclonal or a single chain antibody.

The antibody can be a synthetic antibody. The variable region of the synthetic antibody that binds to extracellular loop 1 of the Claudin-1 protein can be obtained from a phage display, bacterial expression, or yeast expression library. The agent can also be a peptide or peptidomimetic compound that is structurally related to amino acid residues 28 to 49 of a Claudin-1 protein as shown in SEQ ID NO:1. The peptide or peptidomimetic compound used in the method can comprise amino acid residues 28 to 49 of a Claudin-1 protein as shown in SEQ ID NO:1, conservative amino acid substitutions thereof, or chemically derivatized variants thereof, wherein residue 32 is isoleucine and residue 48 is glutamic acid. In certain embodiments, residue 41 of said peptide or peptidomimetic compound is isoleucine. In other embodiments, residue 31 of said peptide or peptidomimetic compound is isoleucine and/or residue 33 is serine.

Also provided by the invention are transgenic animal models for the study of Hepatitis C Virus (HCV) infection, replication and pathogenesis that comprise expression of a human Claudin-1 transgene in the animal. The animal is selected from the group consisting of a mouse, a monkey, and a rat.

Methods of screening for an inhibitor of Hepatitis C Virus (HCV) infection that comprise screening a library for a compound which prevents or mitigates interaction of a region of a Hepatitis C Virus with a region of a Claudin-1 protein are also contemplated by this method. A method of identifying a compound or agent that prevents or mitigates interaction of a region of a Hepatitis C Virus with a region of a Claudin-1 protein can comprise the steps of: a) providing either i) a recombinant protein comprising at least amino acid residues 28 to 49 of a Claudin-1 protein as shown in SEQ ID NO:1 or conservative amino acid substitutions thereof, or ii) a cell comprising a recombinant vector that provides for expression of a membrane bound protein comprising at least amino acid residues 28 to 49 of a Claudin-1 protein as shown in SEQ ID NO:1 or conservative amino acid substitutions thereof, wherein said amino acid residues of said Claudin-1 protein are located extracellularly to said cell; b) contacting the protein or the cell from step (a) with an agent or a compound and an HCV envelope protein, a cell expressing HCV envelope proteins E1 and E2, an HCV pseudotyped retroviral particle, an HCV cell culture particle, an ex vivo HCV cell culture particle or HCV; and c) determining if the compound or agent inhibits interaction or fusion of said protein or said cell provided in (a) with said HCV envelope protein, said cell expressing HCV envelope proteins E1 and E2, said HCV pseudotyped retroviral particle, said HCV cell culture particle, said ex vivo HCV cell culture particle, or said HCV provided in step (b).

In these methods of identifying a compound or agent that prevents or mitigates interaction of a region of a Hepatitis C Virus with a region of a Claudin-1 protein, the recombinant protein or the cell in step (a) can comprise amino acid residues 28 to 81 of a Claudin 1 protein as shown in SEQ ID NO:1 or conservative amino acid substitutions thereof. Alternatively, the recombinant protein or cell in step (a) can comprise amino acid residues 1 to 102 of a Claudin-1 protein as shown in SEQ ID NO:1 or conservative amino acid substitutions thereof, a Claudin-1 protein, or a Claudin-1 protein that has an amino acid sequence as shown in SEQ ID NO:1 or conservative amino acid substitutions thereof. The recombinant protein in step (a) can be provided in a soluble form, in a liposome, or attached to a solid support. In certain embodiments, the recombinant protein in step (a) further comprises a detectable label. This detectable label can be selected from the group consisting of a radiolabel, a spectrophotometrically detectable label, a fluorescent label, a time-resolved fluorescence label, a hapten and an epitope.

In certain embodiments of these methods of identifying a compound or agent that prevents or mitigates interaction of a region of a Hepatitis C Virus with a region of a Claudin-1 protein, the cell in step (a) can be a CD81 positive cell. In other embodiments, the cell is an SR-BI positive cell. In still other embodiments, the cell in step (a) is a 293T or an SW 13 cell.

The agent in step (b) can be provided by an antibody library, an aptamer library, a peptide library, a recombinant protein library or a peptidomimetic library. When the agent is an antibody, the antibody library can be a phage display, bacterial expression, or yeast expression library. Compounds can be from a compound library.

Various recombinant vectors can be used in these methods of identifying a compound or agent that prevents or mitigates interaction of a region of a Hepatitis C Virus with a region of a Claudin-1 protein. The recombinant vector can be a DNA vector or an RNA vector. In certain embodiments, the recombinant vector comprises at least one sequence encoding a transmembrane domain that is operably linked to a sequence encoding at least amino acid residues 28 to 49 of a Claudin-1 protein as shown in SEQ ID NO:1 or conservative amino acid substitutions thereof. In still other embodiments, the recombinant vector comprises a first sequence encoding a signal peptide, wherein said sequence is operably linked to a sequence encoding at least amino acid residues 28 to 49 the amino acid residues of the Claudin-1 protein or conservative amino acid substitutions thereof. Recombinant vectors that comprise a sequence encoding a signal peptide can further comprise a second sequence encoding a domain that binds to a membrane bound protein, wherein this second sequence is operably linked to the first sequence encoding the signal peptide and to a sequence encoding at least amino acid residues 28 to 49 of a Claudin-1 protein as shown in SEQ ID NO:1 or conservative amino acid substitutions thereof. Recombinant vectors that comprise a sequence encoding a signal peptide can further comprise a second sequence encoding a domain that provides for interaction to a membrane, wherein this second sequence is operably linked to the first sequence encoding the signal peptide and to a sequence encoding at least amino acid residues 28 to 49 of a Claudin-1 protein as shown in SEQ ID NO:1.

A variety of methods can be used to determine if the compound or agent prevents or mitigates interaction of a region of a Hepatitis C Virus with a region of a Claudin-1 protein. In one embodiment of the method, inhibition of binding or interaction of the recombinant protein of step (a) is determined in step (c) by assaying for retention of the recombinant protein by a HCV envelope protein, by a cell expressing HCV envelope proteins E1 and E2, by a HCV pseudotyped retroviral particle, by a HCV cell culture particle, by an ex vivo HCV cell culture particle, or by an HCV provided in step (b), wherein decreased retention of the recombinant protein is indicative of binding inhibition. In other embodiments of the method, in particular those involving use of cells or virus particles, determination of interaction or fusion in step (c) is effected by assaying a reporter protein. This reporter protein can be selected from the group consisting of a fluorescent protein, an immunologically detectable protein or an enzyme.

Fluorescent proteins can be selected from the group consisting of a red fluorescent protein, a green fluorescent protein, or a yellow fluorescent protein. Reporter enzymes can be selected from the group consisting of a chloramphenicol acetyl transferase, a beta galactosidase, a beta glucuronidase, and an alkaline phosphatase. Other embodiments where a selectable maker gene is used are also contemplated. This selectable marker gene can be suitable for either dominant or negative selections. Selectable marker genes include, but are not limited to, zeocin resistance, neomycin, G418, DHFR, TK, or hygromycin resistance genes.

Compounds that prevent or mitigate interaction of a region of HCV with Claudin-1 are also provided. Compounds that prevent or mitigate interaction of a region of a Hepatitis C Virus with extracellular loop 1 of a Claudin-1 protein, wherein said compound is identified by the methods of the invention, are provided by this invention. Agents that prevent or mitigate interaction of a region of a Hepatitis C Virus with extracellular loop 1 of a Claudin-1 protein are also provided by this invention. These agents can be identified by the methods of the invention. The identified agent can be an antibody, an aptamer, a peptide, a peptidomimetic compound, or a recombinant protein. When the agent is antibody, it can be a synthetic antibody. The antibody can be a monoclonal or a single chain antibody. Other agents of the invention are peptide or peptidomimetic compounds comprising amino acid residues 28 to 49 of a Claudin-1 protein as shown in SEQ ID NO:1, conservative amino acid substitutions thereof, or a chemically derivatized variant thereof, wherein residue 32 is isoleucine and residue 48 is glutamic acid. The peptide or peptidomimetic compound agents can comprise any one or all of a residue 41 isoleucine, a residue 31 isoleucine, and a residue 33 serine of a Claudin-1 peptide sequence as shown in SEQ ID NO:1.

This invention also provides kits for identifying a compound or agent that prevents or mitigates interaction of a region of a Hepatitis C Virus with a region of a Claudin-1 protein. The kits comprise either i) a recombinant protein comprising at least amino acid residues 28 to 49 of a Claudin-1 protein as shown in SEQ ID NO:1 or conservative amino acid substitutions thereof; or ii) a recombinant vector that provides for expression of a membrane bound protein comprising at least amino acid residues 28 to 49 of a Claudin-1 protein as shown in SEQ ID NO:1 or conservative amino acid substitutions thereof, wherein said amino acid residues of said Claudin-1 protein are located extracellularly to a cell expressing said membrane bound protein, or a cell comprising said recombinant vector and instructions for using the kit to identify a compound or agent that prevents or mitigates interaction of a region of a Hepatitis C Virus with a region of a Claudin-1 protein. The kits can further comprise an HCV envelope protein, a recombinant vector encoding HCV envelope proteins E1 and E2, a recombinant vector encoding an HCV pseudotyped retroviral particle, a recombinant vector encoding an HCV cell culture particle, or a recombinant vector encoding an infectious HCV particle. Alternatively, the kit can contain a recombinant protein, a membrane bound protein provided by a vector or a membrane bound protein of a cell that comprises amino acid residues 28 to 81 or amino acid residues 1 to 102 of a Claudin 1 protein as shown in SEQ ID NO:1 or conservative amino acid substitutions thereof. In other embodiments, the kit can contain a recombinant protein, a membrane bound protein provided by a vector or a membrane bound protein of a cell that comprises a Claudin 1 protein or a Claudin 1 protein as shown in SEQ ID NO:1.

The invention further provides cell culture compositions that are useful for identifying compounds or agents that prevents or mitigates interaction of a region of a Hepatitis C Virus with a region of a Claudin-1 protein. Cell culture compositions of the invention comprise: i) a cell comprising a recombinant vector that provides for expression of a membrane bound protein comprising at least amino acid residues 28 to 49 of a Claudin-1 protein as shown in SEQ ID NO:1 or conservative amino acid substitutions thereof, wherein said amino acid residues of said Claudin-1 protein are located extracellularly to said cell, and either ii) a cell comprising a recombinant vector that encodes HCV envelope proteins E1 and E2 or iii) any one of an HCV pseudotyped retroviral particle, an HCV cell culture particle, an ex vivo HCV cell culture particle, or an HCV particle. In other embodiments of the invention, the recombinant vector of (i) provides for expression of a membrane bound protein comprising at least amino acids 28 to 81 or at least amino acids 1 to 102 of a Claudin-1 protein as shown in SEQ ID NO:1 or conservative amino acid substitutions thereof. Alternatively, the recombinant vector of (i) can provide for expression of a membrane bound protein comprising a Claudin-1 protein or for expression of a Claudin-1 protein as shown in SEQ NO:1 or conservative amino acid substitutions thereof. In the cell culture composition, the HCV pseudotyped retroviral vector can comprise an HCV E1 protein, an HCV E2 protein and a packaging competent retroviral genome containing a reporter gene. The packaging competent retroviral genome can be an HIV or an MLV packaging competent retroviral genome. Alternatively, the packaging competent retroviral genome is an envelope deficient retroviral genome. The recombinant vector of the cell culture composition can comprise at least one sequence encoding a transmembrane domain that is operably linked to a sequence encoding at least amino acid residues 28 to 49 of a Claudin-1 protein as shown in SEQ ID NO:1 or conservative amino acid substitutions thereof. In still other embodiments, the recombinant vector comprises a first sequence encoding a signal peptide, wherein said sequence is operably linked to a sequence encoding at least amino acid residues 28 to 49 the amino acid residues of the Claudin-1 protein or conservative amino acid substitutions thereof. Recombinant vectors that comprise a sequence encoding a signal peptide can further comprise a second sequence encoding a domain that binds to a membrane bound protein, wherein this second sequence is operably linked to the first sequence encoding the signal peptide and to a sequence encoding at least amino acid residues 28 to 49 of a Claudin-1 protein as shown in SEQ ID NO:1 or conservative amino acid substitutions thereof. Recombinant vectors that comprise a sequence encoding a signal peptide can further comprise a second sequence encoding a domain that provides for binding to a membrane, wherein this second sequence is operably linked to the first sequence encoding the signal peptide and to a sequence encoding at least amino acid residues 28 to 49 of a Claudin-1 protein as shown in SEQ ID NO:1 or conservative amino acid substitutions thereof.

The invention further provides for compositions that are useful for preventing entry of HCV into cells in a subject or in vitro. The composition of the invention comprises a non-naturally occurring agent or compound and a Claudin-1 protein, wherein the non-naturally occurring agent or compound is bound to extracellular loop 1 of said Claudin 1 protein and inhibits HCV entry. The composition can be obtained by administering the non-naturally occurring agent or compound to a subject selected from the group consisting of a mouse, a rat, a monkey, and a human. Alternatively, the composition can be obtained by contacting a cell comprising a recombinant vector that provides for expression of a membrane bound protein comprising at least amino acid residues 28 to 49 of a Claudin-1 protein as shown in SEQ ID NO:1 or conservative amino acid substitutions thereof, wherein the amino acid residues of said Claudin-1 protein are located extracellularly to a cell expressing said membrane bound protein, with the non-naturally occurring agent or compound. In still other embodiments, the composition is obtained by contacting a recombinant protein comprising at least amino acid residues 28 to 49 of a Claudin-1 protein as shown in SEQ ID NO:1 with the non-naturally occurring agent or compound. The non-naturally occurring agent can be an antibody, an aptamer, or a recombinant protein. The compound is a non-naturally occurring compound.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

Figure 1:
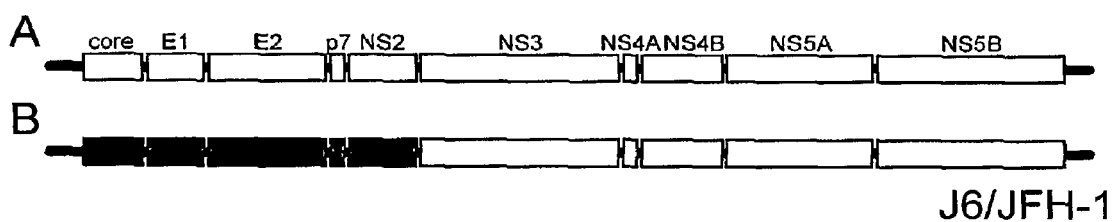
FIG. 1. HCV genome and HCVcc organization. (A) Schematic representation of HCV genomic RNA. The amino-terminal one third of the polyprotein, translated through the action of an IRES, encodes the HCV structural proteins, including the capsid protein, core, and the envelope glycoproteins E1 and E2. The remainder of the polyprotein encodes the p7 protein and the viral nonstructural proteins NS2, -3, -4A, -4B, -5A, and -5B. (B) Schematic of the infectious J6/JFH-1 full length chimeric RNA. The C-NS2 region, represented in dark boxes, is derived from the HCJ6 isolate, while the remainder of the genome is from JFH-1.

din-1 required for HCV entry, "a Claudin-1 protein" is any protein that comprises the amino acid residues of Claudin-1 extracellular loop 1 that provide for HCV entry and additional sequences that provide for extracellular presentation of the amino acid residues of Claudin-1 extracellular loop 1.

As used herein, the term "HCV" refers to any major HCV genotype, subtype, isolate, and/or quasispecie. HCV genotypes include, but are not limited to, genotypes 1, 2, 3, 4, 5 and 6 and HCV subtypes include, but are not limited to, subtypes 1a, 1b, 2a, 2b, 2c, 3a, 4a-4f, 5a and 6a.

As used herein, an "endogenous Claudin-1 protein" comprises the protein of SEQ ID NO:1 (NCBI Accession Number NP_066924) and any naturally occurring variants commonly found in HCV permissive subject populations.

As used herein, the phrase "conservative amino acid substitutions" refers to one or more changes in amino acids in a sequence is (are) that are replaced with another amino acid(s), the charge and polarity of which is similar to that of the native amino acid. Conservative substitutes for an amino acid within a protein, a peptide, or peptidomimetic compound are made with members of the group to which the originally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine. Conservative amino acid changes can be made by substituting one amino acid within one of these groups with another amino acid within the same group.

As used herein, an "antibody" is any of a polyclonal antibody, a monoclonal antibody, a single chain antibody, or a synthetic antibody As used herein, a "monoclonal antibody" is any antibody derived from any source that recognizes a single epitope.

As used herein, a "single chain antibody" is any light chain antibody, any heavy chain antibody, or any fragment thereof comprising an antigen recognition site. Single chain antibodies can be derived from any source.

As used herein, a "synthetic" antibody is any antibody that is produced by recombinant DNA technology. Synthetic antibodies thus include, but are not limited to, humanized antibodies, mutagenized antibodies, and antibodies derived from human, bacterial, yeast or bacteriophage expression libraries.

As used herein, the phrase "peptidomimetic compound" refers a peptide analog containing one or more non-naturally occurring amino acids (e.g., non-natural side chains, non-natural chiralities, N-substituted amino acids, or beta amino acids), non-natural topologies (e.g., cyclic or branched) and/or peptide analogues with partially or totally substituted amide (peptide) bonds with ester, thioester or other linkages.

As used herein, the phrase "chemically derivatized variant", when used in reference to a peptide or peptidomimetic compound, refers to peptides or peptidomimetic compounds that have been covalently modified. Covalent modifications include, but are not limited to, acetylation, amidation, sulfation, succinylation, methylation, chelator linkage or terminal blockage.

As used herein, the term "corresponding", when used in the context of comparing, aligning, or identifying equivalent amino acids in one polypeptide sequence with another polypeptide, peptide, or peptidomimetic compound sequence, refers to the comparison or alignment that will yield the highest percent identity when aligned with the other polypeptide sequence. For example, in an alignment of SEQ ID NO:1 with a peptide comprising residues 28 to 41 of SEQ ID NO:1, residue 1 of that peptide would correspond to residue 28 of SEQ ID NO:1 and so on.

As used herein, the phrase "membrane bound protein" refers to any protein that is bound to a cell membrane under physiological pH and salt concentrations. Binding of the membrane bound protein can be either by direct binding to the phospholipid bilayer of by binding to a protein, glycoprotein, or other intermediary that is bound to the membrane.

As used herein, the term "extracellular" refers to the external, non-cytoplasmic region of a cell.

As used herein, the phrase "interaction of a region of a Hepatitis C Virus with a region of a Claudin-1 protein", encompasses any step in the process by which an HCV virion or component derived therefrom is recognized, bound and/or internalized by a cell. As used herein, interactions include any direct or indirect function of Claudin-1 required for HCV entry.

To the extent to which any of the preceding definitions is inconsistent with definitions provided in any patent or non-patent reference incorporated herein or in any reference found elsewhere, it is understood that the preceding definition will be used herein.

Methods of Inhibiting, Mitigating or Preventing HCV Infection by Inhibiting Hcv Interaction with a Claudin-1 Protein A variety of methods for inhibiting HCV infection by inhibiting endogenous Claudin-1 function are contemplated by this invention. Such methods can comprise either blockage of regions of endogenous Claudin-1 that provide for cellular interactions required for HCV entry or blockage of the regions of HCV that provide for interactions with endogenous Claudin-1 or a Claudin-1 containing protein complex. Provided herein is the identification of the Claudin-1 extracellular loop 1 region and specific amino acid residues within extracellular loop 1 which are key elements required for HCV entry. The identification of extracellular loop 1 as a key cellular factor involved in HCV entry into a cell provides for both blockage of endogenous Claudin-1 regions and blockage of HCV regions to inhibit HCV infection. However, since endogenous Claudin-1 extracellular loop 1 (EL1) and extracellular loop 2 (EL2) are likely in close proximity to and perhaps interacting with each other in the endogenous Claudin-1 protein, it is also contemplated that the binding of inhibitors to extracellular loop 2 may also interfere with HCV infection, either through direct or indirect effects. Furthermore, those skilled in the art will appreciate that agents or compounds that interact with regions of Claudin-1 other than either extracellular loop 1 or extracellular loop 2 can also disrupt Claudin-1 function and provide for prevention, inhibition, or mitigation of HCV infection.

Blockage of Claudin-1 extracellular loop 1 interactions with HCV can be effected by binding of an agent to any region within an endogenous Claudin-1 extracellular loop 1 or by binding of an agent that binds elsewhere but alters the structure of Claudin-1 extracellular loop 1 such that it no longer functions in HCV entry. When present in a subject, endogenous Claudin-1 is understood herein to comprise the protein of SEQ ID NO:1 (NCBI Accession Number NP_066924) and any naturally occurring variants commonly found in HCV permissive subject populations. Extracellular loop-1 of endogenous Claudin 1 comprises amino acid residues 28 to 81 of a Claudin-1 protein as shown in SEQ ID NO:1 and any naturally occurring variants commonly found in HCV permissive subject populations when found in a subject. In experimental systems, binding of an antibody to a sequence that is immediately adjacent to Claudin-1 extracellular loop 1 is shown herein to be sufficient to block the ability of a Claudin-1 protein to function in entry of HCVpp. Without seeking to be limited by theory, binding of the agent to Claudin-1 extracellular loop 1 is believed to sterically inhibit productive interactions of Claudin-1 that permit cellular entry of HCV and HCV infection. When a large agent such as an antibody or recombinant protein is used to bind Claudin-1 extracellular loop 1 and inhibit HCV infection, any region of the Claudin-1 extracellular loop 1 can be bound by the agent. However, it is anticipated that smaller agents may need to bind specific regions of the Claudin-1 extracellular loop 1 region to inhibit HCV infection. In these instances, binding to residues 28 to 49 of an endogenous Claudin-1 protein as shown in SEQ ID NO:1 can inhibit HCV infection. In other embodiments, interaction of the agent with amino acid residues 32 is (isoleucine) and 48 (glutamic acid) of an endogenous Claudin-1 protein as shown in SEQ ID NO:1 can block HCV infection.

Having identified the region of an endogenous Claudin-1 that can be bound to inhibit HCV infection, a variety of effective extracellular loop 1 binding agents are contemplated herein. In addition to antibodies, aptamers that bind to Claudin-1 extracellular loop 1 can be used to inhibit HCV infection. As used herein, an aptamers can comprise any DNA, RNA, oligonucleotide, or chemically modified oligonucleotide that binds to a target. Isolation and identification of aptamers has been disclosed (U.S. Pat. No. 5,582,981, U.S. Pat. No. 6,867,289, U.S. Pat. No. 7,179,894). Alternatively, recombinant binding proteins that bind an endogenous Claudin-1 extracellular loop 1 can be used to inhibit HCV infection. As used herein, "recombinant binding proteins" are any non-naturally occurring proteins obtained by recombinant DNA or polymerase chain reaction-mediated reactions that bind to a target. Recombinant binding proteins can comprise polypeptide binding regions of immunoglobulin heavy chains variable domains, immunoglobulin light chain variable domains, V.alpha./V.beta. domains of T cell receptor proteins, or combinations thereof. Isolation and identification of recombinant binding proteins has been disclosed (U.S. Pat. No. 6,010,884 and U.S. Pat. No. 6,297,053).

Blockage of HCV regions to inhibit HCV infection can also be effected by agents that mimic the region of Claudin-1 extracellular loop 1 that interacts with HCV. Without seeking to be limited by theory, contacting HCV with agents that mimic the critical region of Claudin-1 extracellular loop 1 is expected to inhibit productive interactions of HCV with endogenous Claudin-1 that permit cellular entry of HCV and HCV infection. These agents are expected to competitively inhibit interactions with HCV and endogenous Claudin-1 EL-1. One advantage of Claudin-1 extracellular loop 1 mimicking agents is that they can be optimized such that their interactions with the critical regions of HCV are potentiated while their interactions with any other endogenous cellular ligands that recognize endogenous Claudin-1 extracellular loop-1 (EL1) are minimized. Optimization of Claudin-1 mimicking agents is expected to provide for inhibition, prevention or mitigation of HCV infection while minimizing undesirable side effects.

Claudin-1 mimicking agents can comprise a peptide or peptidomimetic compound that comprise or are derived from amino acid residues 28 to 49 of a Claudin-1 protein as shown in SEQ ID NO:1. A key feature of such a peptide or peptidomimetic compound is the conservation of amino acids corresponding to residue 32 as isoleucine and to residue 48 as glutamic acid. It is anticipated that other residues in regions corresponding to amino acid residues 28 to 49 of a Claudin-1 protein can be substituted by conservative amino acids in the mimicking agents. Such conservative amino acid substitutions in mimicking agents can be tested for result effective inhibition of HCV interactions with Claudin 1 with any of the in vitro or cell-based assay methods provided herein. A variety of conservative amino acid substitutions can be made to obtain an effective mimicking agent. Mimicking agents include, but are not limited to, peptides or peptidomimetics where the valine at corresponding residue 41 can be conservatively substituted with other hydrophobic amino acids including, but not limited to, isoleucine. It is also contemplated that the arginine at residue 31 can be substituted by a glutamine and that the tyrosine at residue 33 can be substituted by a serine.

The use of various peptidomimetic compounds or chemical derivatives that comprise amino acid residues 28 to 49 of a Claudin-1 protein to antagonize or otherwise inhibit interactions of HCV with endogenous Claudin-1 in a subject is also contemplated. It is anticipated that such peptidomimetics or chemical derivatives can confer pharmaceutically useful properties such as increased stability and/or specificity on the peptide, peptidomimetic compound or chemical derivative. The use of peptidomimetic compounds derived from Claudin-1 amino acid residues 28 to 49 containing one or more non-naturally occurring amino acids (e.g., non-natural side chains, non-natural chiralities, N-substituted amino acids, or beta amino acids), non-natural topologies (e.g., cyclic or branched) and/or peptide analogues with partially or totally substituted amide (peptide) bonds with ester, thioester or other linkages is contemplated. It is also contemplated that peptidomimetic compounds comprising any of residues 29-49, 30-49, 31-49, and 32-49 or residues 29-48, 30-48, 31-48, or 32-48 of amino acid residues 28 to 49 of a Claudin-1 protein can be used to antagonize or otherwise inhibit interactions of HCV with endogenous Claudin-1. Chemical modifications to amino acid residues 28 to 49 of a Claudin-1 protein can comprise any covalent modification that does not inhibit the capacity of that peptide or derived peptidomimetic to interact with HCV. Covalent modifications contemplated include, but are not limited to, acetylation, amidation, sulfation, succinylation, methylation, chelator linkage or terminal blockage. Certain chemical modifications of peptides are described in U.S. Pat. No. 6,881,719 and U.S. Pat. No. 6,143,932. It is also contemplated that chemical derivatives of peptides comprising any of residues 29-49, 30-49, 31-49, and 32-49 or residues 29-48, 30-48, 31-48, or 32-48 of amino acid residues 28 to 49 of a Claudin-1 protein can be used to antagonize or otherwise inhibit interactions of HCV with endogenous Claudin-1. Peptidomimetic mimics of the EL-1 region can be obtained by peptidomimetic library screening methods such as those disclosed in U.S. Pat. No. 5,962,736. In preferred methods, the peptidomimetic library would be focused on the relevant amino acid residues of a Claudin-1 protein as described immediately above (i.e., peptidomimetics comprising any of residues 29-49, 30-49, 31-49, and 32-49 or residues 29-48, 30-48, 31-48, or 32-48 of amino acid residues 28 to 49 of a Claudin-1 protein). Other methods that can be used to obtain peptidomimetics are rational design methods such as those described in U.S. Pat. No. 5,947,847 or U.S. Pat. No. 5,331,573.

In practicing any of the above referenced methods involving administration of HCV inhibitory, preventative or mitigating agents to a subject, it is contemplated that a variety of pharmaceutical compositions comprising these active agents can be administered by a variety of techniques. Such pharmaceutical compositions may be formulated in various ways known in the art for administration purposes. To prepare the pharmaceutical compositions of the present invention, an effective amount of the particular compound, in base or acid salt form, as the active ingredient is combined with one or more pharmaceutically acceptable carriers and delivery vehicles. Numerous pharmaceutically acceptable carriers and delivery vehicles exist that are readily accessible and well known in the art, which may be employed to generate the preparation desired (i.e., that permit administration of the pharmaceutical composition orally, topically, rectally, percutaneously, by parenteral injection, intranasally or by inhalation). Representative examples of pharmaceutically acceptable carriers and delivery vehicles include aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene, polyoxypropylene-block polymers, polyethylene glycol and wool fat, and the like. The pharmacologic compositions described herein may further be prepared in unitary dosage form suitable for administration orally, percutaneously, by parenteral injection (including subcutaneous, intramuscular, intravenous and intradermal), topically, intranasally, by inhalation, or for application to a medical device, such as an implant, catheter, or other device. In preparing the compositions that permit administration of an oral dosage, for example, any of the pharmaceutically acceptable carriers known in the art may be used, such as water, glycols, oils, alcohols and the like in the case of carriers that permit oral delivery of liquid preparations such as suspensions, syrups, elixirs and solutions. When solid pharmaceutically acceptable carriers are desired that permit oral or rectal administration, starches, sugars, kaolin, lubricants, binders, cellulose and its derivatives, and disintegrating agents and the like may be used to prepare, for example, powders, pills, capsules and tablets. For pharmaceutically acceptable carriers that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient.

Methods of Identifying Compounds or Agents that Interfere with the Ability of Claudin-1 to Function in HCV Entry A variety of in vitro and cell based assays that provide for identification of compounds or agents that inhibit interactions of HCV with Claudin-1 are contemplated herein. Inhibition of HCV interactions with Claudin-1 can be used to inhibit, mitigate or prevent infection of a subject with any major HCV genotype, subtype, isolate, and/or quasispecie. HCV genotypes include, but are not limited to, genotypes 1, 2, 3, 4, 5 and 6 and HCV subtypes include, but are not limited to, subtypes 1a, 1b, 2a, 2b, 2c, 3a, 4a-4f, 5a and 6a. Furthermore, those skilled in the art will appreciate that agents or compounds that interact with any region of Claudin-1 can disrupt Claudin-1 functions that provide for HCV entry.

In vitro assays comprise any assay wherein binding, interaction or association of a recombinant Claudin-1 protein with HCV or components of HCV is determined. It is understood that the binding of recombinant Claudin-1 with HCV or components of HCV can be either direct or indirect. Indirect binding would entail binding of Claudin-1 to HCV through an intermediary. A recombinant Claudin 1 protein, as used in this context of an in vitro assay, refers to any protein comprising at least amino acid residues 28 to 49 of a Claudin-1 protein as shown in SEQ ID NO:1 or conservative amino acid substitutions thereof. Alternatively, the recombinant Claudin-1 protein used can comprise amino acids 28 to 81 or amino acids 1 to 102 of a Claudin-1 protein as shown in SEQ ID NO:1, amino acids 28 to 102 of a Claudin-1 protein as shown in SEQ ID NO:1, amino acids 1-102 or amino acids 28 to 102 and any number of additional Claudin-1 amino acid residues between 102 and 211, a Claudin-1 protein of SEQ ID NO:1, derivatives of any of the foregoing proteins wherein conservative amino acid substitutions have been made, or derivatives of any of the foregoing proteins wherein insertions or deletions that do not affect the capacity of the protein to interact with HCV have been made. Recombinant Claudin-1 protein can be used in the in vitro binding or interaction assays in either a soluble form or in insoluble forms such as liposomes. Still other recombinant Claudin-1 proteins can comprise or be derived from the murine Claudin-1 (SEQ ID NO:2), Claudin-1/Claudin-7 chimeras, or Claudin-7 proteins wherein residues corresponding to residues 32 and 48 of the Claudin-7 protein are substituted with the corresponding amino acid residues found in Claudin-1 (i.e., wherein residue 32 is isoleucine and residue 48 is glutamic acid). Claudin-7 is provided herein as SEQ ID NO:3. Other insoluble forms that can be used in binding assays include forms where the recombinant Claudin-1 protein is coupled to a solid support. Solid supports include beads, microtiter plates, column matrices, or any other materials suitable for immobilizing proteins for binding assays. Soluble forms of the recombinant Claudin-1 can further comprise sequences that facilitate solubility, detection and/or retention. Sequences that can facilitate solubility include, but are not limited to, sequences from glutathione-S-transferases or *E. coli* maltose binding proteins. Sequences that facilitate detection include any reporter protein, any epitope or any protein-binding domain. Those skilled in the art will appreciate that any of the foregoing sequences that promote solubility or detection can also facilitate retention. Retention is typically used in binding assays to associate the protein or protein ligand to a solid support. The recombinant protein can also further comprise additional sequences for retention such as FLAG™ epitopes (Stratagene, La Jolla, Calif., USA), myc epitopes, histidine tags and the like.

Binding or interaction of the recombinant Claudin-1 protein to any HCV or HCV derived material such as HCV, HCVcc, HCVpp, semi-purified HCV components, purified HCV proteins or recombinant HCV protein(s) can be determined in the methods contemplated herein. Binding or interaction of recombinant Claudin-1 to HCV E1 and E2 proteins is specifically contemplated. Such binding may be either direct or indirect. Either the recombinant Claudin-1 or the HCV or HCV derived materials can be detectably labeled to facilitate the binding assay. In certain embodiments, the recombinant Claudin-1 and the HCV or HCV derived materials are labeled with distinct detectable labels permitting simultaneous detection of each. In binding assays, the recombinant Claudin-1 protein is typically contacted by the HCV or HCV derived material, subjected to some form of buffer exchange, and binding determined. Binding may be determined by any suitable technique or combination of techniques, including but not limited to, detection of a bound label, surface plasmon resonance, or scintillation proximity assays.

Also contemplated are various cell based assays where a recombinant Claudin-1 protein is a membrane bound protein comprising at least amino acid residues 28 to 49 of a Claudin-1 protein as shown in SEQ ID NO:1 or conservative amino acid substitutions thereof such that the Claudin-1 amino acid residues 28 to 49 are extracellularly located. Alternatively, the recombinant, membrane bound protein that provides for extracellular presentation of at least amino acid residues 28 to 49 of a Claudin-1 protein used can comprise amino acids 28 to 81 or amino acids 1 to 102 of a Claudin-1 protein as shown in SEQ ID NO:1, amino acids 28 to 102 of a Claudin-1 protein as shown in SEQ ID NO:1, amino acids 1-102 or amino acids 28 to 102 and any number of additional Claudin-1 amino acid residues between 102 and 211, a Claudin-1 protein of SEQ ID NO:1, derivatives of any of the foregoing proteins wherein conservative amino acid substitutions have been made, or derivatives of any of the foregoing proteins wherein insertions or deletions that do not affect the capacity of the protein to interact with HCV have been made. Still other recombinant, membrane bound Claudin-1 proteins can comprise or be derived from the murine Claudin-1 (SEQ ID NO:2), Claudin-1/Claudin-7 chimeras, or Claudin-7 proteins wherein residues corresponding to residues 32 and 48 of the Claudin-7 protein are substituted with the corresponding amino acid residues found in Claudin-1 (i.e., wherein residue 32 is isoleucine and residue 48 is glutamic acid). Claudin-7 is provided herein as SEQ ID NO:3. Membrane bound forms of any of the foregoing proteins can be obtained by any method. The Claudin-1 residues and transmembrane domains located between amino acids 1-27 and residues 82-102 can provide for membrane bound, for extracellular presentation of any of the foregoing recombinant Claudin-1 protein. Alternatively, a signal peptide encoding sequence can be operably linked to at least amino acid residues 28 to 49 of a Claudin-1 protein to provide for extracellular localization of that sequence. Operable linkage of the signal peptide sequence would typically be to the N-terminus of the Claudin-1 amino acid sequences. When a signal peptide is used to provide for extracellular localization of the Claudin-1 amino acid sequence, membrane binding functionalities can be provided by a variety of sequences. In the signal peptide mediated extracellular localization methods, the membrane binding functionality can be provided by any combination of transmembrane domains (located C-terminal to the Claudin-1 amino acid sequences), domains that bind to extracellularly located protein or glycosylated domains of other transmembrane proteins, or domains that provide for post-translational modifications that result in membrane binding. Alternatively, the Claudin-1 amino acid sequences can be imbedded in an extracellular domain of another membrane bound protein to provide for presentation of the Claudin-1 sequences. Those skilled in the art will recognize that the method by which the Claudin-1 sequences are presented on the extracellular surface of the cell is not critical, so long as those sequences are presented in a manner that permits HCV interaction.

In certain embodiments of the method, the cell expressing the recombinant, membrane bound extracellular Claudin-1 amino acid residues is contacted by any of an HCV envelope protein, a cell expressing HCV envelope proteins E1 and E2, an HCV pseudotyped retroviral particle, an HCVcc particle, an ex vivo HCVcc particle or HCV. When the cell expressing the recombinant Claudin-1 is contacted by an HCV envelope protein(s), one can determine if binding of the envelope protein(s) is inhibited by a compound or agent by monitoring the presence or absence of the envelope protein following a buffer exchange. Such binding analyses are facilitated by providing detectably labelled envelope proteins. Binding of cells expressing envelope proteins, HCVpp, HCVcc, ex vivo HCVcc, or HCV to the cell expressing the recombinant Claudin-1 can also be monitored in the manner described for binding of envelope proteins. Infection by HCVpp or HCVcc can also be monitored by the use of reporter genes encoded by these species, which can be assayed for in cells following exposure to the agents or compounds.

The use of recombinant Claudin-1 proteins in in vitro assays that model other aspects of Claudin-1-mediated HCV entry into cells is also contemplated. Such assays would involve use of biochemical fractions from HCV, HCVcc, ex vivo HCV, HCVpp, recombinant cells expressing HCV envelope protein(s), reconstituted liposomes containing HCV components and other fractions or reconstituted materials derived from recombinant Claudin-1 expressing cells.

Interactions of HCV with Claudin-1 that result in entry of HCV into the cell can also be assayed to identify compounds or agents that interfere with any aspect of that process. Productive interaction or fusion of cells expressing envelope proteins, HCVpp, HCVcc, ex vivo HCVcc, or HCV to the cell expressing the recombinant Claudin-1 can also be assayed by techniques that monitor transfer of proteins or nucleic acids from the cells expressing envelope proteins, HCVpp, HCVcc, ex vivo HCVcc, or HCV to the cell expressing the recombinant Claudin-1. In certain embodiments, transfer of a reporter gene is monitored. When the reporter is transferred from HCVpp or any other suitable viral vector, the reporter will be expressed only upon entry into the cell expressing the recombinant Claudin-1 protein. When the reporter is present in a distinct cell that fuses to the cell expressing the recombinant Claudin-1 protein, the reporter gene will only be expressed when the cells fuse and the reporter is exposed to a factor in the cell expressing the recombinant Claudin-1 protein. Methods that provide for expression of a reporter upon cell fusion include, but are not limited to, operable linkage of the reporter to a promoter that is regulated by a trans-acting transcription factor present in the host cell. Entry of HCV, HCVcc, or ex vivo HCVcc can also be determined by any hybridization or polymerase-chain reaction based method for measuring the associated HCV RNA. Entry of replication-competent HCV RNA into cells that permit HCV RNA replication results in a substantial signal amplification due to HCV RNA replication. When quantitating HCV RNA by use of a quantitative reverse-transcriptase Polymerase Chain Reaction (qRT-PCR), the HCV-derived PCR product can be detected by use of any labelled polynucleotide probes, by use of an intercalating dye such as ethidium bromide or SYBR green, use of a hybridization probe containing a fluorophore and a quencher such that emission from the fluorophore is only detected when the fluorophore is released by the 5' nuclease activity of the polymerase used in the PCR reaction (i.e., a TaqMan™ reaction; Applied Biosystems, Foster City, Calif.) or use of methods where the fluorophore and quencher are displaced by polymerase mediated synthesis of the complementary strand (i.e., Scorpion™ or Molecular Beacon™ probes). Various methods for conducting qRT-PCR analysis to quantitate mRNA levels are well characterized (Bustin, S. A.; Journal of Molecular Endocrinology 29, 23, 2002). Fluorescent probes that are activated by the action of enzymes that recognize mismatched nucleic acid complexes (i.e., Invader™, Third Wave, Technologies, Madison, Wis.) can also be used to quantitate RNA. Those skilled in the art will also understand that RNA quantitation techniques such as Quantitative Nucleic Acid Sequence Based Amplification (Q-NASBA™) can be used to quantitate TIC807 protein-encoding mRNA and identify expressing plants. Commercially available kits for quantitating HCV RNA include the COBAS™ TaqMan HCV Test (TaqMan HCV; Roche Molecular Systems Inc., Branchburg, N.J.). HCVcc that comprise reporter genes are also available, thus allowing the quantification of infection following challenge similarly to the methods described for HCVpp.

To identify agents that inhibit interactions of HCV regions with Claudin-1, a variety of different libraries can be queried. Bacteriophage libraries comprising phage vectors that display antibody antigen recognition regions are one potential source of Claudin-1 recognition agents and have been described in U.S. Pat. No. 6,265,150. Methods for generating libraries of antigen-combining proteins of high diversity are described in U.S. Pat. No. 5,780,225 and U.S. Pat. No. 6,303,313. Methods of using libraries to obtain antigen recognition regions are also described in U.S. Pat. No. 5,395,750. Methods of obtaining a nucleic acid encoding a binding protein having a proteinaceous binding domain that binds a predetermined target material are described in U.S. Pat. No. 5,223,409. Yeast antibody display libraries can also be used to obtain antigen recognition regions and as described in U.S. Pat. No. 6,300,065. Those skilled in the art will recognize that such antigen recognition sequences can subsequently be isolated from the recombinant phage, bacterial or yeast vector and reengineered into a synthetic antibody appropriate for use in subjects. Reengineering of these recognition domains into humanized antibodies is particularly contemplated.

Kits for Identifying Compounds or Agent that Prevent or Mitigate Interaction of a Region of a Hepatitis C Virus with a Region of a Claudin-1 Protein In the particular embodiments contemplated herein, the methods and kits detect interactions of a region of HCV with a Claudin-1 protein. A kit may contain any of: i) a recombinant protein comprising at least amino acid residues 28 to 49 of a Claudin-1 protein as shown in SEQ ID NO:1 or conservative amino acid substitutions thereof, or ii) a recombinant vector that provides for expression of a membrane bound protein comprising at least amino acid residues 28 to 49 of a Claudin-1 protein as shown in SEQ ID NO:1 or conservative amino acid substitutions thereof, wherein said amino acid residues of said Claudin-1 protein are located extracellularly to a cell expressing said membrane bound protein, or iii) a cell comprising said recombinant vector and instructions for using the kit. The kit may also contain reagent(s) for detecting an interaction between a sample comprising HCV, HCVcc, HCVpp, HCV envelope proteins and the aforementioned recombinant proteins, vectors or cells comprising a Claudin-1 protein. The provided reagent(s) can be radio-, spectrophotometrically-, fluorescently- or enzymatically-labeled. The provided reagents can also be detectably labelled by other materials. The provided reagents may include a substrate that is converted to a product that can be detected by spectrophotometry, luminometry, or fluorescence. The kit can contain a known radiolabeled or hapten-labeled agent capable of binding or interacting with an antibody of the present invention.

The reagent(s) of the kit may be provided as a liquid solution, attached or otherwise deposited in or on a solid support or as a dried powder. Preferably, when the reagent(s) are provided in a liquid solution, the liquid solution is an aqueous solution. Preferably, when the reagent(s) provided are attached to, or otherwise deposited on a solid support, the solid support can be chromatography media, a test plate having a plurality of wells, or a microscope slide. When the reagent(s) provided are a dry powder, the powder can be reconstituted by the addition of a suitable solvent, that may be provided.

The container will generally include a vial into which the recombinant protein, recombinant vector, cells or detection reagent may be placed, and preferably suitably aliquoted. The kits of the present invention will also typically include a means for containing the recombinant protein, recombinant vector and/or cells in a container in close confinement for commercial sale. Such containers may include injection or blow-molded plastic containers into which the desired vials are retained.

However, it is also contemplated that such kits may be assembled not for commercial sale, but for internal use within a research group. Thus the usefulness of such kits is not restricted to commercial sales. The instructions for the kit may either be enclosed in the kit or provided by way of reference to a external or internal website or other internal or external document or reference. The reference may include, but is not limited to, this patent application or Evans et al., Nature. 2007; 446(7137):801-5 and associated supplementary information and data provided by Evans et al.

Cell Culture Compositions

The methods of the invention provide for useful cell culture compositions. These cell culture composition comprise: i) a cell comprising a recombinant vector that provides for expression of a membrane bound protein comprising at least amino acid residues 28 to 49 of a Claudin-1 protein as shown in SEQ ID NO:1 or conservative amino acid substitutions thereof, wherein said amino acid residues of said Claudin-1 protein are located extracellularly to said cell, and either ii) a cell comprising a recombinant vector that encodes HCV envelope proteins E1 and E2 or iii) any one of a HCV pseudotyped retroviral particle, a HCV cell culture particle, an ex vivo HCV cell culture particle, or an HCV particle. Such cell culture compositions can be used to determine if an added compound or agent can inhibit, mitigate, or prevent HCV interactions with Claudin-1. Compounds or agents identified by the use of the cell culture compositions can be used to prevent, inhibit or mitigate HCV infection in a subject.

Compositions Comprising Non-Naturally Occurring Agents or Compounds Bound to Extracellular Loop 1 of Claudin-1

Compositions comprising a non-naturally occurring agent or compound bound to extracellular loop 1 of a Claudin-1 protein are also provided herein. Such compositions can occur in a subject when the non-naturally occurring agent or non-naturally occurring compound is administered to the subject and are useful as they prevent, inhibit or mitigate HCV infection of the subject. Such compositions can also occur in the cell culture compositions of the invention when a non-naturally occurring agent or non-naturally occurring compound is added to the cell culture composition and are useful as they serve to identify the non-naturally occurring agent or compound for preventing, inhibiting or mitigating HCV infection of the subject.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

EXAMPLES

The following disclosed embodiments are merely representative of the invention, which may be embodied in various forms. Thus, specific structural and functional details disclosed herein are not to be interpreted as limiting.

Example 1

Identification of CLDN-1 as an Entry Factor

Figure 2:
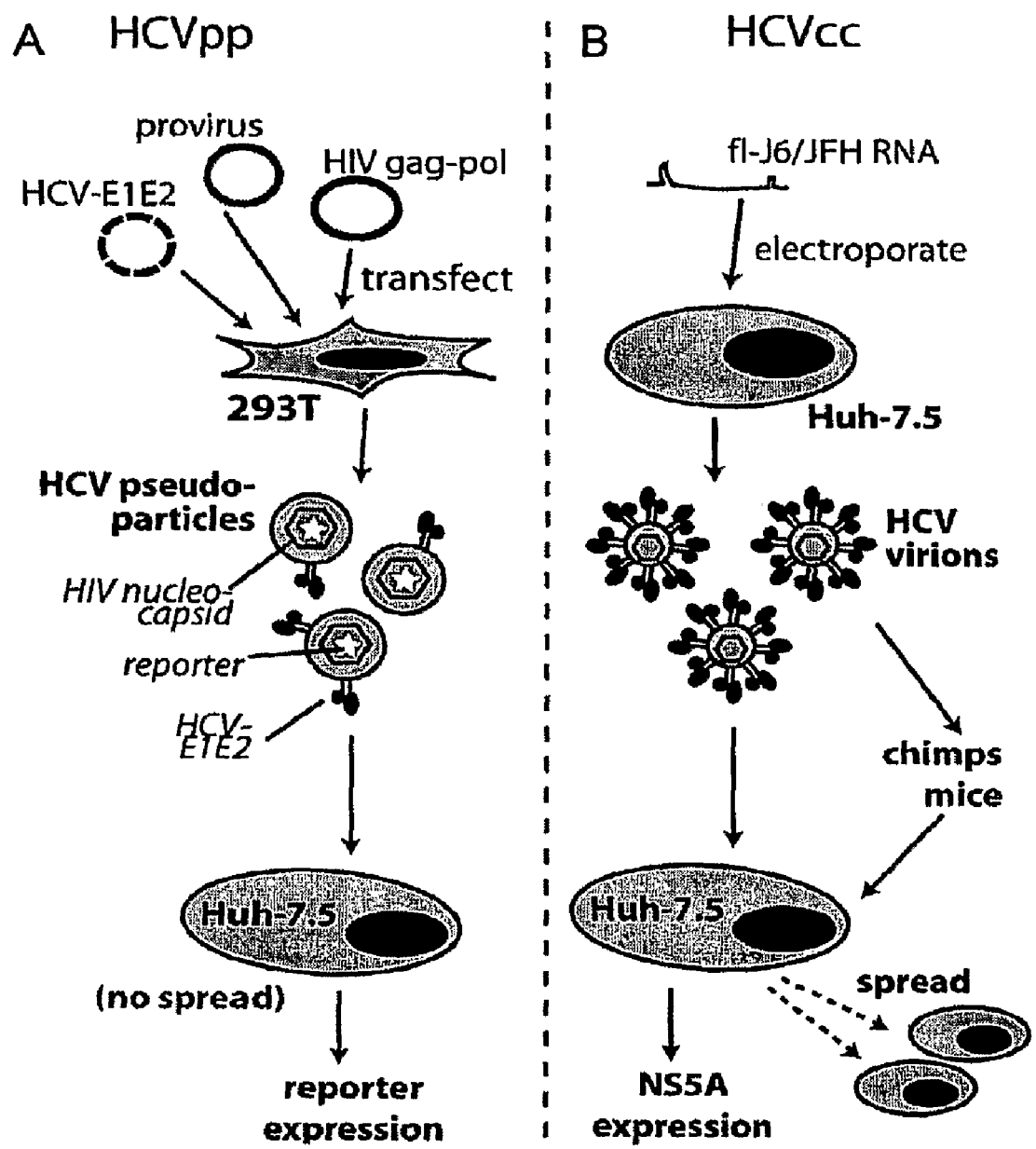
FIG. 2. Systems to study HCV entry. (A) HCV pseudotypes are generated in 293T cells by expression of retroviral Gag-Pol, HCV E1-E2, and a packagable RNA encoding a provirus with incorporated reporter, which can be used to monitor infection of transduced cells. (B) In the HCVcc system infectious viral particles are released from Huh-7.5 cells that stably replicate a J6/JFH RNA. These are infectious in naïve Huh7.5 cells and animal models. Serum from infected animals contains virus that is also infectious in culture.

A powerful iterative screening method to identify the HCV entry factor CLDN-1 was conducted. A complementation screen, where cDNA from an HCV permissive cell is transduced into a nonpermissive cell was conducted. To select for cells permissive for HCV entry HCVpp carrying a drug resistance reporter gene were used, allowing isolation of successfully infected cell clones. Initial attempts, where a retroviral human liver cDNA library was used to complement a variety of HCVpp nonpermissive cell lines (FIG. 2, boxed region), were unsuccessful due to an inherent background of nonspecific infection with pseudoparticles (unpublished data). In fact, further experiments demonstrated that no cell line in our collection was completely nonpermissive to even "no envelope" pseudoparticles bearing no viral envelope proteins, indicating the existence of nonspecific uptake mechanisms. In the screen, this resulted in a high background of drug resistant colonies, independent of HCV glycoprotein-mediated cell entry. Thus, unless the entry factor cDNA was highly represented in the library, a single round of transduction/challenge would not suffice. In fact, based on the observed background levels, it was calculated that one would need to systematically rescreen 2000-4000 drug-selected clones to find the cDNA of interest, if it were present at a frequency of $10^{-5}$ in the library. This calculation assumes an "ideal screen" with respect to cDNA cloning, transduction, and expression, with highly efficient HCVpp challenge and selection.

To deal with the high background observed in initial screens, methods that would allow multiple rounds of selection and enrichment were evaluated. Many systems have been described for rescuing and recycling retrovirally transduced cDNAs. Some depend on PCR to amplify the inserts from the genomic DNA of the transduced cell (Gudkov et al., 1994, Proc Natl Acad Sci USA 91:3744-8; Koh et al., 2002, Nucleic Acids Res 30:e142; Ossovskaya et al., 1996, Proc Natl Acad Sci USA 93:10309-14; Schott et al., 1997, Nucleic Acids Res 25:2940-2), which are then recloned into the retrovirus proviral expression plasmid, packaged, and transduced into naïve cells. Modifying the provirus to include sequences, such as LoxP sites and bacterial origins of replication, may also be accomplished, which allows rescue of the sequence from infected genomic DNA as plasmids capable of replication in bacteria (Hannon et al., 1999, Science 283:1129-30; Koh et al., 2002, Nucleic Acids Res 30:e142; Li et al., 1996, Cell 85:319-29; Oh et al., 2002, J Virol 76:1762-8).

Figure 3:
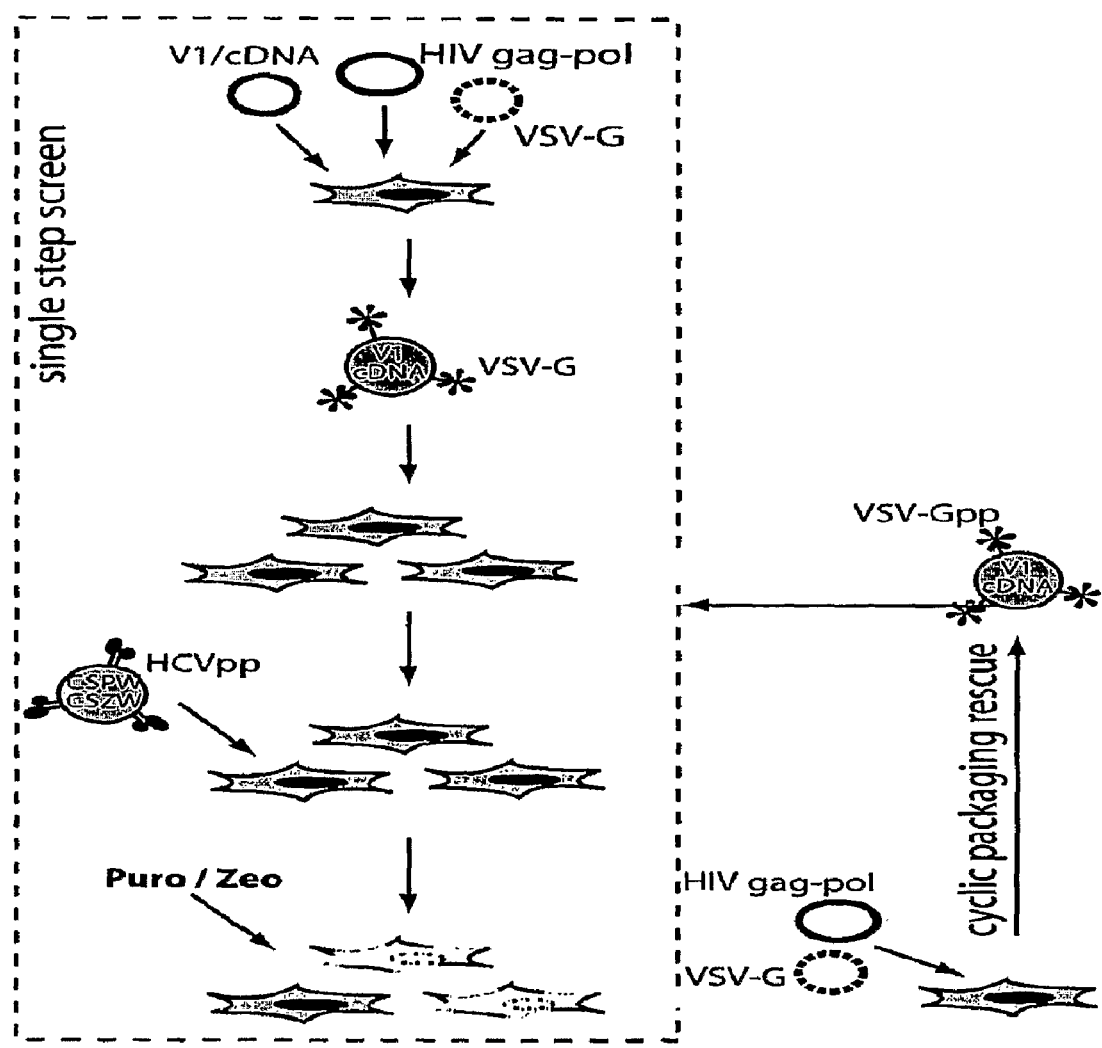
FIG. 3. Diagram of screen for HCV entry factors. A single round of screening of a cDNA library is shown in the dashed box, where a cDNA library constructed in the V1 HIV proviral vector and packaged into VSVG pseudoparticles is transduced into 293T cells. Transduced cells are then challenged with drug selectable HCVpp. For CPR surviving populations were transfected with the HIV gag-pol and VSVG expression plasmids to repackage the V1-cDNAs into pseudovirus used to infect naïve 293T cells, allowing recycling and reselection of cDNA clones exhibiting the desired specific activity.

A simpler approach that takes advantage of the intrinsic replication capacities of the retrovirus used to deliver the cDNAs was undertaken. Most retroviral vectors used for common gene-delivery applications are self-inactivating vectors that contain deletions in the long terminal repeat (LTR) elements. No packaging competent retroviral RNA transcripts are generated from such integrated proviruses. Instead transgene expression is driven by an internal non-retroviral promoter. In contrast, if the cDNA library is constructed in a provirus that retains the complete LTR elements, then the retroviral promoter should be active in transduced cell and a full length viral RNA should be expressed. Expression of the packaging components, gag-pol and envelope, in these cells allows packaging of this RNA into pseudoparticles capable of transducing naïve cells (FIG. 3). This approach, termed cyclic packaging rescue (CPR) (Bhattacharya et al., 2002, Proc Natl Acad Sci USA 99:8838-43; Koh et al., 2002, Nucleic Acids Res 30:e142), allows retrieval of the library after selection has been performed, transduction of a naïve cell population, followed by a new round of selection. This process can be repeated sequentially for an unlimited number of selection/enrichment steps. In addition, this approach has the benefit of cycling the cDNA library through multiple cellular populations, thereby avoiding the selection of cell clones that are more prone to take up retroviral particles through non-specific, HCV-glycoprotein independent mechanisms.

For an additional level of selection, two challenge virus genomes were used, each encoding a different drug selectable marker, puromycin (CSPW) (Besnier et al., 2002, Proc Natl Acad Sci USA 99:11920-5) or zeocin (CSZW) resistance, in self-inactivating lentiviruses (Demaison et al., 2002, Hum Gene Ther 13:803-13). Thus, after challenge and selection of a library transduced population with one HCVpp packaged selection cassette (e.g., CSPW), the population can be pooled and rechallenged with the second selectable pseudovirus (e.g., CSZW). Then, during CPR, only the full-length retroviral transcripts from the non-self-inactivating provirus that encodes the library but not the self-inactivating challenge virus genomes is repackaged and transferred to the naïve cell population. This enabled us to perform multiple rounds of selection thereby overcoming the background of non-specific pseudoparticle uptake. Using this scheme, it was estimated that a rare cDNA represented at a frequency of $10^{-5}$ in the initial cDNA library would be enriched 25-fold after a single round of screening (1/4000). Assuming similar enrichment in subsequent selection cycles (25-fold per selection), the cDNA of interest would be highly represented (1/6.4. in the population after only three rounds of CPR and drug selection).

Although systems for Moloney murine leukemia virus (MLV) CPR have been described (Bhattacharya et al., 2002, Proc Natl Acad Sci USA 99:8838-43; Koh et al., 2002, Nucleic Acids Res 30:e142), a lentivirus (HIV)-based system was used to deliver the cDNA library, since lentiviral pseudoparticles can be packaged to higher titers and infect a wider range of cell types. Expression of mature, packagable RNA from the HIV-1 promoter is dependent on viral accessory proteins, such as Tat and Rev. In a single round HIV-1 pseudoparticle production, the viral RNA can be expressed from an exogenous promoter, alleviating the need for these accessory proteins. However, CPR with an HIV-1 provirus requires the use of the HIV-1 promoter and expression of accessory proteins. To fulfill this requirement, we used an HIV-1 provirus, termed V1, where the gag-pol and envelope genes were deleted, but most of the accessory protein transcripts remained intact (Cowan et al., 2002, Proc Natl Acad Sci USA 99:11914-9; Simon et al., 2005, PLoS Pathog 1:e6). In this plasmid, the nef gene was also deleted and replaced with a cloning site where the cDNA of interest could be cloned and expressed. This system was first tested with a control plasmid, V1-GFP, which encoded GFP in place of a cDNA. When V1-GFP, HIV gag-pol and VSVG plasmids were cotransfected into 293T cells high titers of released pseudoparticles were obtained ($7 \times 10^5$ to $3 \times 10^7$ transducing units (TU)/ml depending on the target cell line). To determine the efficiency of V1-GFP CPR, numerous cell lines that had been transduced with this pseudovirus were transfected with HIV gag-pol and VSVG. All tested cells lines produced re-packaged pseudoparticles, which were then titered on a naïve population of the same cell line. Although titers varied by several orders of magnitude between cell lines, all were $>1 \times 10^4$ TU/ml, demonstrating the capacity of this lentiviral system to undergo CPR and its utility for the screen.

cDNA library was constructed from the hepatocarcinoma Huh-7.5 cell line, a subclone of the Huh-7 cell line highly permissive for HCV subgenomic replicons (Blight et al., 2002, J. Virol. 76:13001-14). Huh-7.5 cells are susceptible to both HCVcc and HCVpp and thus must express all molecules required for HCV infection. The final V1-Huh-7.5 cDNA library contained $2.5 \times 10^6$ clones, 95% of which had inserts averaging 970 bp in size. Since the V1 vector does not encode a reporter gene, pseudoviruses carrying this library were first titered alongside a stock of V1-GFP virus on the TZM HeLa indicator cell line, where an integrated lacZ gene is transcriptionally regulated by the HIV-1 LTR (Derdeyn et al., 2000, J Virol 74:8358-67; Platt et al., 1998, J Virol 72:2855-64; Wei et al., 2002, Antimicrob Agents Chemother 46:1896-905). Infection of a TZM cell by a V1 containing pseudotype results in Tat expression from the V1 provirus and lacZ activation. The ratio of infectivity of these two viruses (V1-library and V1-GFP) on TZM cells was then used to approximate the effective titer of the library virus on the cell line of interest, based on the measurable infectivity of V1-GFP.

The target cell line for the screen was chosen based on several criteria. As stated above, the primary requirement was that (1) the cell line must express as many of the putative HCV entry factors as possible, most importantly CD81 and SR-BI, but be non-susceptible to HCVpp infection. (2) To minimize nonspecific background, cell lines with lower uptake of HCVpp and "no envelope" pseudoparticles were preferred. It should be noted that careful analysis of candidate cell lines, comparing high titer HCVpp and "no envelope" pseudoparticles, revealed that most cells exhibit a susceptibility to HCVpp that is minimally above that for "no envelope" pseudoparticles. (3) To ensure that nonpermissiveness was a phenotype due to lack of an HCV-specific entry factor(s) rather than poor infection by pseudotypes in general, we chose cell lines that were highly permissive to VSVGpp infection. This also made it more likely that the target cell line would be easily transduced with the V1 library. (4) For selection of successful HCVpp infections, candidate cell lines also had to be susceptible to the desired drug selections. (5) Since we planned to perform multiple rounds of screening involving CPR, the ideal cell line had to perform this function well and be highly transfectable. (6) Finally, to facilitate the screen, the chosen cell line needed to be relatively fast growing and clone efficiently.

Seven cell lines were identified as potential candidates based on their lack of HCVpp susceptibility and expression of CD81 (HepH, 293T, SW13, HeLa, Caco-2, FetHep1.3, HOS).

Figure 4:
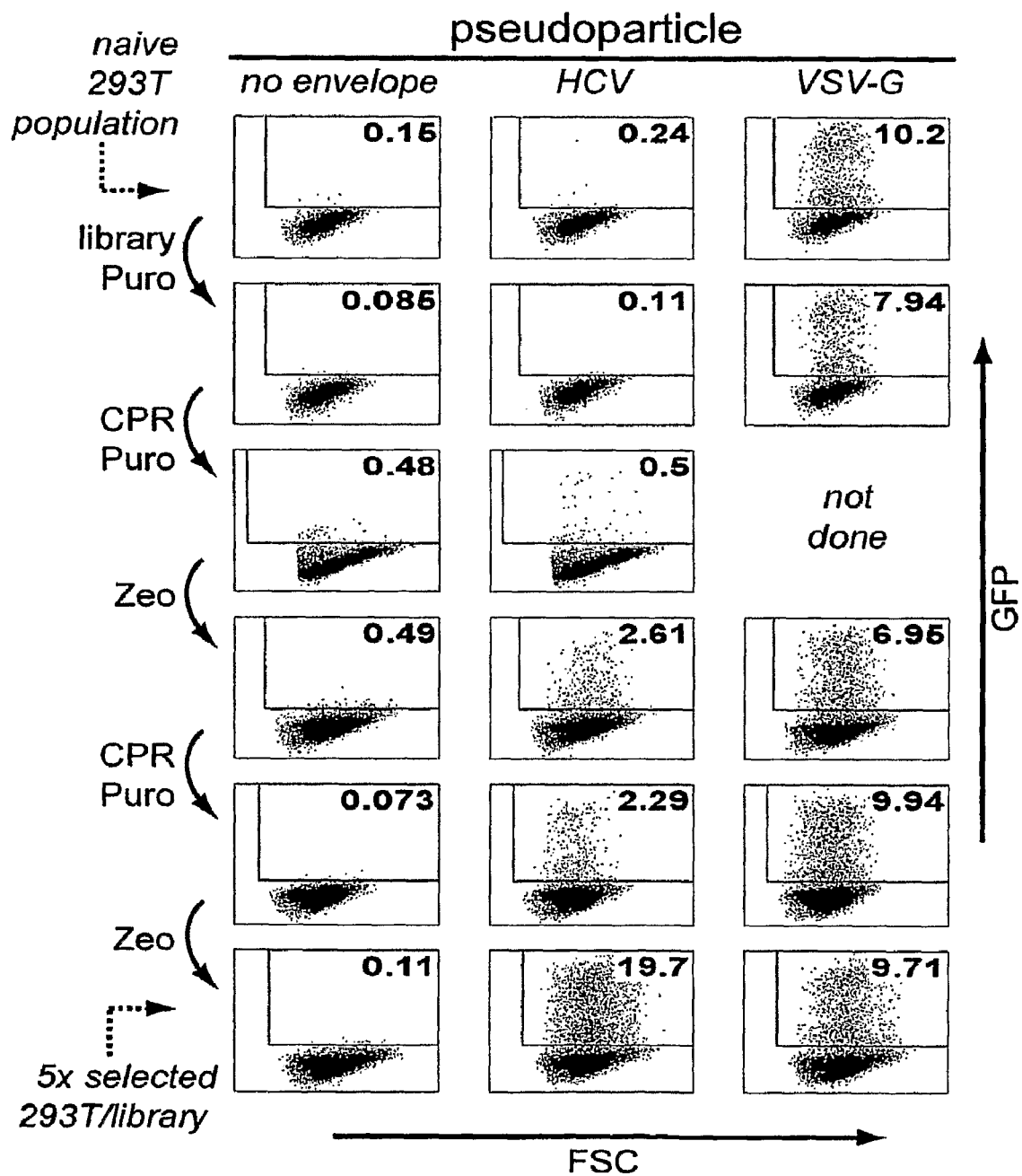
FIG. 4. Increasing susceptibility of 293T cells to HCVpp over the course of the cDNA library screen. Each row corresponds to a population of 293T cells during the screen, beginning with an untransduced population at the top and ending with a population that has been subjected to a total of 2 repackaging steps (CPR) and 5 selection steps (Euro, Zeo). At each stage the population was infected with GFP-reporter (CSGW) pseudoparticles bearing no glycoproteins ("no envelope"), HCVE1E2 (HCV) and VSV G protein (VSV-G). A gradual increase in susceptibility to HCVpp was observed (middle column) while susceptibility to "no envelope" and VSV-G remained unchanged.
Figure 5:
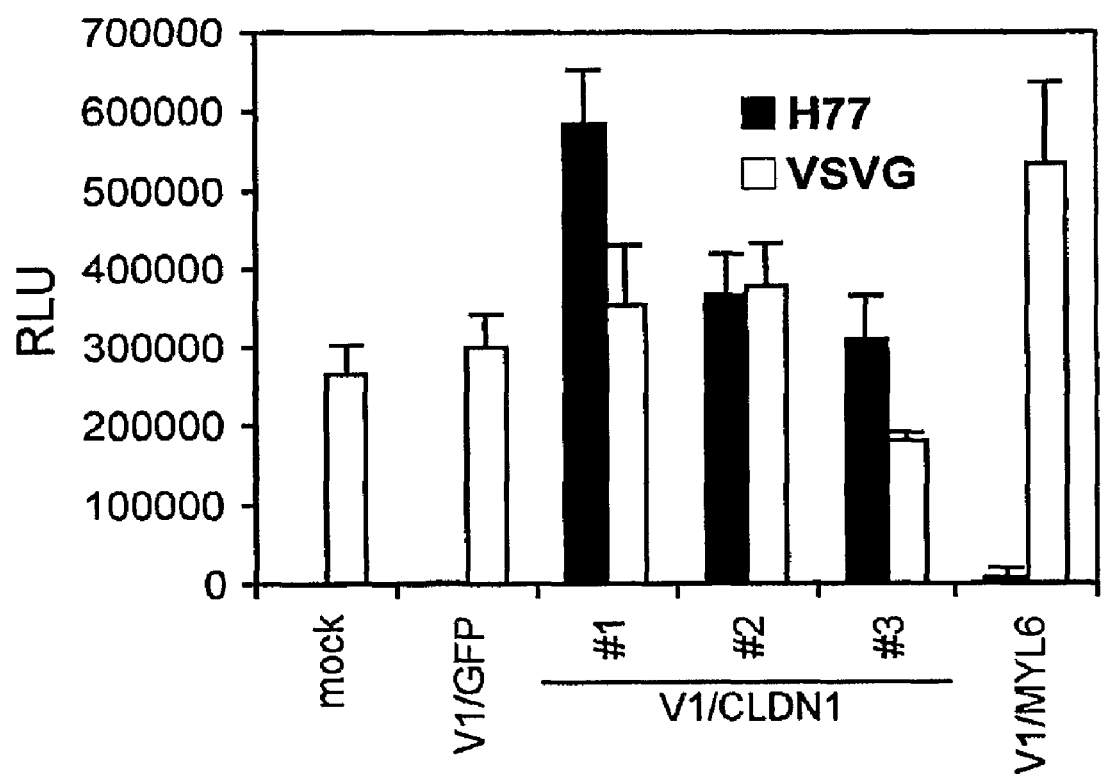
FIG. 5. Retesting of hits from cDNA screen. 293T cells infected with V1 viruses encoding defined CLDN1 and MYL6 cDNAs that were recovered from the screen and recloned exactly as found in the cDNA library screen were challenged with either HCVpp of VSVGpp expressing luciferase, which was quantified 48 hpi as shown (mean+/−SEM, n=3).
Figure 6:
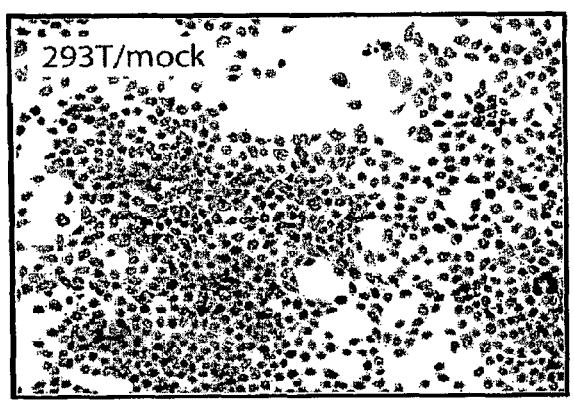
FIG. 6. HCVcc infection in 293T/CLDN1 cells. Mock or pTRIP-CLDN1 infected 293T cells were challenged with J6/JFH HCVcc 48 hours prior to immunostaining for NS5A (in brown). Nuclei were counterstained with hematoxylin (blue).
Figure 6:
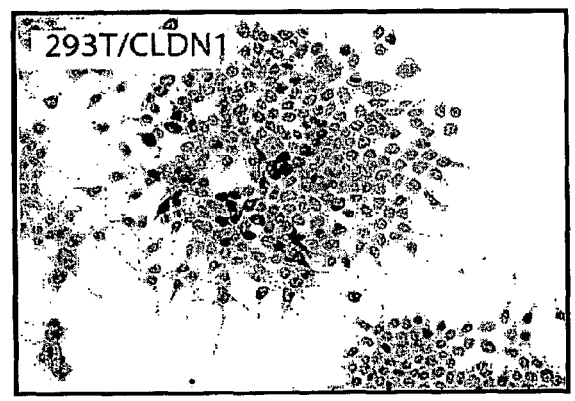

Initially the V1-Huh-7.5 cDNA library was co-transfected with HIV gag-pol and VSVG into 293T cells to generate lentiviral pseudoparticles carrying the cDNA library and bearing VSVG on their surface (V1/library-VSVGpp). A GFP carrying control (V1/GFP-VSVGpp) was generated in parallel. Both V1/library-VSVGpp and V1/GFP-VSVGpp were titered on TZM cells; V1/GFP-VSVGpp was also titered on 293T cells. The calculated titer of V1/library-VSVGpp on 293T cells was $4 \times 10^6$ TU/ml. During the early stages of the screen, the library was delivered at a MOI between 1 and 5 TU/cell; to enhance the frequency of single hit transductants, a 10-fold lower MOI was used for the final cycle. CSPW-HCVpp was used for infection, and selected with Puro. The number of PuroR colonies was not strikingly different between library and mock transduced cells. PuroR colonies were pooled for each population (library and mock) and infected a fraction of each population with a GFP-carrying HCVpp (CSGW-HCVpp) as well as "no envelope" (CSGW-"noenv" pp) and VSVG bearing CSGW (CSGW-VSVGpp) pseudoparticles (FIG. 4, second row). The remaining cells were kept in culture and used to repackage the library. We continued to perform assessments of CSGW-HCVpp susceptibility after each selection step (FIG. 4). Using FACS to quantify GFP expression at a single cell level would allow the detection of the emergence of a small subpopulation of HCVpp permissive cells at an early stage. As seen in FIG. 4, a total of five selection steps and two CPR steps were performed. After the initial Puro selection we performed CPR, followed by two selection steps with CSPW and CSZW, respectively. Another CPR step was followed by two more selection steps, again first with CSPW followed by CSZW. After the second selection step, a small number of GFP-positive cells was visible for the first time while there was no change in the number of GFP positive cells after infection with CSGW-"noenv" pp or CSGW-VSVGpp (FIG. 5, fourth row). The CSGW-HCVpp susceptible population was enhanced after another selection step. After a total of five selection steps almost 20% of the library expressing 293 T cells were GFP positive after challenge with CSGW-HCV while their susceptibility to CSGW-"noenv" pp and -VSVGpp remained unchanged (FIG. 4, bottom row). This corresponded to a 100-fold increase in the titer of CSGW-HCVpp from $5 \times 10^2$ TU/ml in the parental 293T population to $5 \times 10^4$ TU/ml in the 293T population expressing the library after five selection steps, a level of susceptibility close to that seen in Huh-7.5 cells. At the same time, the titers of CSGW-"noenv" pp on the same cell populations were $3.5 \times 10^2$ and $2 \times 10^2$; and those of CSGW-VSVGpp $1.6 \times 10^7$ and $2 \times 10^7$ TU/ml. This increase in susceptibility to CSGW-HCVpp (but not CSGW-"no env" pp or CSGW-VSVGpp) was paralleled by an increase in the number of colonies after antibiotic selection (i.e., an increase in the susceptibility of the library expressing population to HCVpp encoding PuroR or ZeoR) from <2-fold compared to mock to >60-fold).

Given the high proportion of HCVpp-susceptible cells following the final round of selection, we examined the transduced cDNAs expressed within these cells. Genomic DNA was prepared from a pool of the selected clones and used as template in PCR across the V1 provirus cDNA-cloning site. Two distinct species were amplified, which were subsequently cloned and sequenced. The major, larger species was identified as the full-length cDNA for CLDN1. The lesser, smaller species was identified as myosin light chain polypeptide 6 (myl6) transcript variant 2. We subsequently isolated individual cell clones from the selected population and examined the V1-encoded cDNA by PCR and sequencing. We found that 18 of 20 (PCR failed to amplify a product for two clones) clones contained CLDN1 cDNA, while three also contained myl6 cDNA (one transcript variant 1 and two variant 2 clones). Although all V1 CLDN1 cDNA clones contained the entire CLDN1 ORF, their exact termini varied, indicating that at least five independent CLDN1 clones had been isolated in the screen.

The results of the screen suggested that CLDN1 was required for HCVpp entry, while MYL6 might influence or enhance this activity. To test these candidates, we recloned amplified products into V1 to recreate the expression cassettes isolated in the screen. Naïve 293T cells were transduced with these sequence verified proviruses, alone or in combination, and tested for HCVpp susceptibility using an HIV-based pseudoparticle encoding firefly luciferase as a reporter gene (pNL4.3) (Connor et al., 1995, Virology 206: 935-44; Hsu et al., 2003, Proc. Natl. Acad. Sci. USA 100: 7271-76). We found V1-CLDN1 transduction enhanced susceptibility to HCVpp (pNL4.3-HCV) by 1000-fold while V1-MYL6 and V1-GFP (negative control) had no significant effect (FIG. 5). Transduction with CLDN1 had no effect on VSVGpp susceptibility. These effects were not influenced by the V1-expressed HIV-1 accessory proteins, since cloning CLDN1 and MYL6 into pTRIP (Sirven et al., 2001, Mol Ther 3:438-48; Zennou et al., 2000, Cell 101:173-85), a self-inactivating lentiviral provirus that expresses no HIV proteins, but instead employs an internal CMV promoter to express cloned genes, yielded identical results. Thus, our screen successfully identified CLDN1 as an entry factor required for HCVpp infection of 293T cells. The reason why MYL6 surfaced in the screen is still unclear, but it has no apparent effect on HCVpp infection of 293T cells whether expressed alone or in combination with CLDN1. For this reason, we have focused our subsequent studies on CLDN1.

Figure 7:
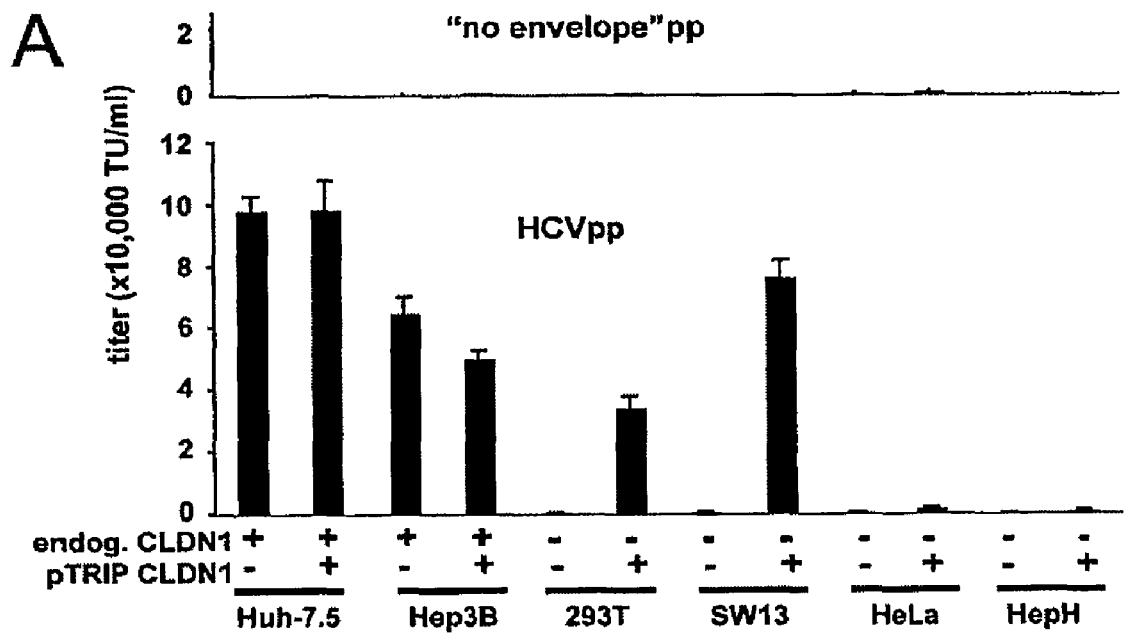
FIG. 7. HCVpp infection of 293 T/CLDN1 cells. A "no envelope" pp (top) and HCVpp (bottom) infection of diverse human cell lines; "endog. CLDN1" and "pTRIP CLDN1" indicate endogenous expression and lentiviral mediated overexpression, respectively. B Infection of 293T cells expressing human claudins 1, 3 and 7 or mouse CLDN1.
Figure 7:
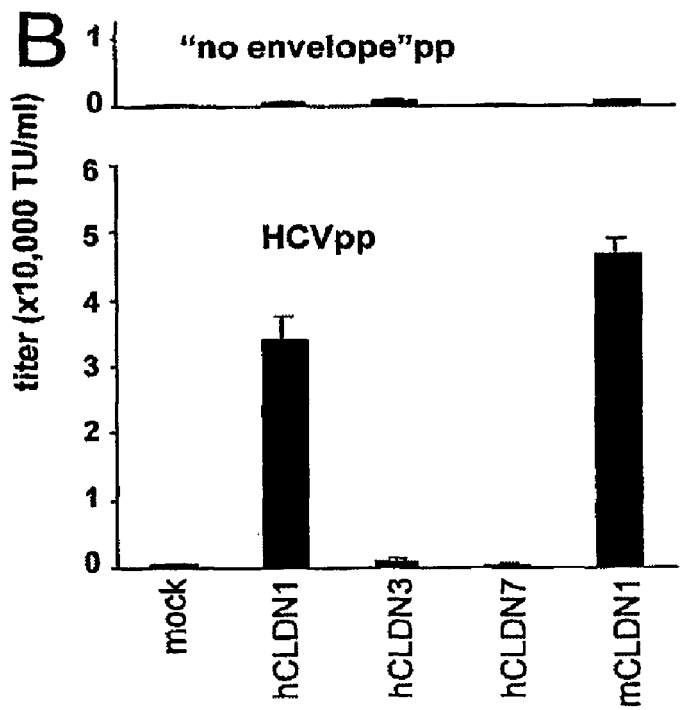

Thus far, we have demonstrated a role for CLDN1 in infection with pseudoparticles bearing the genotype 1a H77 envelope glycoproteins. To determine if CLDN1 also mediates entry of HCV virions, we challenged naïve or CLDN1 transduced 293T cells with HCVcc, produced from the chimeric genotype 2a J6/JFH-1 full-length genome (F1-J6/JFH) (Lindenbach et al., 2005, Science 309:623-6). Cells were fixed and immunostained for NS5A expression 48 h post infection. While naïve 293T cells showed no positive NS5A staining after mock or HCVcc infection, CLDN1 transduced 293T cells were positive for NS5A after challenge with HCVcc, but not when mock infected (FIG. 7). These results demonstrate that in 293T cells CLDN1 is required for infection with not only HCVpp but also HCVcc. Since the envelope proteins of these two species are of a highly divergent genotype (1a versus 2a), these results strongly suggest that CLDN1's role in HCV entry will be conserved among diverse HCV genotypes.

To see if the permissiveness to HCVpp infection in response to CLDN1 expression was unique to 293T cells or held true for other cell lines, we tested a variety of cell lines, including HCVpp permissive cell lines (Huh-7.5, Hep3B, HepG2/hCD81) and non-permissive cell lines that been considered for the screen (293T, HepH, SW13, HeLa), pre- and post-CLDN1 transduction, for HCVpp permissiveness. Among these seven cell lines, prior to TRIP-CLDN1 transduction we found a perfect correlation between endogenous CLDN1 expression and HCVpp permissiveness, with all three permissive cell lines being CLDN1 positive and all four non-permissive cells negative (FIG. 7A). As seen before, 293T cells became highly permissive when expressing CLDN1. The same phenotype was also observed for SW13. Both HeLa and HepH cells responded to CLDN1 expression with a reproducible increase in HCVpp permissiveness, but the effect was much smaller than that observed for 293T or SW13 cells. For HeLa cells, this finding is at least partly explained by generally poor permissiveness of these cells to CSGW based pseudoparticles as evidenced by a 10-fold reduced titer of CSGW-VSVGpp on HeLa cells as compared to all other human cell lines tested. This HeLa specific effect is most likely due to low expression from the spleen focus forming virus promoter driving GFP expression in CSGW. HepH cells, however, displayed low level susceptibility to HCVpp upon expression of CLDN1 even though transgene expression was very high. The HepH cell line is highly permissive to VSVGpp suggesting that other HCV entry factors may be missing or limiting in this line. Thus CLDN1 is important for HCVpp entry in a range of human cells.

To see if CLDN1's enhancement of HCVpp infection was specific and not a general phenomenon of claudin overexpression, we cloned the open reading frames of selected claudin family members and examined their ability to promote HCV entry in 293T cells. Initially, we tested CLDN7, which has the highest sequence identity to CLDN1 (60% identity, 78% similarity; BLASTP 2.2.12, BLOSUM62 matrix), and CLDN3, which is the closest CLDN1 relative that is preferentially expressed in the liver (49% identity, 66% similarity to CLDN1). Both coding sequences were cloned into the pTRIP provirus, packaged, and transduced into naïve 293T cells. While cells transduced with pTRIP-CLDN1 became permissive to HCVpp, neither the CLND3-nor CLDN7-transduced cells were infectable with HCVpp (FIG. 7B). Thus far, we have validated that CLDN3 is expressed at levels similar to CLDN1 in the transduced 293T cell populations. While immunoblotting for CLDN7 has thus far not been successful, we have expressed CLDN7-GFP fusions, which convincingly demonstrate expression, but fail to promote entry; the corresponding GFP fusion of CLDN1 is fully functional. These data indicate that CLDN1, and not other closely related claudin family members, enhances HCVpp entry in 293T cells. These results form the basis for mapping the CLDN1 determinants required for HCV entry (D1).

Figure 8:
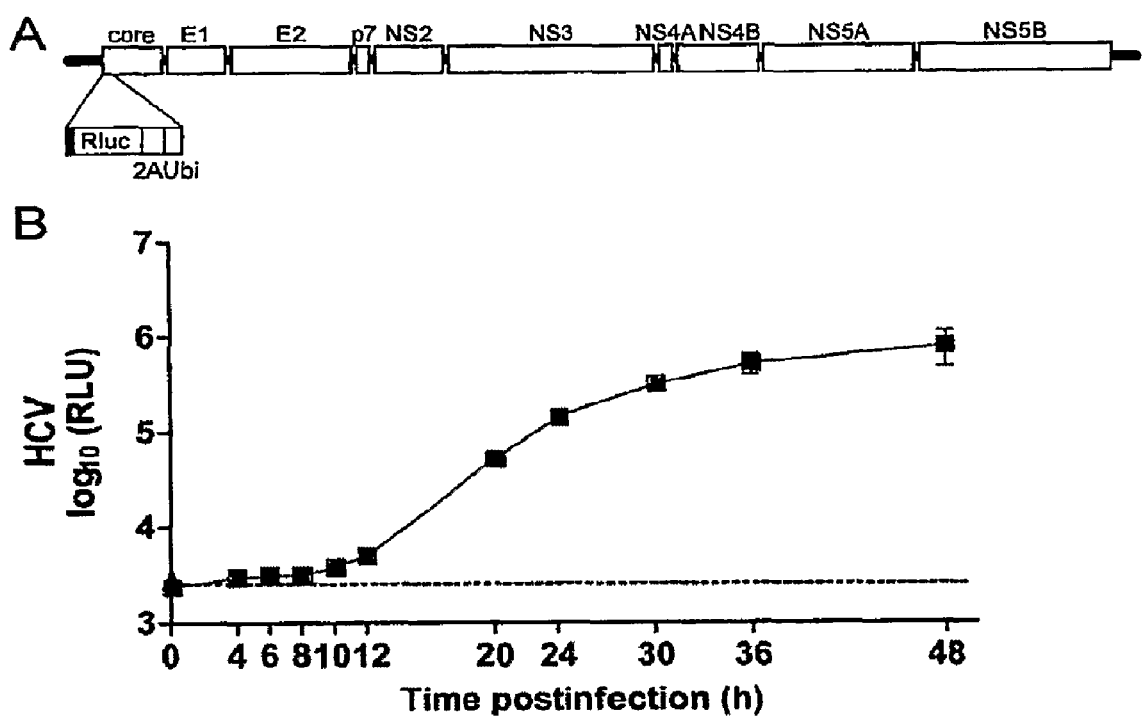
FIG. 8. Characterization of FL-J6/JFH-5′C19Rluc2AUbi. (A) Schematic of FL-J6/JFH-5′C19Rluc2AUbi. (B) Huh-7.5 cells were infected with FL-J6/JFH-5′C19Rluc2AUbi for the indicated times. At each timepoint, cells were harvested and luciferase activity determined. The dashed line indicates the background level of the assay from naïve Huh-7.5 cells.
Figure 9:
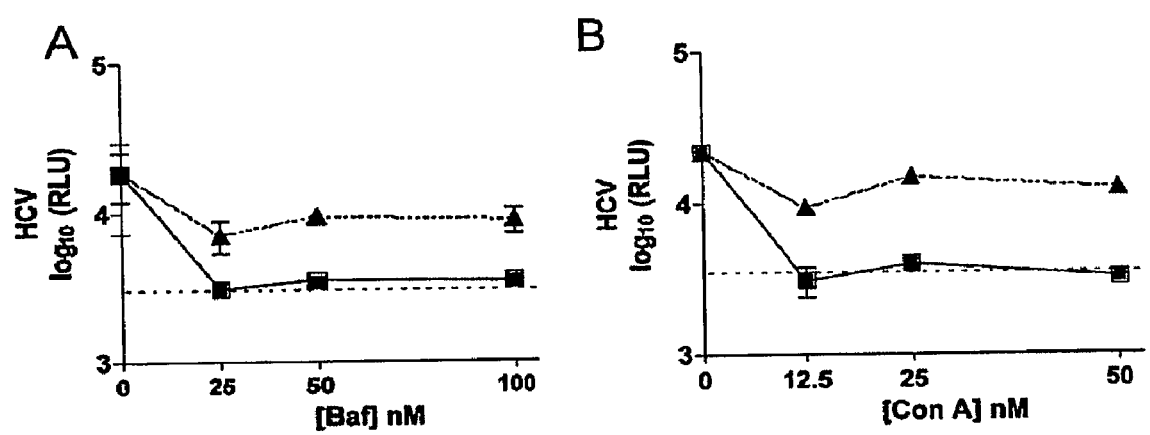
FIG. 9. HCVcc entry is sensitive to inhibitors of endosomal acidification. (A) Huh-7.5 cells were treated with bafilomycin A1 either prior to infection (squares) or at 3 h postinfection (p.i.) (triangles) with FL-J6/JFH-5′C19Rluc2AUbi. Samples were harvested for luciferase assays at 24 h p.i. The dashed line indicates the background level of the assay from naïve Huh-7.5 cells. (B) Huh-7.5 cells were treated with concanamycin A and infected as above.

Using the recently developed HCVcc system (Lindenbach et al., 2005, Science 309:623-6), we have begun examining several aspects of the HCV entry pathway into Huh-7.5 cells. In these studies, we used an HCV virus termed FL-J6/JFH-5'C19Rluc2Aubi that encodes the *Renilla* luciferase reporter gene (FIG. 8A). Luciferase activity from this virus is proportional to replication and hence provides a sensitive assay for detection of HCV infection (FIG. 8B). To determine if HCV entry is pH-dependent, we utilized bafilomycin A1 and concanamycin A, inhibitors of vacuolar H+-type ATPases. These agents prevented HCV entry when present prior to infection and had minimal effect on downstream replication events (FIG. 9). HCV entry therefore appears to be pH-dependent requiring an acidified intracellular compartment. This result confirmed what was previously suggested from studies using HCVpp, which were also sensitive to inhibitors of endosomal acidification (Hsu et al., 2003, Proc. Natl. Acad. Sci. USA 100:7271-76; Zhang et al., 2004, J Virol 78:1448-55).

Figure 10:
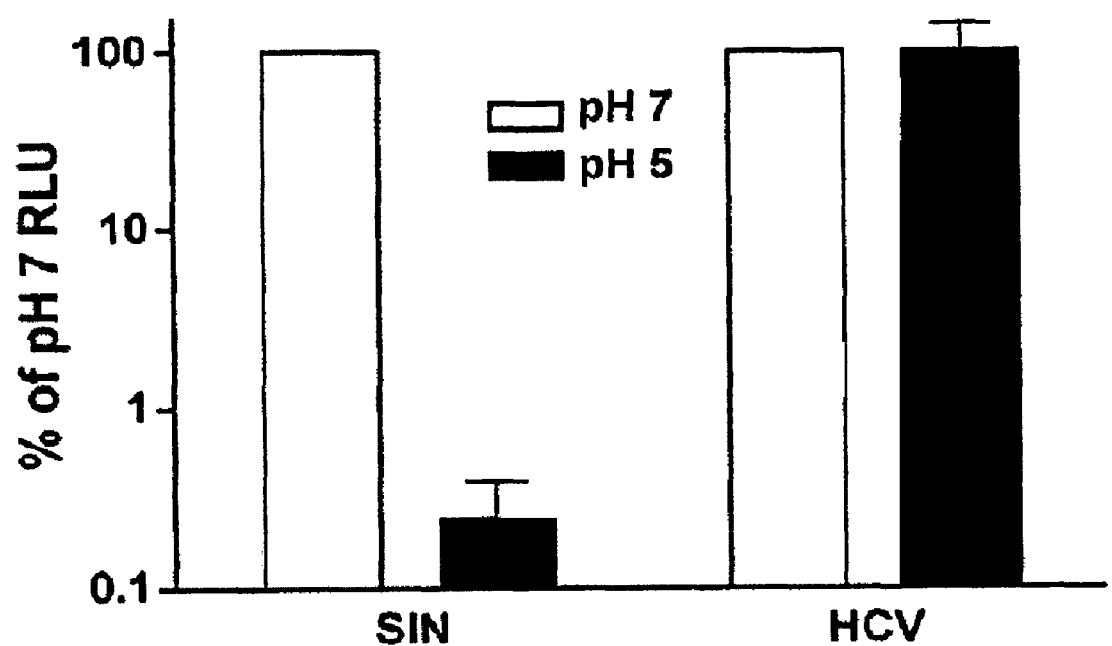
FIG. 10. HCV infectivity is resistant to acidic pH. HCVcc or Sindbis (SIN) was diluted in citric acid buffer (15 mM citric acid, 150 mM NaCl) at pH 7 (white bars) or pH 5 (black bars) for 10 min at 37° C. Samples were neutralized and used to infect Huh-7.5 cells. Samples were harvested at 24 h (SIN) or 48 h (HCV).
Figure 11:
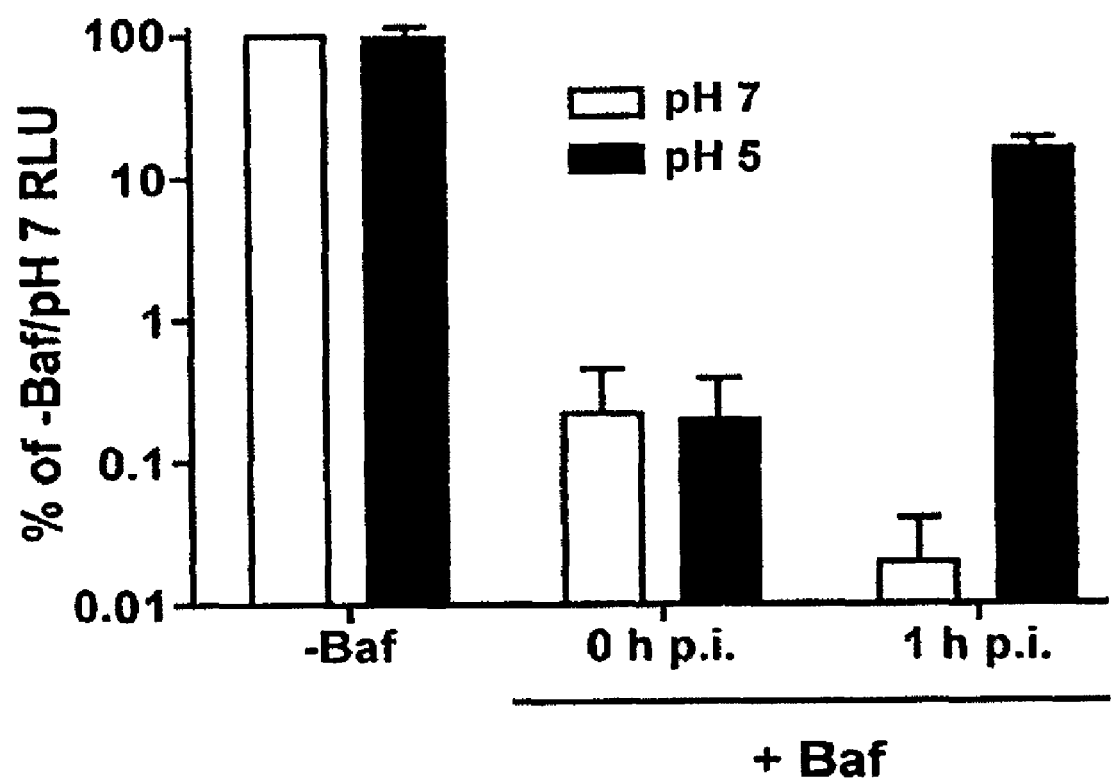
FIG. 11. Incubation at 37° C. allows HCV to enter bafilomycin-treated cells. Huh-7.5 cells were treated with bafilomycin A1 (+Baf) and infected with HCVcc at 4° C. for 2 h. Cells were then washed with citric acid buffer at pH 7 (white bars) or pH 5 (black bars) immediately (0 h p.i.) or after 1 h at 37° C. (1 h p.i.). Cells were incubated in media containing bafilomycin for 24 h.

For many other enveloped viruses, acidic pH triggers an irreversible conformational change, which promotes virionendosomal membrane fusion. Such viruses are often inactivated by low pH. In the case of HCV, however, exposure of virions to acidic pH followed by return to neutral pH did not affect their infectivity (FIG. 10). This parallels what we observed for the related pestivirus bovine viral diarrhea virus (BVDV). We found that low pH resulted in entry of cell surface bound HCV in the presence of bafilomycin, but only after prolonged incubation at 37° C. (FIG. 11), suggesting the existence of rate limiting, post-binding events needed to render HCV competent for low pH triggered entry. Such events may involve interactions with a cellular co-receptor or other factors that presumably act upon the viral particle to render it pH-sensitive (and hence fusion competent). Inhibitors of cathepsins B and L, late endosomal proteases that activate Ebola virus and reovirus for entry, did not affect HCV entry.

To investigate the role of CLDN1 in HCV infection, CLDN1 specific reagents will be developed, in particular, antibodies directed against the CLDN1 extracellular loops, which will be raised in chicken using highly purified peptides representing epitopes of the predicted extracellular loops of CLDN1.

Figure 12:
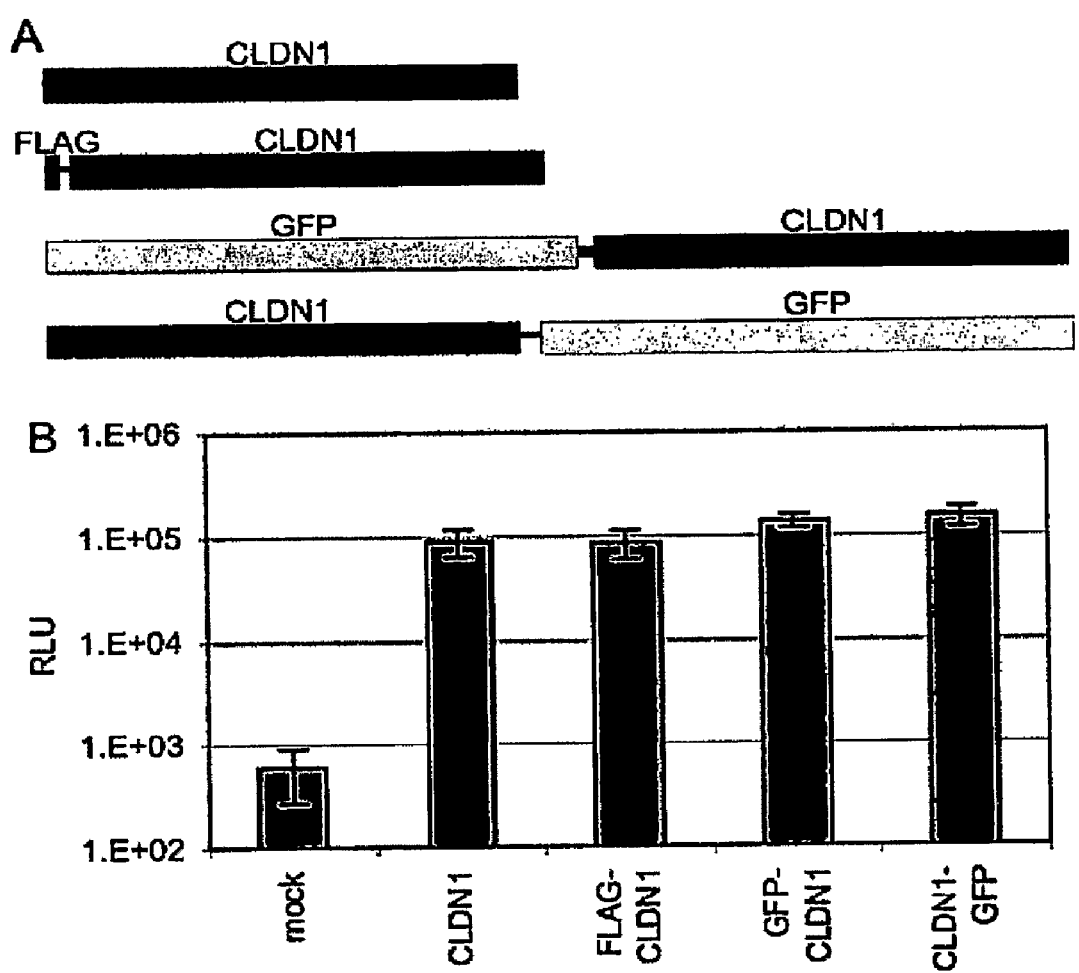
FIG. 12. CLDN1 fusion constructs. (A) Diagram of CLND1 fusion cassettes expressed from the lentiviral pTRIP vector. (13) 293T cells transduced to express these CLDN1 proteins were challenged with HCVpp expressing luciferase, which was quantified 48 hpi (mean+/−SEM, n=3).

In addition, functional tagged derivatives of CLDN1 will be developed. Using the pTRIP lentivirus vector we have constructed FLAG epitope (FLAG-CLDN1) or GFP (GFP-CLDN1) fusions to the CLDN1 N-terminus as well as a C-terminal GFP fusion (CLDN1-GFP) GFP fusion (FIG. 12A). When transduced into naïve 293T cells, all fusions allowed infection with HCVpp, as assayed with luciferase reporter pseudoparticles (pNL4.3) (Connor et al., 1995, Virology 206:935-44; Hsu et al., 2003, Proc. Natl. Acad. Sci. USA 100:7271-76) (FIG. 12B). In addition to this entry phenotype, the FLAG-CLDN1 could be immunoprecipitated with agarose conjugated anti-FLAG M2 monoclonal antibodies (Sigma) and the GFP fusions were visible in transduced cells in patterns typical of CLDN1 immunostaining (not shown).

Figure 13:
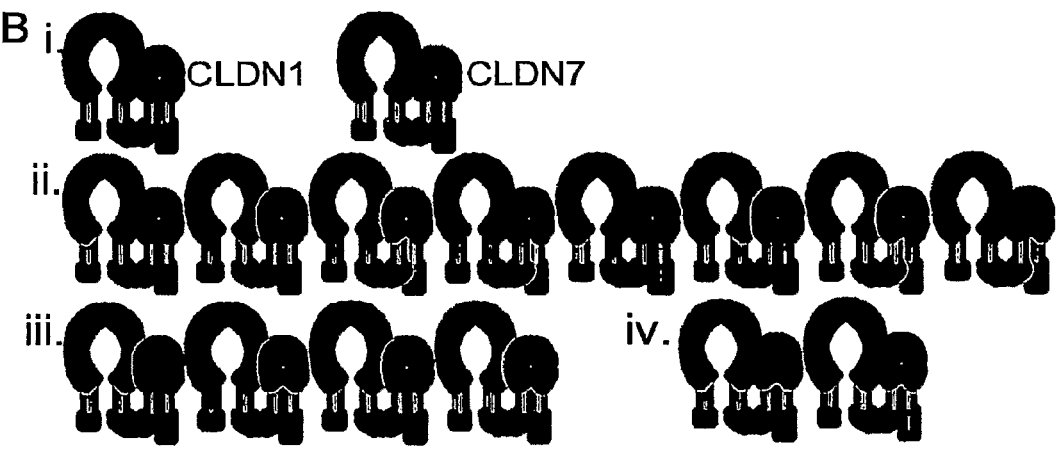
FIG. 13. Mapping of determinants for claudin specific HCV entry determinants. (A) ClustalW alignment of CLDN1 (top; SEQ ID NO:1) and CLDN7 (bottom; SEQ ID NO:3) protein sequences, with matches shown as dots and differences as labeled. The predicted transmembrane domains are boxed and the extracellular loops (EL1 and EL2) are indicated with dashed lines. (B) Diagram of proposed CLDN1 (dark) and CLDN7 (light) chimeras. Full length, wild type clones (i) are represented by a single color. Chimeras with a single junction (ii) or precise swaps of one (iii) or both (iv) extracellular loop are diagramed with regions from each protein corresponding to the respective color. Each will be cloned as with an N-terminal GFP fusion.
Figure 14:
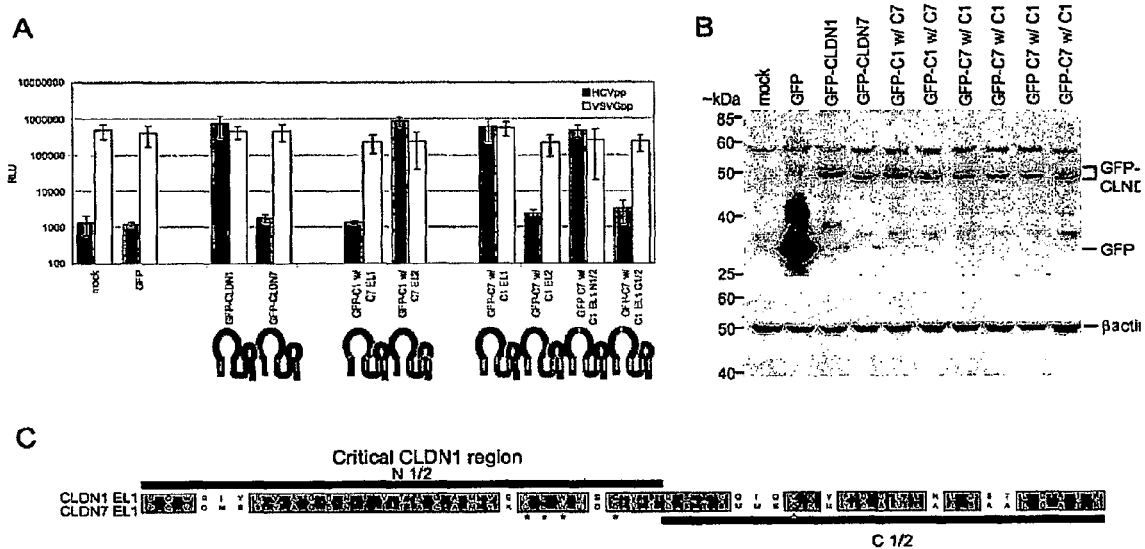
FIG. 14. Extracellular loop-1 (EL1) of CLDN1 contains specific HCV entry determinants. Reciprocal CLDN1/CLDN7 chimeras were constructed to map the sequence differences responsible for their different infectivity phenotypes. (A) The extracellular loops of either the HCV permissive CLDN1 (dark lines in claudin diagram below graph) or nonpermissive CLDN7 (light lines in claudin diagram below graph) were swapped into the reciprocal gene. These chimeras were constructed as GFP-claudin fusions in the TRIP lentiviral vector. 293T cells transduced with these proviruses were subsequently challenged with either HCVpp (graph bars) or VSVGpp (white bars) encoding the luciferase reporter gene. Each value is the mean of three independent infections assayed 48 hpi with error bars representing one standard deviation. (B) All chimeric GFP-claudin proteins are similarly expressed. Total cellular protein lysates were prepared from transduced 293T cells, resolved by SDS-PAGE gel electrophoresis, transferred to nitrocellulose membrane, and immunoblotted with an anti-GFP (top) or β-actin (bottom) mouse monoclonal antibody. (C) Alignment of CLDN1 (SEQ ID NO:1, residues 28-81) and CLDN7 (SEQ ID NO:3, residues 28-81) EL1 sequences. Summarizing the data in (A), the first half of CLDN1 is capable of mediating HCV entry when expressed in CLDN7.

To map the CLDN1 determinants required to mediate HCV infection, we plan to take advantage of the different phenotypes conferred by closely related CLDN1 and CLDN7. As described above, even though CLDN7 is 60% identical and 78% similar in amino acid sequence to CLDN1 (FIG. 13A), its expression does not promote HCVpp entry. Reciprocal CLDN1/CLDN7 chimeras will be used to map the sequence differences responsible for their different infectivity phenotypes. This approach was previously used to map the *Clostridium perfringens* enterotoxin binding domain of CLDN3 to its second extracellular loop (Fujita et al., 2000, FEBS Lett 476:258-61). Initially, a nested set of chimeras will be created encoding N-terminal segments of increasing length from one claudin, with the remaining C-terminal sequence from the other. Since the extracellular loops are of obvious interest, junctions will be chosen flanking the domains between TM1/EL1, EL1/TM2, TM3/EL2, and EL2/TM4 (FIG. 13B, ii). It is possible that interactions between claudin segments, such as the TM domains, will not be sufficiently conserved to allow the collect folding, higher order structure or localization needed for HCV entry. For these reasons, precise swaps, alone and in combination, of the extracellular loops will also be made (FIG. 14B, iii and iv). To facilitate determination of transduction efficiency, expression level, and localization, these chimeras will be constructed as N-terminal GFP fusions as described above (see section D1a2) for CLDN1. As described in C3, 293T cells transduced with the CLDN1/7 chimeras will be used to measure their ability to promote HCV entry.

Further subdomain chimeras may allow a finer resolution mapping of functional CLDN1 determinants. Alternatively, site-directed mutagenesis of the CLDN1 domain of interest can be performed. For example, since the CLDN1 extracellular loops are only 53 and 24 amino acids, it would be straightforward to mutate these regions, initially in sets of five amino acids and eventually individually, to CLDN1 or CLDN7 residues (or alternative amino acids such as alanine) and test for entry function. Deletion mutants, of either entire loops or smaller portions of loops, will also be constructed and tested for their capacity to allow HCV entry.

A catalogue of insertional mutants throughout the CLDN1 region of interest were assembled (FIGS. 14, 15, 16, and 17). Such insertional mutants can be constructed in a defined manner, where a FLAG epitope sequence will be inserted every three to four amino acid residues. 293T cells will be transduced with each insertional mutant separately and then challenged with HCVpp. Mutants that disrupt HCV infection may reside in regions important for the interaction between CLDN1 and the virus. Furthermore, mutants that retain the ability to mediate HCVpp infection can be retested in the presence of an anti-FLAG monoclonal antibody (Sigma). If HCV needs to interact with an extracellular region of CLDN1, it would be conceivable that a site within CLDN1 that is capable of tolerating a small insertion may thus be turned into the epitope for an antibody that, if bound, could block a putative virus-CLDN1 interaction. Since we currently do not have antibodies directed against the extracellular loops of CLND1, these conditional CLDN1 mutants may prove important for additional studies proposed below. As an alternative to screening defined CLDN1 insertional mutants, a CLDN1 random insertion library can be constructed through a transposon based approach. We have previously used transposon-mediated mutagenesis to identify sites in the HCV NS5A protein where exogenous sequences, such as FLAG epitopes or GFP could be inserted as a fusion protein with minimal effect on replicon function (Moradpour et al., 2004, J Virol 78:7400-7409). 293T cells transduced with such a CLDN1 FLAG-transposed library can be selected with GFP or drug resistance carrying HCVpp. Those selected for HCVpp permissiveness can then be reselected for loss of HCVpp susceptibility in the presence of anti-FLAG antibody.

We also plan to investigate whether cellular functions reported for CLDN1 are important for HCV entry. While EL1 likely bridges the extracellular space by making hetero- and homo-typic interactions between claudins, the functions of EL2 seem more diverse. In CLDN3 and CLDN4 this smaller loop is the primary binding determinant for *Clostridium perfringens* enterotoxin binding. The intracellular regions of claudins contain putative protein kinase C (PKC), casein kinase II, and cyclic adenosine monophosphate (cAMP)-dependent kinase phosphorylation sites, modification of which may have consequences for TJ assembly. CLDN1 and many other claudins have a C-terminal PDZ domain-interacting motif, thought to interact with a variety of TJ components and intracellular signaling molecules. It will be interesting to test if disruption of specific CLDN1 motifs or sites of possible protein modification affect HCV entry. In particular, it will be important to determine if the interactions between CLDN1 and other TJ components are required for this function. If so, then one may speculate that the cellular mechanisms of TJ regulation and internalization may be utilized by HCV for cell entry. If so, CLDN1 mutants lacking this cellular function that maintain the ability to interact with HCV may function as dominant negative inhibitors of HCV entry in cells expressing wild type CLDN1.

CLDN1 levels should ultimately become limiting for HCV entry. To examine this, several approaches will be taken. Lentiviral transduction of CLDN1 should produce cell clones expressing a range of CLDN1 levels, mainly through variation in the copy number of integrated viruses and chromosome locus-dependent transcriptional activity. The functional GFP-CLDN1 fusion protein can be employed to facilitate monitoring of expression levels and protein localization. Such a population will be challenged with various moi's of a red fluorescent protein expressing HCVpp and subjected to dual-color FACS to determine if cells that express higher CLDN1 levels are more likely to be infected. In addition, GFP-CLDN1 can be sorted by expression level and used for HCVpp challenge as a population or after cloning to produce individual cell lines with different CLDN1 expression levels. Alternatively, a pTRIP provirus will be used where the internal cassette is expressed from a tetracycline regulated promoter (TRex system, Clontech) that can be used to infect the commercially available 293T cell lines expressing the tetracycline repressor. This system will allow doxycycline-mediated regulation of CLDN1 expression to investigate how this affects HCV permissiveness.

Figure 19:
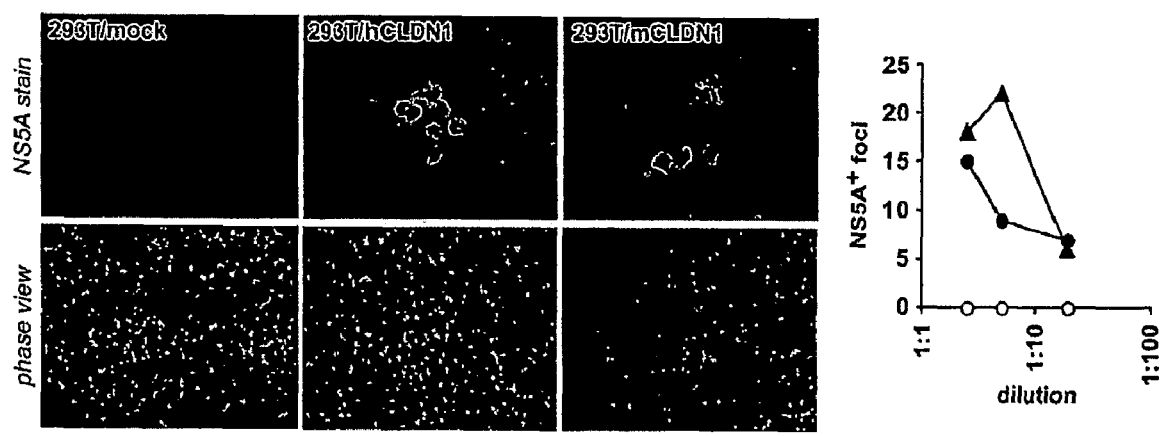

We have identified several cell lines that express CD81, SR-BI and LDL-R but are still resistant to HCVpp infection, which were candidates for a screen that eventually identified CLDN1. Thus far, we have seen a positive correlation between CLDN1 expression and HCVpp permissiveness; all permissive cells tested (Huh-7.5, Hep3B, HepG2/CD81) were CLDN1 positive and most non-permissive cell lines were CLDN1 negative (293T, SW13, HeLa, HepH). Upon CLDN1 transduction, the 293T and SW13 cell lines displayed a 63-fold and a 115-fold increase in susceptibility to HCVpp infection, respectively—the same level of susceptibility as highly permissive hepatoma cell lines (Huh-7.5, Hep3B). It is of interest that both mouse and human CLDN1 mediated HCVcc entry with comparable efficiency (FIG. 19).

The J6/JFH genotype 2A chimeric virus has been described (Lindenbach et al., 2005, Science 309:623-6) and we have established a technique for quantifying viral infectivity by limiting dilution assay and NS5A immunostaining (Lindenbach et al., 2005, Science 309:623-6). Additionally, a Renilla luciferase reporter, engineered in the backbone of the J6/JFH chimeric virus, termed FL-J6/JFH-5'C19Rluc2AUbi, has been used in studies of HCV entry (Tscherne et al., 2006, J Virol 80:1734-1741). We have also been able to generate chimeric H77/JFH HCVcc, which expresses the H77 envelope glycoproteins (M.E., unpublished data). Ex vivo HCVcc: We have obtained acute phase plasma and serum samples of HCVcc that have been passaged in either chimpanzees (chHCVcc) or SCID-uPA beige xenograft mice (muHCVcc) (Lindenbach et al., 2006, Proc. Natl. Acad. Sci. USA 103 In press). These ex-vivo samples are infectious in Huh-7.5 cells and provide a unique opportunity to compare the entry properties of functional virus produced in vivo with HCVcc and HCVpp. Soluble E2 and soluble E1E2: C-terminally truncated soluble E2 protein (sE2) is routinely generated in our lab by transfection of a sE2 expression construct into 293T cells and harvest of cell supernatants (Flint et al., 2000, J Virol 74:702-9). Expression constructs for generating E1E2 and methods for purifying large quantities of cell-associated E1E2 complexes have been described (Brazzoli et al., 2005, Virology 332:438-53; Frey et al., 2005, Presented at the 12th International Symposium on Hepatitis C Virus and Related Viruses, Montreal, Canada, October 2-6). Purified material for use in blocking experiments will be provided by Michael Houghton (Chiron).

Permissive cells: Huh-7.5 cells are permissive for HCVpp, HCVcc, chHCVcc, and muHCVcc infection and therefore possess all of the necessary factors for HCV entry. We also have characterized a battery of cell types, including HepG2 and 293T cells which are non-permissive for HCV infection, but become permissive when transduced with a particular entry factor, like CD81 or CLDN1, respectively.

To analyze the specific roles of CD81, SR-BI/II, and CLDN1 in HCV entry, we will make use of blocking reagents in the form of antibodies, peptides, and soluble forms of protein molecules, as described below.

CD81: GST-CD81 large extracellular loop (LEL) and anti-CD81 antibodies (Santa Cruz 1.3.3.22 and BD Pharmingen JS81, respectively) are established blocking reagents and readily available (Cormier et al., 2004 et al., Proc Natl Acad Sci USA 101:7270-4; Hsu et al., 2003, Proc. Natl. Acad. Sci. USA 100:7271-76; Lindenbach et al., 2005, Science 309: 623-6) (unpublished data).

SR-BI/II: We have obtained a stable CHO cell line that expresses a recombinant, soluble form of the SR-B1 extracellular domain (SR-B1-EC) fused to a C-terminal FLAG-epitope tag (Heo et al., 2004, J Immunol 173:446-55). SR-B1-EC can be purified from cell lysates using an M2 anti-Flag-agarose column (Sigma) and will be tested for inhibitory activity against HCVpp and HCVcc.

CLDN1: Blocking antibodies directed against the CLDN1 extracellular loops will be obtained.

A straightforward approach to begin to address the sequence of virus-host cell interactions is to bind virus on ice and then shift to 37° C.; the blocking reagents described above that target different entry factors will be added at defined time points (during binding on ice, at the time of the temperature shift, or at various time points thereafter) and the infection signal recorded as a percentage of the signal in the absence of blocking reagents. A time course of antibody or peptide addition after shifting to 37° C. can be used to dissect the virus-receptor and receptor-receptor interactions occurring at each stage of the HCV entry process. For example, after HCV binding on ice, an antibody recognizing CLDN1 or a CLDN1 derived peptide with blocking activity corresponding to CLDN1 EL1 could be added to the cells at the time of shifting to 37° C. and at defined later time points, to determine to what extent they perturb entry. The same experiment could be performed with reagents targeting CD81 or SR-BI/II. A blocking reagent is likely to lose activity after its target molecule has interacted with the virus. Hence a reagent targeting an early event in the entry process should become ineffective earlier than one targeting a later step. Thus using the blocking agents in various combinations at distinct timepoints at/after shifting to 37° C. will allow the development of a temporal model of virus-entry molecule interactions during HCV entry.

Figure 20:
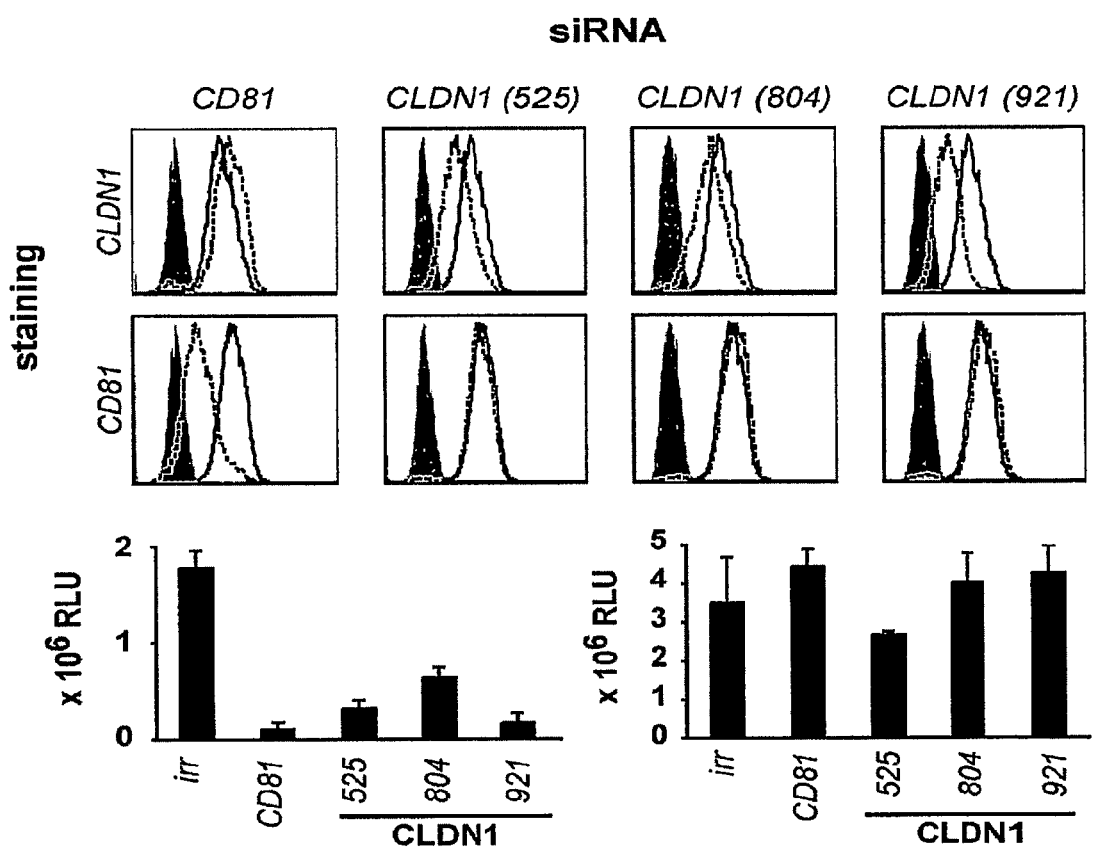

Use of siRNA for the silencing of CLDN1 expression in Hep3B cells specifically inhibited HCVpp (FIG. 20).

To examine parameters affecting virus binding to a target cell with regard to CD81, SR-BI/II, and CLDN1, we will establish a virus-binding assay. Cells expressing a variety of entry factors will be incubated with HCVcc on ice for a defined time period, after which, the amount of cell-associated HCV RNA will be determined using real-time quantitative RT-PCR assay (Lindenbach et al., 2005, Science 309: 623-6).

As the ability of HCV to bind and stay bound to cells may be determined not by just one receptor molecule but rather a combination of factors including ones that we are as yet unaware of, we will take a number of approaches to examine the requirements for HCV binding. (1) Non-human, non-permissive cells, such as CHO cells can be transduced with constructs expressing CD81, SR-BI/II, and CLDN1, alone or in combination and assayed for HCV binding. (2) 293T cells, used in the screen that identified CLDN1 as an HCV receptor described above, are non-permissive for HCV infection but become permissive when transfected with CLDN1 cDNA. 293T cells and 293T-CLDN1 cells can therefore be used to look specifically at the contribution of CLDN1 to HCV binding. A similar approach has been taken to determine that the contribution of CD81 to HCVpp binding to HepG2 cells is low, making it an unlikely initial attachment receptor (since this cell line is fully HCV permissive when transduced with CD81 yet HCVpp binding is not affected (Cormier et al., 2004 et al., Proc Natl Acad Sci USA 101:7270-4)). (3) Using permissive cells, such as Huh-7.5 cells, we will examine the effect of incubation prior to HCV binding with CD81, SR-BI/II, and CLDN1 antibodies, described in D3a, individually or in concert. The binding assay will also be performed using virus that has been incubated with peptides targeting distinct regions of CD81, SR-BI/II, and CLDN1, or soluble forms of these receptor molecules where available. (4) Binding of sE2 or soluble E1E2 heterodimers to any of the above-mentioned cell-types may be another tool to study which molecules can function as receptors in mediating virus attachment.

We will establish an assay to look specifically at the HCV glycoprotein mediated membrane fusion and determine which entry molecules are required for this late step. We will pursue a variety of approaches: (1) HCVpp fusion with liposomes. A recent report describes an HCV fusion assay based on rhodamine (R18) fluorescence dequenching (Lavillette et al., 2005, J Biol Chem). In this assay, fusion of HCVpp with liposomal membranes was observed with fluorescent probes incorporated into either HCVpp or the liposome. HCV gp-mediated fusion was shown to be pH- and temperature dependent. Surprisingly fusion did not require the presence of any protein or receptor on the liposome surface. However, the extent and kinetics of fusion were decreased compared to influenza HApp mediated fusion in the same assay. The authors speculate that HCVpp fusion may be suboptimal in the absence of receptor on the target membrane. Hence, this system requires further investigation, but it does provide a basis for the generation of an effective HCV fusion assay. (2) HCVgp based cell-cell fusion assay. HCV glycoproteins are mainly retained in the ER, although some E1 and E2 escape ER retention and transit to the cell surface (Bartosch et al., 2003, J Exp Med 197:633-642; Drummer et al., 2003, FEBS Lett 546:385-90; Flint et al., 2004, Virol 78:6875-82). This observation formed the basis for a recently reported cell-cell fusion assay (Kobayashi et al., 2006, J Virol 80:1817-1825) that requires two cell populations: 293T effector cells that express the HCV envelope gps and a T7 promoter-driven GFP sequence, and target cells, such as Huh-7.5 cells, which express the T7 RNA polymerase. Fusion of these two cell populations actives expression of the GFP reporter. Similar assays using various reporters have been previously described for a number of viruses including retroviruses, rhabdoviruses, and herpesviruses (Albright et al., 1998, J Neurovirol 4:486-94; Davis-Poynter et al., 1994, J Virol 68:7586-90; Riedel et al., 1984, EMBO J 3:1477-83; Rucker et al., 1997, Methods Enzymol 288:118-33). (3) HCV gp based cell fusion assay to study sequential receptor interactions. To study the sequential interaction of HCV with its receptors, we can use a variation of the HCV gp based cell fusion assay described in (2). A recombinant soluble receptor, GST-CD81 or GST-CLDN1 for example, can be preincubated with effector cells prior to incubation with target cells. The effector cells will then be incubated with target cells containing the additional receptors but lacking CD81 or CLDN1, respectively. If interaction with the soluble receptor is required prior to interaction with the additional receptors, fusion should theoretically be catalyzed by the presence of such a factor in the media. This assay has been used previously to demonstrate that soluble CD4 can activate HIV Env for coreceptor-dependent fusion (Salzwedel et al., 2000, J Virol 74:326-33).

Figure 18:
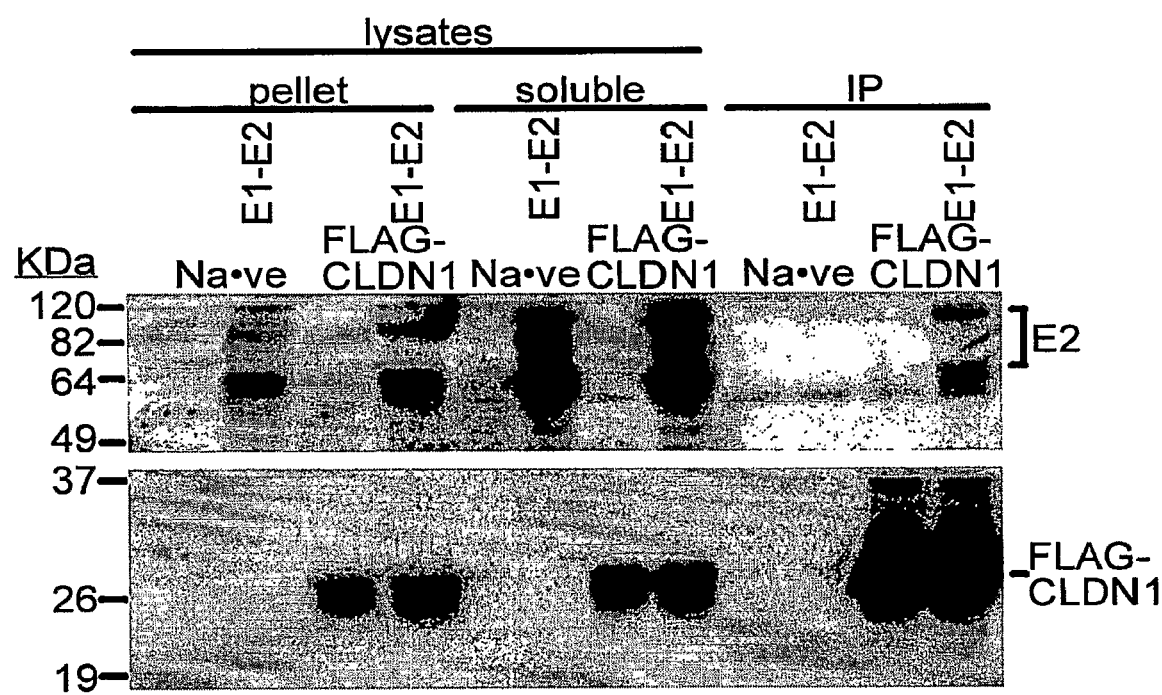

To examine physical interactions between viral envelope proteins and entry factors, we will first perform a series of co-immunoprecipitation assays (co-IP). A straightforward approach is to attempt anti-FLAG coIPs of the factors of interest with FLAG epitope tagged versions of a putative interaction partner. Functional versions of FLAG tagged CLDN1 (see section D1a2) and E2 (unpublished data) have been generated and successfully tested. We propose to expand the arsenal of reagents by generating intracellularly tagged SR-BI/II and CD81. In the past we have shown that a chimera where the CD81 LEL was introduced into the related tetraspanin CD9 (that does not function as an HCV entry factor) was fully functional for HCV entry (Zhang et al., 2004, J Virol 78:1448-55). This finding is encouraging for generating a functional tagged CD81. Tagged SR-BI has also been reported (Reaven et al., 2004, J Lipid Res 45:513-28). Tagged HCV entry factors can be employed to coIP a variety of target molecules, including overexpressed or endogenous host proteins, HCVcc virus, overexpressed E1, E2 and E1/E2, and the soluble versions of the envelope proteins, sE2 and sE1E2. Using such an approach, we have demonstrated an interaction between HCV E2 and CLDN1 by immunoprecipitating lysates from cells expressing FLAG-CLDN1 and E1E2 (FIG. 18). We intend to attempt similar FLAG-CLDN1 coIPs of endogenous CD81 with or without E1E2, E1 expressed alone, and E2 expressed alone. After optimization of conditions it may also be possible to analyze the formation of virus-receptor and receptor-receptor complexes in real-time by doing a time course of IP after virus or sE1/E2 binding.

To discern the late entry events that occur after the virus has left the cell surface, we have examined the role of cholesterol and the cellular uptake pathways (clathrin, caveolin or another pathway) in HCV entry. The results from these experiments can be used to guide and enhance some of the studies described above for cellular entry molecules. Two approaches will be undertaken: (1) Role of cholesterol in the target membrane. To determine the role of cholesterol in the target membrane for HCV fusion we will use the cholesterol-depleting drug, methyl-β-cyclodextrin (MβCD). MβCD has been used to demonstrate the role of cholesterol in the entry pathway of a number of viruses, including vaccinia (Chung et al., 2005, J Virol 79:1623-34), influenza (Sun et al., 2003, J Virol 77:12543-51), and polioviruses (Danthi et al., 2004, J Virol 78:33-41). Cells will be treated with MCD and subsequently infected with HCV. As a control, cholesterol will be added back to the MβCD-treated cells to determine if virus infection can be restored. If cholesterol is required, it will be of interest to examine the effects of cholesterol depletion on the cell-surface expression and localization of HCV entry factors (are these molecules present in a lipid raft-associated complex that is dissociated by MβCD treatment?) (2) Role of clathrin-mediated endocytosis. Various reagents exist to perturb clathrin-mediated endocytosis. We have acquired dominant-negative forms of proteins required for clathrin pit formation, such as AP180 and Eps15 (Benmerah et al., 1999, J Cell Sci 112 (Pt 9):1303-11; Ford et al., 2001, Science 291: 1051-5). We will test these for their ability to inhibit HCV infection. We will also use siRNAs targeting clathrin heavy chain (CLTC) to determine if HCV requires this route for productive entry. As a control for these experiments we will use Sindbis virus, a well-characterized alphavirus that enters cells through clathrin-mediated endocytosis. Huh-7.5 cells do not express caveolin (Ford et al., 2001, Science 291:1051-5), hence this pathway is not likely to be involved in HCV entry, at least in this cell type.

Example 2

CLDN1 Expression is Associated with Susceptibility to HCVpp in Human Cell Lines

Figure 21:
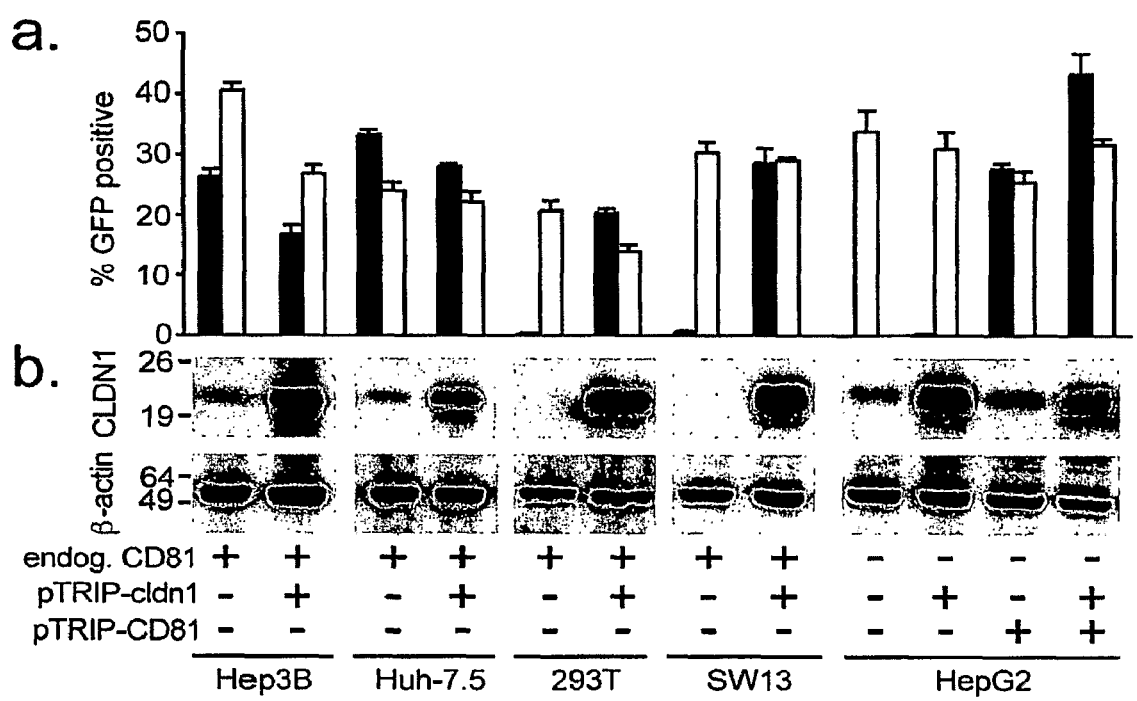

To test whether CLDN1 expression correlates with permissiveness for HCV entry, we surveyed the HCVpp susceptibility (FIG. 21) and CLDN1 expression level (FIG. 21) for human cell lines pre- and post-transduction with CLDN1 expression vectors. 293T, HeLa, Hep3B, Hepa1.6, HepG2, HepH, Huh-7.5, SW13 and TZM cells were maintained in DMEM with 10% fetal bovine serum (FBS). HepG2 were grown on collagen coated plastic. The HCVpp susceptible Huh-7.5 and Hep3B human hepatoma cell lines expressed endogenous CLDN1 and overexpression of CLDN1 in these cells did not enhance HCV entry. Two HCVpp-resistant non-hepatic cell lines, 293T and SW13, did not express detectable levels of endogenous CLDN1, but became highly susceptible to HCVpp on CLDN1 expression. The CD81-negative hepatoma HepG2 line, previously reported to become susceptible on CD81 expression, also expressed endogenous CLDN1 and HCVpp entry remained CD81-dependent even when CLDN1 was overexpressed. However, the human HeLa and HepH cell lines (both CD811 SR-BI1 CLDN12) remained HCVpp-resistant when overexpressing CLDN1.

Likewise, expression of human CLDN1 and/or CD81 in non-human cell lines did not allow HCVpp entry. Moreover, murine CLDN1 (90% amino acid identity to human) efficiently supported HCV entry, indicating that CLDN1 is not a determinant of species host range (FIG. 19). These observations suggest that one or more human specific HCV entry factor(s) remain to be discovered.

Example 3

HCVpp Susceptibility Depends on Residues in the First Extracellular Loop of CLDN1

Figure 15:
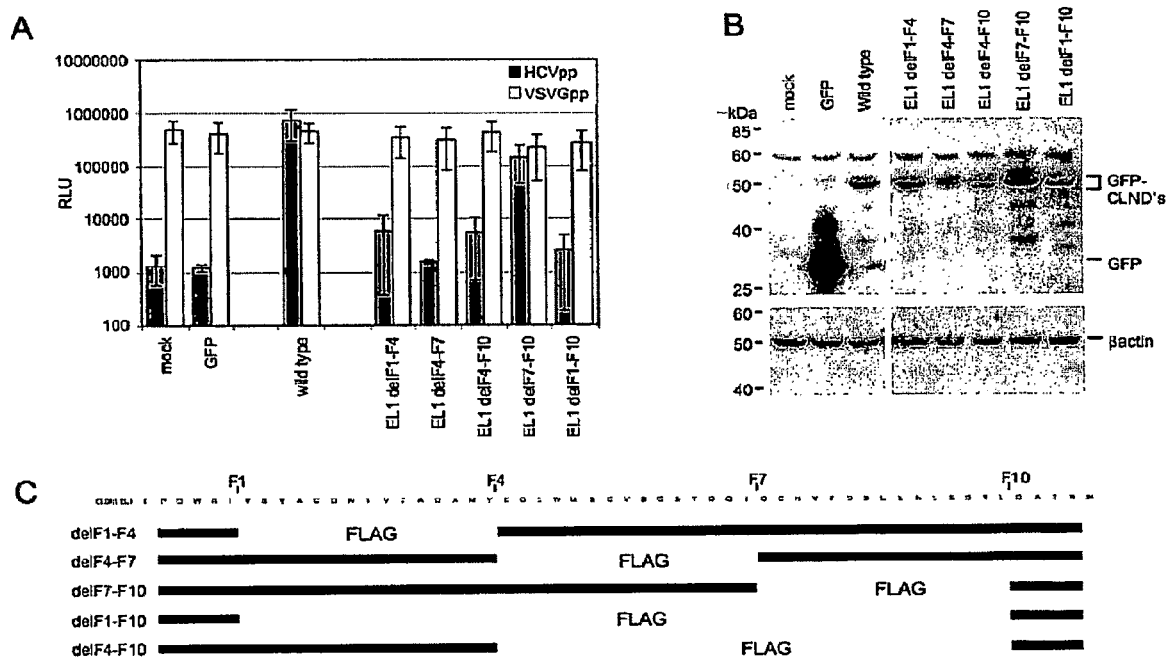
FIG. 15. Deletions within the first two-thirds of CLDN1 EL1 disrupt HCV entry. To further define regions of CLDN1 required for HCV infectivity CLDN1 encoding deletions of EL1 were tested for abilities to mediate HCVpp entry. (A) 293T cells transduced to express GFP-CLDN1 with regions of EL1 deleted and replaced with the FLAG epitope sequence (as shown in C), were tested for permissivity to either HCVpp (graph bars) or VSVGpp (white bars) encoding the luciferase reporter gene. Each value is the mean of three independent infections assayed 48 hpi with error bars representing one standard deviation. As shown, only wild type CLDN1 and EL1delF7-10 expression results in HCVpp permissivity. (B) All GFP-CLDN1 deletion clone proteins were similarly expressed. Total cellular protein lysates were prepared from transduced 293T cells, resolved by SDS-PAGE gel electrophoresis, transferred to nitrocellulose membrane, and immunoblotted with an anti-GFP (top) or β-actin (bottom) mouse monoclonal antibody. (C) Illustration of deletions within CLDN1 EL1 (SEQ ID NO:1, residues 28-81) tested above.
Figure 16:
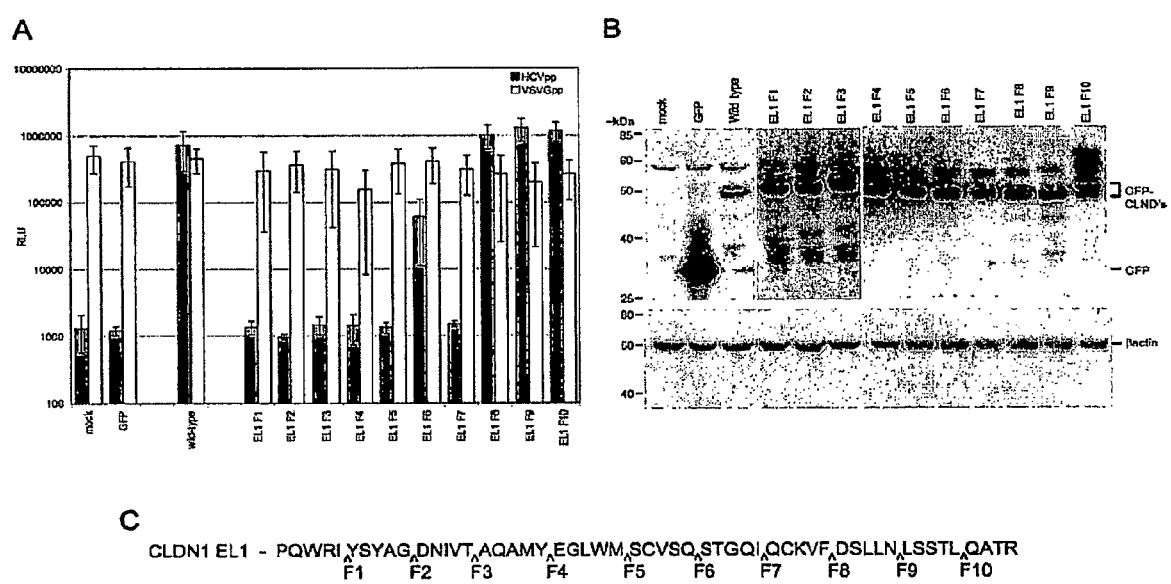
FIG. 16. Deletions within the first two-thirds of CLDN1 EL1 disrupt HCV entry. To further define regions of CLDN1 required for HCV infection CLDN1 encoding insertions within EL1 were tested for abilities to mediate HCVpp entry. (A) 293T cells transduced to express GFP-CLDN1 with the FLAG epitope sequence inserted every five amino acids within EL1 (F1-F10) (as shown in C), were tested for permissivity to either HCVpp (graph bars) or VSVGpp (white bars) encoding the luciferase reporter gene. As shown, only wild type CLDN1, and EL1 F6 (partially), F8, F9, and F10 expression results in HCVpp permissivity. (B) All GFP-CLDN1 EL1 FLAG insertion clone proteins were similarly expressed. Total cellular protein lysates were prepared from transduced 293T cells, resolved by SDS-PAGE gel electrophoresis, transferred to nitrocellulose membrane, and immunoblotted with an anti-GFP (top) or β-actin (bottom) mouse monoclonal antibody. (C) Illustration of FLAG insertions within CLDN1 EL1 (SEQ ID NO:1, residues 28-81) tested above.
Figure 17:
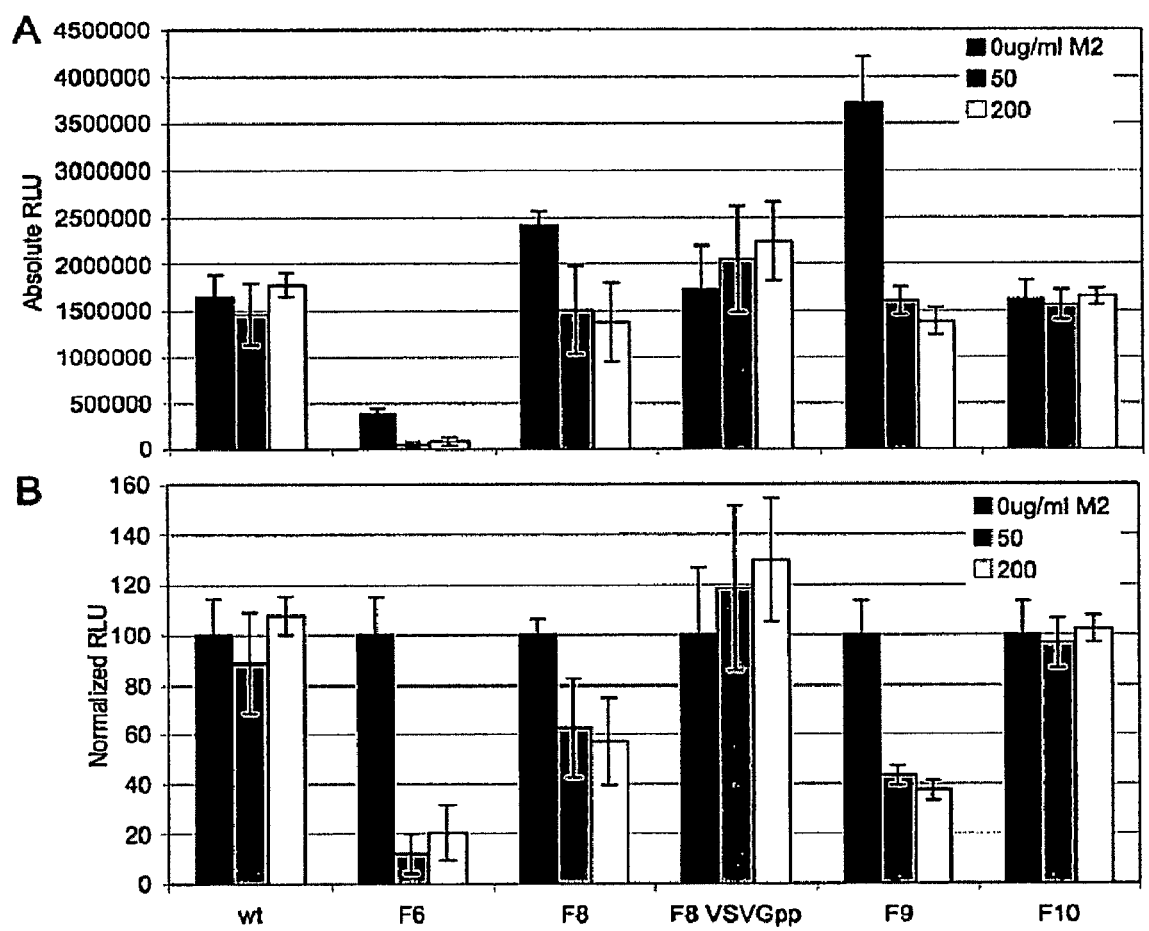
FIG. 17. CLDN1 with epitopes insertions within EL1 can be blocked by epitope specific antibodies. To selectively inhibit CLDN1 function, epitope inserted CLDN1 constructs that remain functional for HCV entry were tested for HCVpp infectivity in the presence of anti-FLAG antibodies. 293T cells expressing GFP-CLDN1 proteins with FLAG insertions within EL1 that maintain the ability to promote HCV entry were preincubated (1 h, 37 C) with media containing the indicated concentration of anti-FLAG M ponents. Claudin 14 has been shown to be palmitoylated on cysteine residues proximal to the second and fourth transmembrane domains (Chen, Y., et al. 1997 Nat Med 3:L866-71). Such modifications may regulate protein interactions or direct the molecule to specific regions of the plasma membrane. These residues are conserved between claudins, suggesting this modification is universal throughout the claudin family. Putative palmitoylation sites were disrupted by mutation of cysteines to serines (locations indicated by C-S mt 1=C104, 107S and C-S mt 2=C183, 184, 186S). (B) 293T cells transduced with lentiviruses to express the indicated GFP-CLDN1 mutants were challenged with either luc-HCVpp (black bars) or VSV-Gpp (white bars). Three days post infection cells were lysed and luciferase assays were performed. RLU readings were normalized to those obtained in 293T cells expressing wild type CLDN1 (as shown in FIG. 5a). Values are the mean+/−s.d. of n=4 independent infections of at least two independently transduced populations. While both deletion of the carboxyl-terminal intracellular tail or mutation of both putative palmitoylation sites impaired HCVpp infection by about three-fold each, all mutants were still able to support HCV entry, indicating that these features are not absolutely required for this process.
Figure 22:
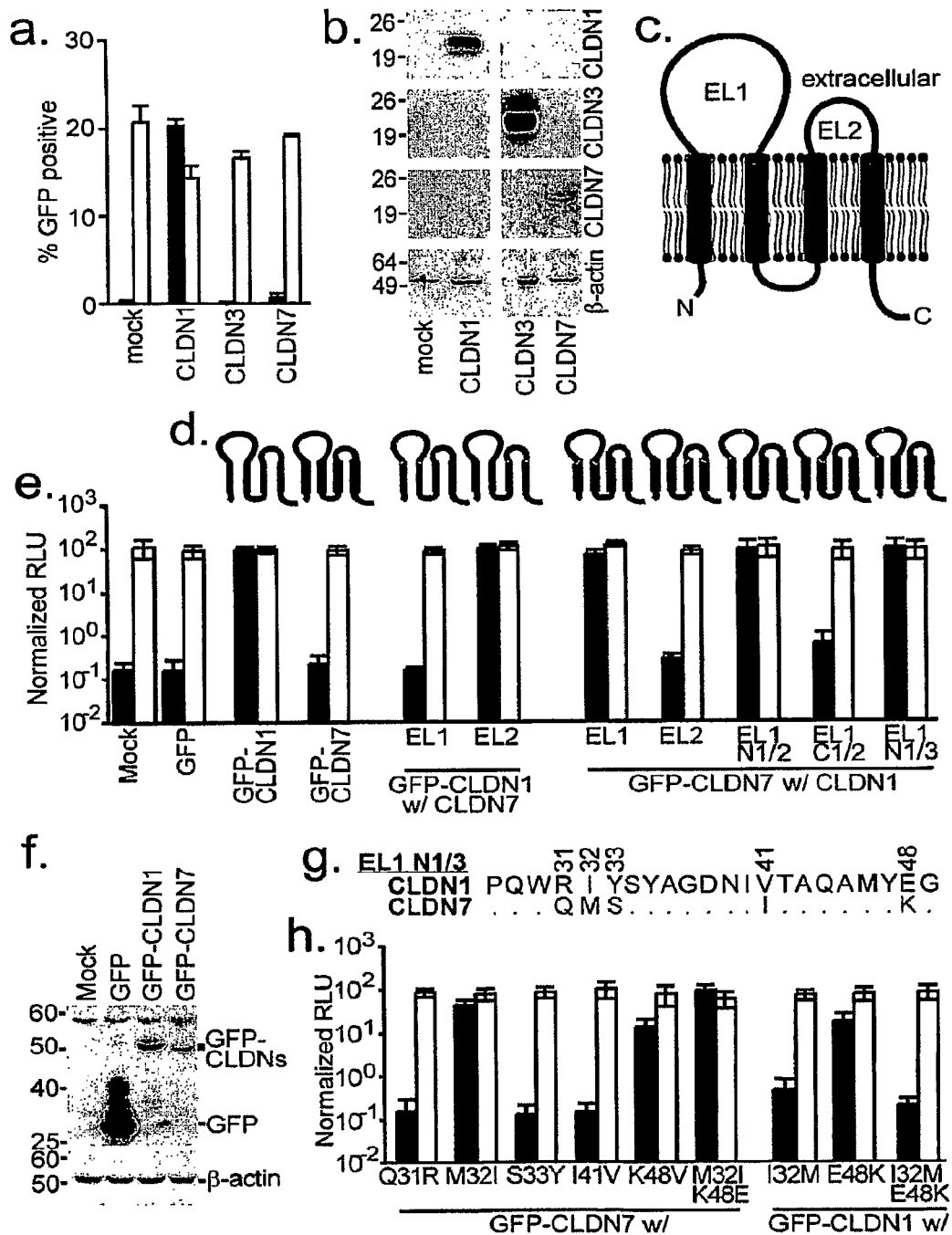
Figure 24:
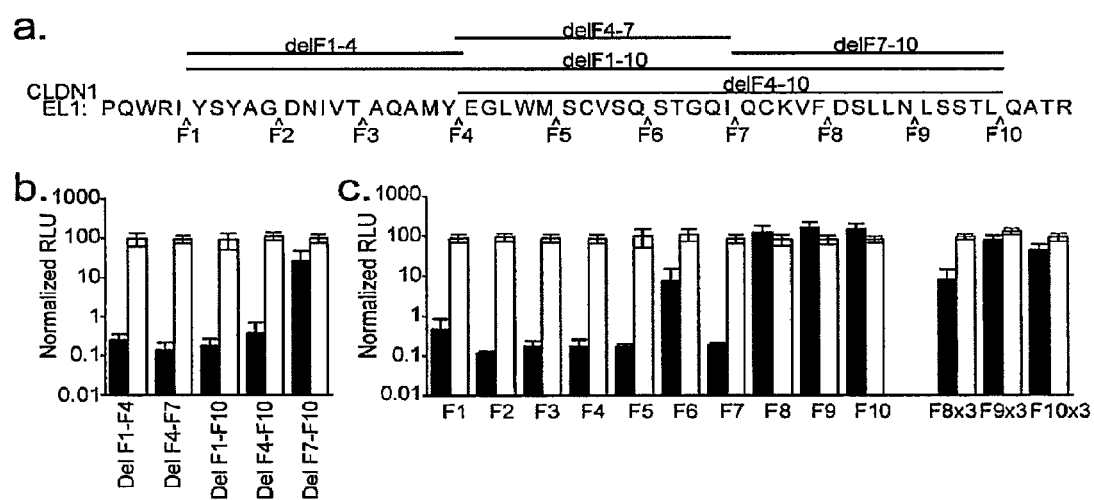
FIG. 24. Mutational analysis of CLDN1 domains required for HCV entry functions. (A) Illustration of CLDN1 EL1 deletion and insertion mutants. Lines above the CLDN1 EL1 sequence represent regions that were deleted. Arrowheads below the sequence indicate the position of individual FLAG epitope insertions (B, C). 293T cells transduced with lentiviruses to express the indicated GFP-fusion deletion (B) and insertion (C) mutants were challenged with either luc-HCVpp (black bars) or VSV-Gpp (white bars). Three days post infection cells were lysed and luciferase assays were performed. RLU readings were normalized to those obtained in 293T cells expressing wild type CLDN1. Values are the mean+/−s.d. of n=4 independent infections of at least two independently transduced populations. (B) 293T cells expressing CLDN1 mutants with deletions of the majority of EL1 (delF1-10) or only the first (delF1-4) or middle (delF4-7) third were not injectable with luc-HCVpp, while deletion of the last third of EL1 (delF7-10) left the HCV entry function of CLDN1 at least partially intact (26% of CLDN1). VSV-Gpp entry was unaffected in all cases. (C) Insertion of an individual FLAG epitope at any position within the first 40 amino acids of GFP-CLDN1 EL1 (positions F1-F7), see (A) largely abrogated the HCV entry function of CLDN1, with only the insertion at position 6 (F6) being minimally permissive (7.5% of wild type CLDN1). In contrast, a single FLAG epitope tag could be inserted within the last 20 amino acids of EL1 (positions F8-10) without impairing, and in fact slightly improving, the HCV entry function of CLDN1. When triple FLAG epitopes were inserted in these last three positions (F8-10x3) the F8 position was only minimally permissive (7.9% of wild type CLDN1), while triple FLAG insertions at positions F9 and F10 remained functional for mediating HCVpp infection (78 and 43% of wild type CLDN1, respectively).

Of the other claudin family members, neither CLDN7, the closest relative of CLDN1 (60% amino acid identity), nor CLDN3, the closest liver-expressed relative (49% identity), rendered 293T cells permissive to HCVpp (FIG. 22), despite high levels of protein expression (FIG. 22*b*). To map CLDN1-specific entry determinants, we analyzed a series of CLDN1-CLDN7 chimaeras (FIG. 22*d*) fused to the carboxyterminus of GFP. The parental fusion proteins functioned identically to untagged proteins (FIG. 22*e*) and were expressed similarly (FIG. 22*f*). The expression and membrane-localization of all mutants were confirmed by flow cytometry and confocal microscopy, respectively (data not shown). CLDN1 is a 211 amino acid protein with four transmembrane helices, intracellular amino and carboxy termini and two extracellular loops (FIG. 22*c*). When extracellular loops were exchanged between CLDN1 and CLDN7 (FIG. 22*d*) it was found that only those containing the CLDN1 EL1 enhanced HCVgp-dependent infection (FIG. 22*e*). Progressively smaller exchanges identified the N-terminal third of the CLDN1 EL1 (EL1 N1/3) to be sufficient in an otherwise CLDN7 background to confer full susceptibility to HCVpp entry in 293T cells (FIG. 22*e*). The importance of CLDN1 EL1 in HCVpp entry was confirmed by deletion and insertional mutagenesis (FIG. 15 and FIG. 24).

Figure 23:
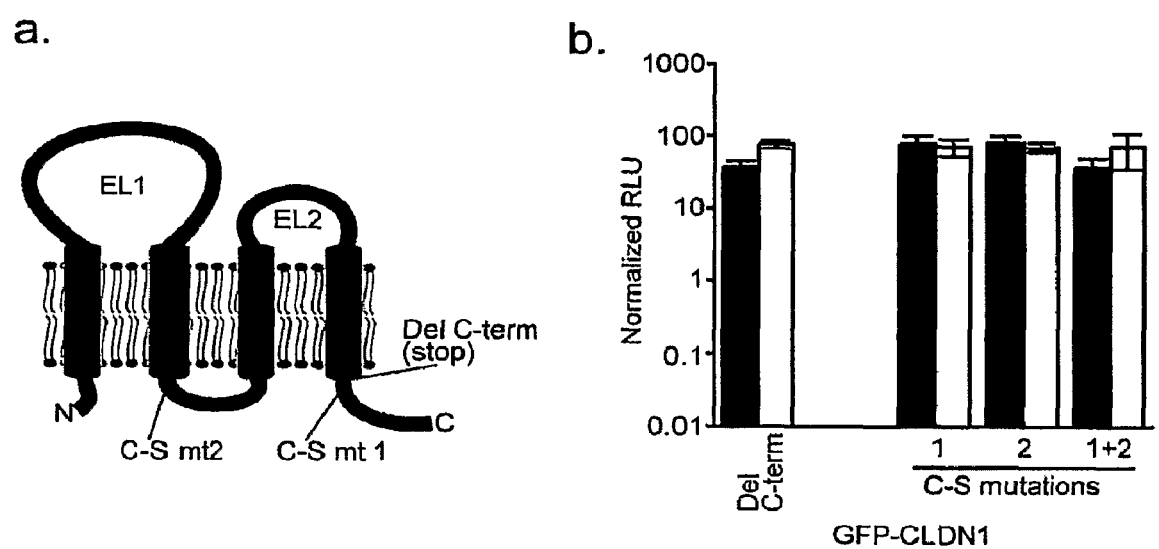

Five residues differ between CLDN1 and CLDN7 in the critical region of EL1 (FIG. 22*g*). Although changing three of these in CLDN7 to the corresponding CLDN1 sequence had no effect, introduction of M32I or K48E into CLDN7 rendered 293T cells partially HCVpp permissive (46% and 14% of wild-type CLDN1, respectively; FIG. 22*h*) and the combination of both changes supported HCV entry as efficient as wild-type CLDN1. Conversely, introduction of I32M or E48K into CLDN1 dramatically reduced HCVpp susceptibility, and the presence of both mutations reduced entry to background levels (FIG. 22*h*). None of the wild-type or mutant claudin molecules affected VSV-Gpp entry (FIG. 22*h*). These data suggest that any CLDN1 features required for HCV infection other than I32 and E48 must be conserved between CLDN1 and CLDN7. In additional analyses, we found the CLDN1 C-terminal intracellular tail, which mediates interactions with other TJ proteins 18, and putative palmitoylation sites, which may regulate protein interactions or direct the molecule to specific regions of the plasma membrane (Bartosch, B., et al. 2003 J Exp Med 197:633-342), were not required for HCVpp entry (FIG. 23). This suggests a direct involvement of CLDN1 in HCV entry through an extracellular interaction rather than an indirect effect mediated through intracellular interactions with other tight junction components. All claudin mutants were also tested in SW13 cells with similar results (data not shown), confirming that the observed phenotypes were not 293T cell specific.

Example 4

Figure 25:
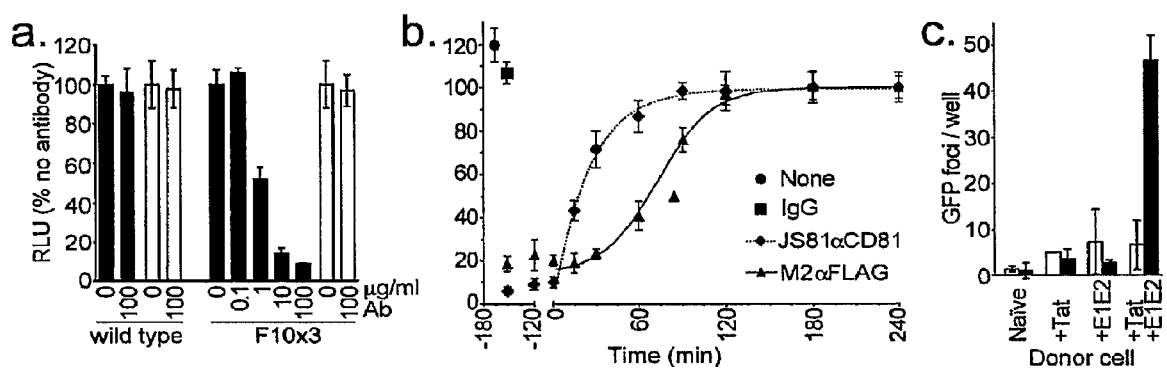
FIG. 25. Analysis of CLDN1 function in the HCV entry process. (A) 293T cells expressing wt or F10x3 CLDN1 were challenged with HCVpp (black) or VSV-Gpp (white) in the presence or absence of M2 anti-Flag. (Values normalized to no antibody; mean of n=4, error bars represent s.d.). (B) Synchronized infections were performed on 293T cells expressing F10x3 CLDN1 with the indicated antibodies being present from the time indicated on the x-axis. Values (% Entry) are relative to the signal seen when antibody was added 4 h post temperature shift. Controls are normalized to the value for M2 added at 4 h (all n=12). Fits of t=0 and later data points represent a one phase exponential association and sigmoidal dose-response (variable slope) for JS81 and M2, respectively. (C) Cell fusion assay using 293T acceptor cells expressing Tat-regulated GFP as well as mock (white) or CLDN1 (black), in co-culture with 293T donor cells expressing mock, HIV-1 Tat, HCV E1E2, or both (mean of n=3, error bars represent s.d.).
Figure 26:
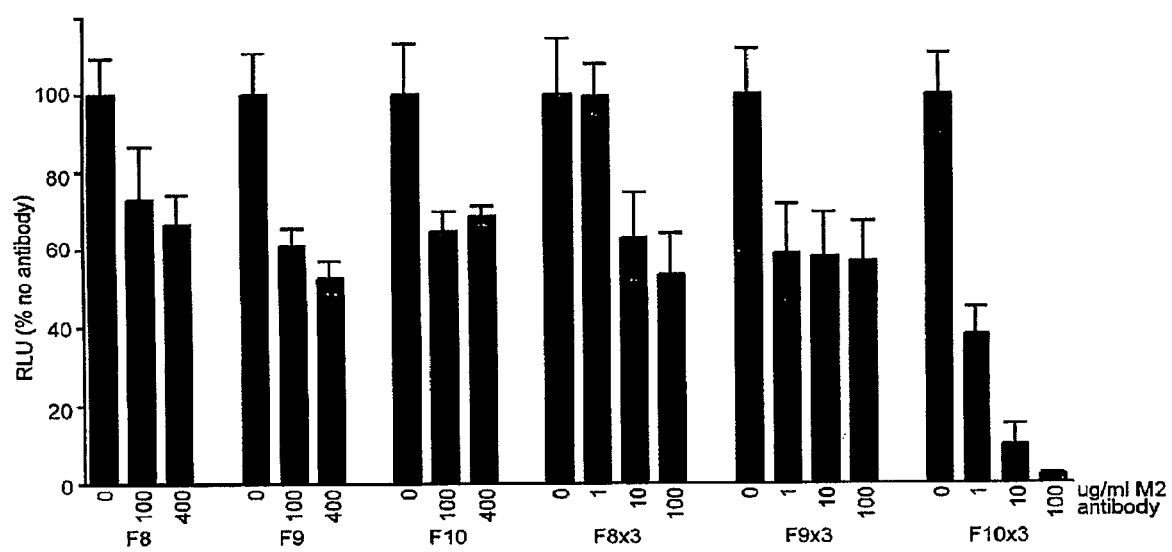
FIG. 26. Identification of CLDN1 EL1 epitope insertion mutants that allow antibody blocking of HCV entry. 293T cells transduced to express the indicated CLDN1 FLAG epitope insertion mutants were preincubated with increasing concentrations of anti-FLAG M2 monoclonal antibody for 30 min at 37° C.
Figure 28:
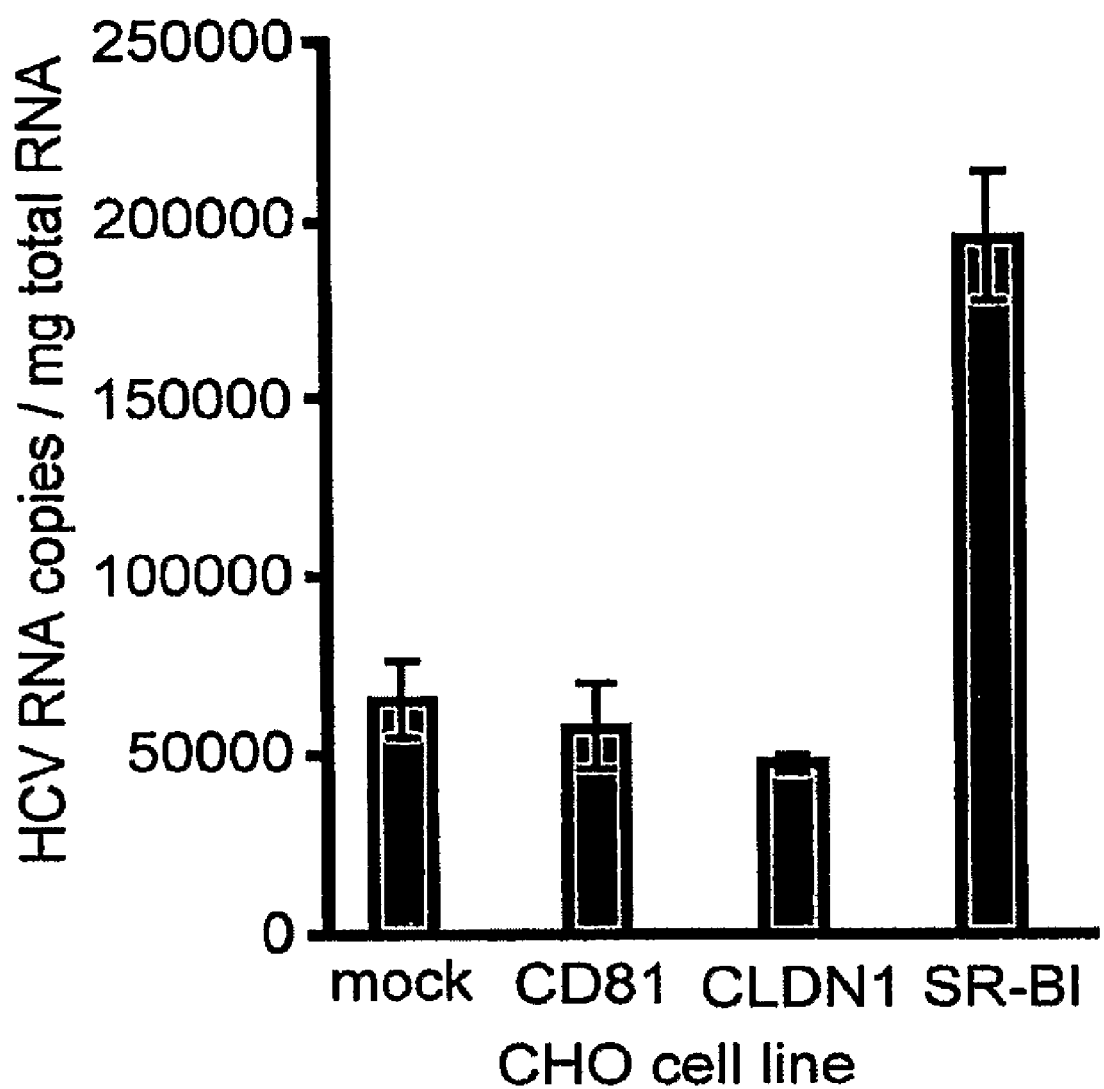

Blocking Antibodies, Ligands or Antagonists are Useful for Probing the Function of Cellular Molecules Involved in Viral Entry Unfortunately, all available CLDN1-specific antibodies recognize the intracellular C-terminal segment of the protein and are thus not useful for such studies. After an unsuccessful attempt to raise antibodies against CLDN1 EL1 (data not shown), we identified a site in the C-terminal portion of CLDN1 EL1 where a triple Flag epitope sequence could be inserted without seriously impairing HCV entry (FIG. 25, FIG. 26). HCVpp infection of 293T cells expressing this mutant (CLDN1 F10×3) was blocked in a dose-dependent manner by anti-Flag M2 monoclonal antibody. As controls, neither HCVpp infection of cells expressing wild-type CLDN1 nor VSV-Gpp infection of cells expressing CLDN1 F10×3 were affected by equal amounts of antibody. Although these results further suggest that CLDN1 functions in HCV entry through a direct interaction between EL1 and the virion, evidence for direct HCV binding to CLDN1 is lacking. In fact, HCVcc binding to CHO cells was only enhanced by expression of human SR-BI, but not CLDN1 or CD81 (FIG. 28). However, virus-receptor interactions before CLDN1 engagement may trigger HCV glycoprotein conformational changes required for CLDN1 binding, paralleling the situation with HIV-1 and its co-receptor CCR-5, in which binding requires prior interaction with CD4 (Wu et al., 1996, Nature 384, 179-83). To determine when CLDN1 functions in HCV entry, we examined the ability of the M2 antibody to block infection of CLDN1 F10×3 cells when added at various times during cell entry. To synchronize infection, 293T cells expressing CLDN1 F10×3 were incubated with HCVpp for 2 h at 4° C., so that virion binding but not entry could occur, and then washed and shifted to 37° C., allowing the infection to continue. Antibodies directed against both CD81 (JS81) and the Flag epitope (M2) inhibited HCVpp infection and retained maximal inhibitory activity even after the temperature shift to 37° C., indicating that like CD81 (ref. 10), CLDN1 acts at the post-binding stage of HCV entry (FIG. 25*b*). However, the inhibitory activity of anti-CD81 was lost much earlier than that of anti-Flag (half-maximal inhibition at 18 and 73 min post temperature shift, respectively), suggesting a sequence of events in which CD81 acts prior to CLDN1 in HCV entry.

Example 5

Cell-Cell Fusion Assays

To test if CLDN1 is required for HCVgp mediated membrane fusion we used a cell-cell fusion assay where 293T "acceptor" cells, encoding a HIV-1 transactivator of transcription (Tat)-dependent GFP, were cocultured with Tat-expressing "donor" cells such that fusion between donor and acceptor cell membranes results in enhanced GFP expression (FIG. 25*c*, and FIG. 27). To create acceptor cells capable of responding to fusion with a Tat-expressing cell, 293T cells were transduced with V1dTat-GFP-VSV-Gpp. From this population, cell clones were isolated that expressed little to no GFP in the absence of Tat, but had a high reporter signal when infected with V1 VSV-Gpp, which expresses Tat. GFP expression was quantified by flow cytometry as described above. Two clones that exhibited the tightest Tat regulation of GFP expression were used in parallel analyses with equivalent results (data not shown). To test the effects of CLDN1 in this assay, the acceptor cell clones were transduced with TRIP-mCherryCLDN1 VSV-Gpp, which renders 293T cells susceptible to luc-HCVpp (data not shown).

To create donor cell populations, 293T cells, seeded in a 6-well plate, were transfected with either mock V1 vector, to provide Tat expression, a glycoprotein expression vector (either H77 HCV E1E2 or VSV-G), or V1 plus glycoprotein. Transfections were performed with Fugene-6. At 36 h post transfection, combinations of donor and acceptor cells were co-seeded ($1.5 \times 10^6$ cells each/well) in 2-well chamber slides (BD Falcon). 12 h later, cells were washed with citric acid buffer at either pH 5 or pH 7 (15 mM citric acid, 150 mM NaCl), followed by media to neutralize the pH, and incubated for an additional 36-48 h. Slides were fixed with 2% w/v paraformaldehyde and mounted with 80% glycerol. Green foci were enumerated by eye using a Nikon Eclipse TE300 fluorescent microscope. Averages of three replicate experiments are shown with error bars representing the standard deviation. When using donor cells expressing HCV E1E2 expression of CLDN1 on the acceptor cells resulted in a seven-fold increase in the number of GFP-positive foci per well ($p<0.001$ by unpaired t-test), indicating a significant enhancement of HCVgp dependent cell-cell fusion (FIG. 25c). A pH 5 wash did not significantly increase the number of GFP foci observed, but changed their appearance from clusters of discrete GFP-positive cells to large brightly GFP-positive syncytia indicating that the pH-dependence of HCVgp mediated fusion 1-6 is maintained in this assay (FIG. 25). These results demonstrate that CLDN1 is required for HCVgp-dependent cell fusion although it is presently unclear whether it participates directly in the fusion process or acts at an earlier step that is required to enable subsequent fusion.

The requirement for numerous cellular factors including glycosaminoglycans, SR-BI, CD81 and now CLDN1, indicates that HCV cell entry is a complex multi-step process (reviewed in 7-9). An important challenge will be to delineate the precise function that each cellular entry factor fulfills. Our data suggest a role for CLDN1 late in the HCV entry process, perhaps downstream of interactions with other virus-receptor/co-receptors such as CD81. However, differences in blocking antibody efficacy are an important caveat to bear in mind when interpreting the inhibition data in FIG. 25b.

Example 6

Description of Various Techniques and Materials Used in the Examples

293T, HeLa, Hep3B, Hepa1.6, HepG2, HepH, Huh-7.5, SW13 and TZM cells were maintained in DMEM with 10% fetal bovine serum (FBS). CHO cells were maintained in DMEM/F-12 with 10% FBS. HepG2 were grown on collagen coated plastic.

Mouse monoclonal antibodies against CLDN1 (clone 2H10D10), 3 and 7 were purchased from Zymed Laboratories (San Francisco, Calif.). Mouse anti-CD81 1.3.3.22 was obtained from Santa Cruz Biotechnology (Santa Cruz, Calif.). Purified mouse IgG1 was from BD Pharmingen (Franklin Lakes, N.J.). The mouse anti-GFP, mouse anti-β-actin and HRP-anti-mouse-IgG used for immunoblotting were from Novus Biologicals (Littleton, Colo.), Sigma (St. Louis, Mo.), and Pierce (Rockford, Ill.), respectively. HRP detection was performed with SuperSignal West Pico Substrate (Pierce), according to the manufacturer's instructions. The mouse anti-NS5A antibody 9E10 has previously been described (Chung, C.S., et al. 2005 J Virol 79:1623-34). AlexaFluor488 conjugated anti-mouse IgG secondary antibodies were obtained from Invitrogen (Carlsbad, Calif.). For infection blocking, the M2 anti-FLAG antibody was obtained from Sigma (St. Louis, Mo.), JS81 anti-CD81 and negative control mouse IgG antibodies were from BD Pharmingen (Franklin Lakes, N.J.).

The pNL4.3.luc.R-.E-HIV genome has been described elsewhere (Colegio, O.R., et al. 2003 Am J Physiol Cell Physiol 284:C1346-54; Connor, R.L., et al. 1995 Virology 206:935-44). The HIV proviruses expressing from the Spleen focus forming virus promoter GFP (CSGW), puromycin resistance (CSPW) and zeocin resistance (CSZW) reporter genes were constructed within a self-inactivating proviral genome encoding a deletion in the 3' LTR U3 region, resulting in inactivation the viral promoter during reverse transcription and integration. The CSGW and CSPW plasmids have been previously described (Cormier, E.G., et al. 2004 Proc Natl Acad Sci USA 101:14067-72). CSZW was constructed by PCR amplification of the zeocin resistance gene open reading frame (ORF) from pcDNA3.1Zeo (Invitrogen, Carlsbad, Calif.) with the oligos 5'-GGGATCCGGG ATG GCC AAG TTG ACC AGT GCC GTT CCG (SEQ ID NO:4) (start codon in bold) and 5'-CCCCTCGAGTCTAGA TCA GTC CTG CTC CTC GGC CAC GAA GTG (SEQ ID NO:5) (stop codon in bold). This product was then digested with the BamHI and XbaI restriction endonucleases (New England Biolabs, Ipswich, Mass.) and cloned into a BamHI and partially XbaI digested CSGW plasmid, resulting in the replacement of the GFP coding sequence with that for zeocin resistance. Defined genes of interest were expressed in pTRIP (Cormier, E.G., et al. 2004 Proc Natl Acad Sci USA 101: 7270-4; Cowan, S., et al. 2002 Proc Natl Acad Sci USA 99:11914-9), a self-inactivating lentiviral provirus that expresses no HIV proteins, but instead employs an internal CMV promoter to express cloned genes. To create pTRIP-CLDN1, the CLDN1 ORF was amplified from the cDNA clones isolated in the screen with the oligos 5'-GGGG GGATCC GTC ATG GCC AAC GCG GGG CTG CAG CTG TTG GGC (SEQ ID NO:6) and 5'-GGGG CTCGAG TCA CAC GTA GTC TTT CCC GCT GGA AGG TGC (SEQ ID NO:7). This product was cloned as a BamHI and XhoI digested fragment into a likewise digested pTRIP plasmid. For amplification of CLDN3, CLDN7, and mouse CLDN1 ORF's, expressed sequence tag (EST) clones (ATCC numbers 6869006, 9035916, and 7156714, respectively) constructed by the Integrated Molecular Analysis of Genome Expression (I.M.A.G.E.) Consortium (image.llnl.gov) were obtained from the American Type Culture Collection (ATCC, Manassas, Va.). pTRIP-CLDN3 was constructed by amplification of the CLDN3 ORF with oligos 5'-GGGG GGATCC GCC ATG TCC ATG GGC CTG GAG ATC ACG GGC ACC (SEQ ID NO:8) and 5'-GGGG GTCGAC TTA GAC GTA GTC CTT GCG GTC GTA GCC TGT (SEQ ID NO:9) to generate a product that was cloned as a BamHI/SalI fragment into the BamHI/SalI digested pTRIP plasmid. pTRIP-CLDN7 was constructed by amplification of the CLDN7 ORF with oligos 5'-GGGG GGATCC ATG GCC AAT TCG GGC CTG CAG TTG CTG GGC (SEQ ID NO:10) and 5'-GGGG GTCGAC TCA CAC ATA CTC CTT GGA AGA GTT GGA CTT (SEQ ID NO:11) to generate a product that was cloned as a BamHI/SalI fragment into the BamHI/SalI digested pTRIP plasmid. The mouse CLDN1 ORF was amplified with oligos 5'-GGGG GGATCC GTC ATG GCC AAC GCG GGG CTG CAG CTG CTG GGT (SEQ ID NO:12) and 5'-GGGG CTCGAG TCA CAC ATA GTC TTT CCC ACT AGA AGG TGT TGG (SEQ ID NO:13). This fragment was cloned as a BamHI/XhoI fragment into a likewise digested pTRIP plasmid. The GFP-CLDN1 and CLDN7 fusions were constructed in the TRIP lentiviral vector by cloning of the GFP coding sequence, amplified with the oligos 5'-GGGG GGA TCC GGA ATG GTG AGC AAG GGC GAG GAG CTG TTC (SEQ ID NO:14) and 5'-GGGG AGA TCT CTT GTA CAG CTC GTC CAT GCC GAG AGT GAT (SEQ ID NO:15) and digested with BamHI/BglII, into the pTRIP-CLDN1 and pTRIP-CLDN7 at the BamHI sites of each plasmid to make pTRIP-GFP-CLDN1 and pTRIP-GFP-CLDN7, respectively. To generate TRIP-mCherryCLDN1, the CMV promoter and mCherry coding sequence, just short of the stop codon, was cloned from the pcDNA3.1mCherry plasmid (provided by Roger Y. Tsien, University of California at San Diego, La Jolla, Calif., USA.) as an NdeI/BsrGI fragment into pTRIP-GFP-CLDN1, so that the fluorescent protein coding sequences were exchanged.

Chimeric claudin expression constructs were constructed by overlapping PCR amplification. Briefly, forward and reverse oligos (sequences available upon request) that anneal to CLDN1 and CLDN7 coding sequences at desired junctions were used in combination with the forward GFP oligo, described above, or the oligo specific for the 3' end of the coding sequence of interest, described above, were used for first-round PCR with pTRIP-GFP-CLDN1 and pTRIP-GFP-CLDN7 plasmids as template. Each fragment was purified then amplified in a second round of PCR with only the most 5' and 3' specific oligo, thus generating fusion of claudin coding sequences at the desired junction. Final full-length fragments were cloned back into BamHI/XhoI digested pTRIP as BamHI/XhoI, for clones with the CLDN1 3' end, or BamHI/SalI, for clones with the CLDN7 3' end, fragments. PCR fragments encoding CLDN7 sequences with an internal XhoI site and the CLDN1 3' end were cloned by BamHI and partial XhoI digestion. Progressively smaller internal swaps were generated by repeating the above process using previous claudin chimeras as template. Claudin point mutants and EL1 deletions and insertions were generated by essentially the same procedure, where outside GFP and claudin 3' end specific oligos were used in conjunction with internal mutation specific oligos (sequences available upon request) in two rounds of PCR to generate coding sequence fragments with desired changes. For example, pTRIP-CLDN1 F10 was constructed by amplification of pTRIP-GFP-CLDN1 with the forward GFP oligo, described above, and the reverse oligo 5'-CTT GTC GTC ATC GTC CTT ATA GTC GAC CAA TGT GCT GCT CAG ATT CAG (SEQ ID NO:16), which creates a SalI site and a single FLAG epitope at the 3' end, and, in a separate reaction, the forward oligo 5'-GAC TAT AAG GAC GAT GAC GAC AAG CTT CAA GCA ACG CGT GCC TTG ATG GTG (SEQ ID NO:17) and the reverse oligo for the CLDN1 coding sequence, which creates a 5' single FLAG epitope and a HindIII site. The products were then amplified with the outside oligos to create a fragment with an internal FLAG epitope fusion within EL1 that was then cloned into pTRIP as a BamHI/XhoI digested fragment into a like digested vector. To insert the triple-FLAG epitope, the forward oligo 5'-GGGG GTC GAC TAC AAA GAC CAT GAC GGT GAT TAT AAA GAT CAT GAT ATC GAC TAT AAG GAC GAT GAC GAC AAG CTT (SEQ ID NO:18), encoding a SalI site, the triple epitope sequence, and a HindIII site, and the reverse oligo for the CLDN1 coding sequence were used in a PCR with the pTRIP-CLDN1 F10 plasmid as template. The triple-FLAG epitope was then cloned in place of the single epitope in the EL1 insertion mutant plasmids at the SalI/HindIII sites.

The Huh-7.5 cell cDNA library was assembled in a minimal HIV-1 provirus, termed V1, where most genes were deleted, but the Tat, Rev, and Vpu ORF's, as well as all necessary cis acting sequences remained intact (Coyne, C.B., et al. 2006 Cell 124:119-31; Cristea, I.M., et al. In preparation). In this plasmid, the Nef gene was also deleted and replaced with a cloning site where the cDNA of interest could be cloned and expressed. Variations of the V1 vector used in this study include V1-GFP, where the coding sequence for GFP was cloned into the Nef position, and V1dTat-GFP, where the V1-GFP plasmid was digested with MfeI, which cuts once 23 amino acids into the Tat open reading frame, filled-in with Klenow DNA polymerase, then religated to introduce a frame shift and thus prevents translation of Tat.

For cDNA construction, the SMART cDNA Library Construction Kit (Clontech, Mountain View, Calif.) protocol was essentially followed, with the following modifications: mRNA prepared from Huh-7.5 cells with Trizol Reagent (Invitrogen) and polyA selected with the Oligotex mRNA Maxi Kit (Qiagen, Valencia, Calif.) was subjected to poly-T primed first strand cDNA synthesis using the Superscript III First-Strand Synthesis System for RT-PCR (Invitrogen). Second strand cDNA was then synthesized and amplified using the TaqPlus Long PCR System (Stratagene, La Jolla, Calif.). Oligo sequences are identical to those described in the SMART cDNA Library Construction Kit. The resulting cDNA was the SfiI digested, fractionated by cDNA Size Fractionation Columns (Invitrogen), and cloned into an SfiI digested V1 vector. All DNA precipitation steps were replaced by purification using the QIAquick PCR Cleanup Kit (Qiagen). The final V1-Huh-7.5 cDNA library contained $2.5 \times 10^6$ clones with inserts averaging 970 bp in size.

Pseudovirus Generation and Infection Assays

All pseudoviruses were generated by co-transfection of plasmids encoding (1) a provirus containing the desired reporter gene or transgene, (2) HIV gag-pol, and (3) an appropriate envelope glycoprotein. Unless otherwise noted HCVpp used in this study were generated using the H77 E1E2 sequence (residues 170-746) (Danthi, P. et al. 2004 J Virol 78:33-41). The JFH1 E1E2 sequence was amplified using the oligos 5'-CAC CAT GGG TTT CCC CTT TTC TAT CTT (SEQ ID NO:19) and 5'-CTA CTA TGC TTC GGC CTG GCC CAA CAA GAT GAG CAT CCA (SEQ ID NO:20) and cloned into pcDNA3.1D/V5HisTOPO (Invitrogen, Carlsbad, Calif.). Other E1E2 sequences (Con1, OH8, HC-J6) used for HCVpp generation have been described previously(Date, T., et al. 2004 J Biol Chem 279:22371-6). On the day prior to transfection $8 \times 10^5$ 293T cells were seeded in a 35 mm well. The following day a total of 1.5 µg DNA was transfected using 6 µl FuGENE 6 (Roche Applied Science, Indianapolis, Ind.). Media was replaced after 6 h Supernatants were harvested at 48 h and 72 h after transfection, pooled and filtered (0.45 µm pore size). The following plasmid combinations and ratios (by weight) were used: To generate luciferase reporter HCVpp and controls, equal amounts of pNL43.luc.R-.E-(encoding a provirus containing luciferase and HIV gag-pol) and either HCV E1E2, VSV-G or empty vector were co-transfected giving rise to HCVpp, VSV-Gpp and envelope-deficient pseudoparticles (Env-pp), respectively—as previously reported (Connor, R.I., et al. 1995 Virology 206:935-44). To generate GFP, puromycin or zeocin reporter HCVpp and controls, plasmids encoding (1) a provirus encoding the respective reporter gene (CSGW, CSPW or CSZW), (2) HIV gag-pol, and (3) either HCV strain H77 E1E2, VSV-G or empty vector were transfected at a 1:1:4 ratio. To generate pseudoparticles for transgene delivery, plasmids encoding (1) either a V1 or pTRIP provirus containing the desired transgene, (2) HIV gag-pol, and (3) VSV-G were co-transfected at a 2:2:1 ratio. (For details on pseudovirus generation in the context of cyclic repackaging see below.) All transductions and infection assays using pseudoviruses were performed in the presence of 4 µg/ml polybrene.

Infection assays with luciferase reporter pseudoparticles were performed in a 96-well format using 104 target cells per well. Cells were infected with pseudovirus supernatants diluted in fresh media (1:5 for HCVpp and Env-pp; 1:5000 for VSV-Gpp) and polybrene was added to a final concentration of 4 µg/ml. After 6-18 h the media was changed. Luciferase assays were performed 72 h after infection as previously described (Connor, R.I., et al. 1995 Virology 206:935-44). Briefly, cells were lysed with 30 µl cell culture lysis buffer (Promega Madison, Wis.) and the expression of the luciferase reporter was measured after the addition of 100 µl luciferase substrate (Promega) on a Centro LB960 luminometer (Berthold Technologies, Bad Wildbad, Germany). For infection assays with GFP reporter HCVpp, $3 \times 10^4$ cells were plated in 48-well-plates. The next day the cells were infected with pseudovirus for 6 h. The media was changed and cells were further cultured for 48 h prior to harvesting and fixation with 1% w/v para-formaldehyde. GFP expression was quantified using a FACSCalibur flow cytometer (Becton Dickinson, Franklin Lakes, N.J.). Except where noted otherwise, results of infection experiments are represented as the mean of greater than three independent replicate wells, and, in the case of the chimera and mutant claudin analysis, of at least two independently transduced populations. Error bars represent the standard deviation.

Antibody inhibition experiments of non-synchronized infections were performed as above except 30 min prior to infection media was changed to media containing the indicated quantities of M2 antibody (Sigma, St. Louis, Mo.) and antibody was also added to pseudoparticles dilutions at the same concentration. For synchronized infections, 105 cells were seeded in poly-L-lysine coated 24 well tissue culture plates 24 h prior to infection. Media was changed to 4° C. media with or without antibody 30 min (t=−150 min in assay) prior to infection and cultures were placed at 4° C. At t=−120 min, media was replaced with 200 µl pseudoparticles containing 4 µg/mL polybrene and 50 mM Hepes, with or without antibody as indicated, and cultures were again placed at 4° C. At t=0 min, cultures were washed twice with cold PBS, then fresh 37° C. media, with or without antibodies, was added and cultures were placed in 37° C. tissue culture incubators. At indicated time points antibodies were added to the media at indicated concentrations. At 18 h post infection, media was changed to fresh media without antibodies. Lysates were harvested 3 days post infection in 100 µl cell culture lysis buffer and the expression of the luciferase reporter was measured as indicated above.

cDNA Library Screening and Cyclic Packaging Rescue

A schematic overview of the iterative library screening approach is provided in Supplemental FIG. 1a. cDNA cloned into the lentiviral V1 vector was packaged into pseudovirus particles bearing VSV-G glycoprotein as described above. Since the V1 vector does not encode a reporter gene, pseudoviruses carrying this library were first titered alongside a stock of V1-GFP virus on the HeLa-derived TZM indicator cell line. TZM cells have an integrated lacZ gene that is transcribed via the HIV-1 LTR (Davis-Poynter, N., et al. 1994 J Virol 68:7586-90), thus infection of a TZM cell by a V1 containing pseudotype results in Tat expression from the V1 provirus and lacZ activation. The infectivity of the V1-library and V1-GFP viruses was measured on TZM cells using the lacZ reporter in a limiting dilution type assay (Dean, M., et al. 1996 Science 273:1856-62). The determined titers were then used to approximate the effective titer of the library virus on the cell line of interest, based on the measurable infectivity of V1-GFP on the cell line of interest. VSV-Gpp carrying the V1-library were then used to transduce 293T cells at a multiplicity of infection of about 1. Approximately $5 \times 10^6$ cells were transduced for the first round of screening; lower numbers were used in subsequent rounds. 293T cells expressing the library were challenged with HCVpp carrying a puromycin (CSPW) or zeocin (CSZW) reporter. After 48 h antibiotic selection was applied. Surviving cell clones were pooled and transfected with HIV gag-pol and VSV-G to re-package the V1/cDNA genomes present in these cells into pseudoparticles and deliver them to a naïve population of 293T cells for additional rounds of selection. We performed a total of five selection steps, i.e., infection with HCVpp encoding either puromycin or zeocin resistance followed by selection with the respective antibiotic. Puromycin was used three times and zeocin twice. After each selection step a fraction of the population was challenged with GFP reporter Env-pp, HCVpp and VSV-Gpp to monitor for the appearance of an HCVpp susceptible subpopulation (FIG. 4).

HCVcc Generation and Infection Assays

HCVcc were generated as previously reported (Chung, C.S., et al. 2005 J Virol 79:1623-34). Briefly, a plasmid encoding the chimeric J6/JFH genome was linearized with XbaI and transcribed using MEGAscript T7 (Ambion, Austin, Tex.). RNA was electroporated into Huh-7.5 cells using a ECM 830 (BTX Genetronics). 72 h after electroporation the supernatant was transferred to naïve Huh-7.5 cells. These cells were incubated for 72-96 h before the supernatant was again transferred to naïve cells. This procedure was performed 3-4 times to generate high-titer HCVcc stocks. Finally, filtered supernatants were titered on Huh-7.5 using a limiting dilution assay as described 30. For infection experiments 293T cells were seeded in 35 mm dishes. The next day HCVcc containing supernatant was applied. At 72 h post, infection was detected by immunohistochemical staining for NS5A with the 9E10 anti-NS5A as primary and an HRP-conjugated anti-mouse-IgG (Immpress, Vector, Burlingame, Calif.) as secondary antibody. DAB chromogen (DakoCytomation, Carpinteria, Calif.) served as substrate. Different from the published protocol 30, 293T cells were air dried prior to methanol fixation to avoid cell loss during staining procedures. For Huh-7.5 HCVcc infections, a J6/JFH based HCVcc encoding a *Renilla* luciferase reporter gene upstream of core (FL-J6/JFH-5'C19Rluc2AUbi) was used as previously described (Deleersnyder, V., et al. 1997 J Virol 71:697-704). *Renilla* luciferase assays were performed with reagents from Promega (Madison, Wis.), according to the manufacturer's instructions.

RNA Interference

Small interfering RNA oligonucleotides (siRNA's) were purchased from Dharmacon (Lafayette, Colo.). All siRNA's targeting CLDN1 corresponded to 19 nucleotide regions in the CLDN1 reference sequence (accession NM_021101): 5'-AGUGGAGGAUUUACUCCUA (subsequently referred to as "306") (SEQ ID NO:21); 5'-UGAAGUGUAUGAAGUGCUU (525) (SEQ ID NO:22); 5'-UGGUAUGGCAAUAGAAUCG (635) (SEQ ID NO:23); 5'-CACCAAGGCCCUAUCCAAA (804) (SEQ ID NO:24); 5'-UAACAUUAGGACCUUAGAA (921) (SEQ ID NO:25); 5'-UUCCAUAUUGAUGAAGAUG (1259) (SEQ ID NO:26). A sequence without close homology to any expressed human sequence (5'-UAGCAGCUAAACACAUCAA) (SEQ ID NO:27) was used as an irrelevant control. The siRNA targeting CD81 (5'-UGAUGUUCGUUGGCUUCCU) (SEQ ID NO:28) has previously been described (Demaison, C., et al. 2002 Hum Gene Ther 13:803-13). To achieve a robust reduction of protein levels, cells were transfected twice on days one and five. On the day before transfection 1.8×10⁵ cells were seeded in 35 mm wells. For transfection 6 μl Lipofectamine2000 (Invitrogen, Carlsbad, Calif.) and 150 pmol siRNA were used per well. Between transfections, cells were passaged as needed to keep them subconfluent. Protein expression and infection assays were performed on day 8.

Cell-Cell Fusion Assay

To create acceptor cells capable of responding to fusion with a Tat-expressing cell, 293T cells were transduced with V1dTat-GFP-VSV-Gpp. From this population, cell clones were isolated that expressed little to no GFP in the absence of Tat, but had a high reporter signal when infected with V1 VSV-Gpp, which expresses Tat. GFP expression was quantified by flow cytometry as described above. Two clones that exhibited the tightest Tat regulation of GFP expression were used in parallel analyses with equivalent results (data not shown). To test the effects of CLDN1 in this assay, the acceptor cell clones were transduced with TRIP-mCherryCLDN1 VSV-Gpp, which renders 293T cells susceptible to luc-HCVpp (data not shown).

To create donor cell populations, 293T cells, seeded in a 6-well plate, were transfected with either mock V1 vector, to provide Tat expression, a glycoprotein expression vector (either H77 HCV E1E2 or VSV-G), or V1 plus glycoprotein. Transfections were performed with Fugene-6 as described above. At 36 h post transfection, combinations of donor and acceptor cells were co-seeded (1.5×10⁶ cells each/well) in 2-well chamber slides (BD Falcon). 12 h later, cells were washed with citric acid buffer at either pH 5 or pH 7 (15 mM citric acid, 150 mM NaCl), followed by media to neutralize the pH, and incubated for an additional 36-48 h. Slides were fixed with 2% w/v paraformaldehyde and mounted with 80% glycerol. Green foci were enumerated by eye using a Nikon Eclipse TE300 fluorescent microscope. Averages of three replicate experiments are shown with error bars representing the standard deviation.

HCVcc Cell Binding Assay

CHO cells, mock transduced, or transduced with human CD81, CLDN1, or SR-BI, seeded in triplicate wells, were incubated with J6/JFH HCVcc (MOI ~0.5) for 2 h at 37° C. After binding, the cells were washed extensively with DPBS and total RNA was harvested using the RNeasy Mini kit (Qiagen). HCV RNA was amplified from 100 ng total RNA using the LightCycler RNA Amplification kit (Roche) and detected using a LightCycler 480 (Roche). The forward and reverse primer sequences were 5' CTT CAC GCA GAA AGC GTC TA 3' (SEQ ID NO:29) and 5' CAA GCA CCC TAT CAG GCA GT 3' (SEQ ID NO:30), respectively (Applied Biosystems). The probe sequence was 5' FAM-TAT GAG TGT CGT GCA GCC TC-MGBNFQ 3' (SEQ ID NO:31) (Applied Biosystems).

Statistical Analyses

Curve fitting and all statistical analyses were performed using Prism4 software (GraphPad Software, San Diego, Calif.).

Example 7

Figure 29:
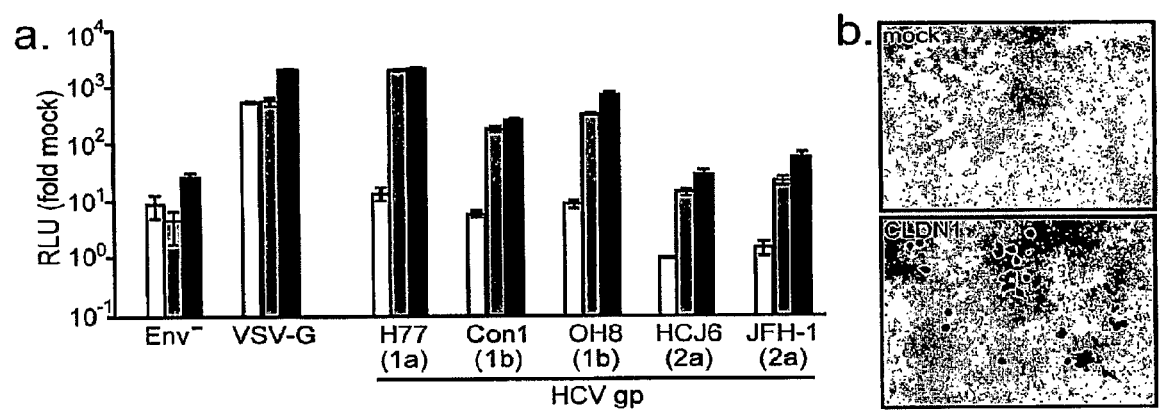

Demonstration that Claudin-1 Mediates Entry of Multiple HCV Genotypes and Subtypes Expression of CLDN1 specifically enhanced 293T susceptibility to luciferase-reporter HCVpp of diverse genotypes more than 100-fold (FIG. 29). CLDN1 did not affect 293T susceptibility to pseudoparticles bearing either no envelope proteins (Env-pp; data not shown) or the unrelated vesicular stomatitis virus G protein (VSV-Gpp), which serve as negative and positive infection controls, respectively.

Various patent and non-patent publications are cited herein, the disclosures of each of which are incorporated herein by reference in their entireties. Certain biological sequences referenced herein by their "NCBI Accession Number" or common names can be accessed through the National Center of Biotechnology Information on the world wide web at ncbi.nlm.nih.gov.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

---

What is claimed is:

1. A method of screening for an inhibitor of Hepatitis C Virus (HCV) infection, said method comprising screening a library for a compound which prevents or mitigates binding of any one of: i) a cell expressing HCV envelope proteins E1 and E2, ii) an HCV pseudotyped retroviral particle comprising an HCV E1 protein and an HCV E2 protein, iii) an HCV cell culture particle, iv) an ex vivo HCV cell culture particle, or v) a Hepatitis C Virus with a Claudin-1 protein, conservative amino acid substitutions thereof, a Claudin-1/Claudin-7 chimera comprising a Claudin-1 extracellular loop 1, or a Claudin-7 protein wherein residues corresponding to residues 32 and 48 of a Claudin-1 protein as shown in SEQ ID NO: 1 are respectively substituted in said Claudin-7 protein with isoleucine and glutamic acid.

2. A method of identifying a compound or agent that prevents or mitigates interaction of any one of: i) a cell expressing HCV envelope proteins E1 and E2, ii) an HCV pseudotyped retroviral particle comprising an HCV E1 protein and an HCV E2 protein, iii) an HCV cell culture particle, iv) an ex vivo HCV cell culture particle, or v) a Hepatitis C Virus with a Claudin-1 protein, said method comprising the steps of:
   a) providing either i) a recombinant protein comprising a Claudin-1 protein as shown in SEQ ID NO:1 or conservative amino acid substitutions thereof, a Claudin-1/Claudin-7 chimera comprising a Claudin-1 extracellular loop 1, or a Claudin-7 protein wherein residues corresponding to residues 32 and 48 of a Claudin-1 protein as shown in SEQ ID NO: 1 are respectively substituted in said Claudin-7 protein with isoleucine and glutamic acid; or ii) a cell comprising a recombinant vector that provides for expression of a membrane bound protein comprising a Claudin-1 protein as shown in SEQ ID NO:1 or conservative amino acid substitutions thereof, a Claudin-1/Claudin-7 chimera comprising a Claudin-1 extracellular loop 1, or a Claudin-7 protein wherein residues corresponding to residues 32 and 48 of the Claudin-1 protein as shown in SEQ ID NO: 1 are respectively substituted in said Claudin-7 protein with isoleucine and glutamic acid; wherein said cell is a CD81 positive, SR-BI positive human cell line that is susceptible to an HCV pseudotyped retroviral particle;
   b) contacting said protein or said cell from step (a) with an agent or a compound and a cell expressing HCV envelope proteins E1 and E2, an HCV pseudotyped retroviral particle comprising an HCV E1 protein and an HCV E2 protein, an HCV cell culture particle, an ex vivo HCV cell culture particle or HCV; and
   c) determining if said compound or agent inhibits interaction or fusion of said protein or said cell provided in (a) with said HCV envelope protein, said cell expressing HCV envelope proteins E1 and E2, said HCV pseudotyped retroviral particle, said HCV cell culture particle, said ex vivo HCV cell culture particle, or said HCV provided in step (b), thereby identifying a compound or agent that prevents or mitigates interaction of a cell expressing HCV envelope proteins E1 and E2, an HCV pseudotyped retroviral particle, an HCV cell culture particle, an ex vivo HCV cell culture particle, or a Hepatitis C Virus with a Claudin-1 protein.

3. The method of claim 2, wherein said cell in step (a) is a 293T or a SW13 cell.

4. The method of claim 2, wherein inhibition of interaction of said recombinant protein of step (a) is determined in step (c) by assaying for retention of the recombinant protein by said cell expressing HCV envelope proteins E1 and E2, said HCV pseudotyped retroviral particle, by said HCV cell culture particle, said by ex vivo HCV cell culture particle, or by said HCV provided in step (b), wherein decreased retention of the recombinant protein is indicative of binding inhibition.

5. The method of claim 2, wherein said determination of interaction or fusion in step (c) is effected by assaying a reporter protein.

6. A kit for identifying a compound or agent that prevents or mitigates interaction of a cell expressing HCV envelope proteins E1 and E2, an HCV pseudotyped retroviral particle, an HCV cell culture particle, an ex vivo HCV cell culture particle or a Hepatitis C Virus with a Claudin-1 protein, said kit comprising either i) a recombinant protein comprising a Claudin-1 protein as shown in SEQ ID NO:1 or conservative amino acid substitutions thereof, or ii) a recombinant vector that provides for expression of a Claudin-1 protein as shown in SEQ ID NO:1 or conservative amino acid substitutions thereof, a Claudin-1/Claudin-7 chimera comprising a Claudin-1 extracellular loop 1, or a Claudin-7 protein wherein residues corresponding to residues 32 and 48 of the Claudin-1 protein as shown in SEQ ID NO: 1 are respectively substituted in said Claudin-7 protein with isoleucine and glutamic acid; or iii) a cell comprising said recombinant vector, wherein said cell-is a CD81 positive, SR-BI positive human cell line that is susceptible to an HCV pseudotyped retroviral particle protein, wherein said kit further comprises an HCV envelope protein, a recombinant vector encoding HCV envelope proteins E1 and E2, a recombinant vector encoding an HCV pseudotyped retroviral particle comprising an HCV E1 protein and an HCV E2 protein, a recombinant vector encoding an HCV cell culture particle, or a recombinant vector encoding an infectious HCV particle.

7. A cell culture composition comprising: i) a cell comprising a recombinant vector that provides for expression of a Claudin-1 protein as shown in SEQ ID NO:1 or conservative amino acid substitutions thereof, a Claudin-1/Claudin-7 chimera comprising a Claudin-1 extracellular loop 1, or a Claudin-7 protein wherein residues corresponding to residues 32 and 48 of a Claudin-1 protein as shown in SEQ ID NO: 1 are respectively substituted in said Claudin-7 protein with isoleucine and glutamic acid, wherein said-cell is a CD81 positive, SR-BI positive human cell line that is susceptible to an HCV pseudotyped retroviral particle; and either ii) a cell comprising a recombinant vector that encodes HCV envelope proteins E1 and E2 or iii) any one of a HCV pseudotyped retroviral particle comprising an HCV E1 protein and an HCV E2 protein, an HCV cell culture particle, an ex vivo HCV cell culture particle, or an HCV particle.

8. The cell culture composition of claim 7, wherein said HCV pseudotyped retroviral vector comprises an HCV E1 protein, an HCV E2 protein and a packaging competent retroviral genome containing a reporter gene.

9. The cell culture composition of claim 8, wherein said packaging competent retroviral genome is an HIV or an MLV packaging competent retroviral genome.

10. The cell culture composition of claim 8, wherein said packaging competent retroviral genome is an envelope deficient retroviral genome.

11. The kit of claim 6, wherein said kit further comprises instructions for using said kit to identify a compound or agent that prevents or mitigates interaction of said cell expressing HCV envelope proteins E1 and E2, said HCV pseudotyped retroviral particle, said HCV cell culture particle, said ex vivo HCV cell culture particle, or said Hepatitis C Virus with a Claudin-1 protein.

* * * * *